United States Patent
Oronsky et al.

(10) Patent No.: US 11,660,286 B2
(45) Date of Patent: May 30, 2023

(54) METHODS AND COMPOSITIONS COMPRISING A NITRITE-REDUCTASE PROMOTER FOR TREATMENT OF MEDICAL DISORDERS AND PRESERVATION OF BLOOD PRODUCTS

(71) Applicant: EpicentRx, Inc., La Jolla, CA (US)

(72) Inventors: Bryan T. Oronsky, Los Altos Hills, CA (US); Jan Scicinski, Saratoga, CA (US); Susan Knox, Stanford, CA (US); William Fitch, Palo Alto, CA (US); Frans A. Kuypers, El Cerrito, CA (US); Marcel Fens, San Francisco, CA (US); Sandra Larkin, Berkeley, CA (US); Pedro Cabrales, San Diego, CA (US); Chad Brouse, San Diego, CA (US)

(73) Assignee: EPICENTRX, INC., La Jolla, CA (US)

( * ) Notice: Subject to any disclaimer, the term of this patent is extended or adjusted under 35 U.S.C. 154(b) by 0 days.

(21) Appl. No.: 16/284,035

(22) Filed: Feb. 25, 2019

(65) Prior Publication Data
US 2020/0022952 A1    Jan. 23, 2020

Related U.S. Application Data

(63) Continuation of application No. 14/349,010, filed as application No. PCT/US2012/058964 on Oct. 5, 2012, now abandoned.

(60) Provisional application No. 61/544,375, filed on Oct. 7, 2011.

(51) Int. Cl.

| | | |
|---|---|---|
| *A61K 31/397* | (2006.01) | |
| *A61K 33/00* | (2006.01) | |
| *A61K 45/06* | (2006.01) | |
| *A61K 31/22* | (2006.01) | |
| *A61K 31/12* | (2006.01) | |
| *A61K 31/255* | (2006.01) | |
| *A61K 31/445* | (2006.01) | |
| *A61K 31/215* | (2006.01) | |
| *A61K 31/16* | (2006.01) | |
| *A61K 31/198* | (2006.01) | |
| *A61K 31/40* | (2006.01) | |
| *A61K 47/64* | (2017.01) | |
| *A01N 1/02* | (2006.01) | |
| *A61K 35/14* | (2015.01) | |
| *A61K 35/16* | (2015.01) | |
| *A61K 35/18* | (2015.01) | |
| *A61K 38/17* | (2006.01) | |
| *A61N 5/10* | (2006.01) | |

(52) U.S. Cl.
CPC .......... *A61K 31/397* (2013.01); *A01N 1/0226* (2013.01); *A61K 31/12* (2013.01); *A61K 31/16* (2013.01); *A61K 31/198* (2013.01); *A61K 31/215* (2013.01); *A61K 31/22* (2013.01); *A61K 31/255* (2013.01); *A61K 31/40* (2013.01); *A61K 31/445* (2013.01); *A61K 33/00* (2013.01); *A61K 35/14* (2013.01); *A61K 35/16* (2013.01); *A61K 35/18* (2013.01); *A61K 38/1709* (2013.01); *A61K 45/06* (2013.01); *A61K 47/6445* (2017.08); *A61N 5/10* (2013.01); *Y02A 50/30* (2018.01)

(58) Field of Classification Search
CPC .... A61K 2300/00; A61K 31/12; A61K 31/16; A61K 31/198; A61K 31/215; A61K 31/22; A61K 31/255; A61K 31/397; A61K 31/40; A61K 31/445; A61K 33/00; A61K 35/14; A61K 35/16; A61K 35/18; A61K 38/1709; A61K 45/06; A61K 47/6445; A01N 1/0226; A01N 5/10; Y02A 50/411; Y02A 50/30
See application file for complete search history.

(56) References Cited

U.S. PATENT DOCUMENTS

| | | |
|---|---|---|
| 2,978,453 A | 4/1961 | Milton |
| 3,845,770 A | 11/1974 | Theeuwes et al. |
| 3,916,899 A | 11/1975 | Theeuwes et al. |

(Continued)

FOREIGN PATENT DOCUMENTS

| | | |
|---|---|---|
| CN | 200946766 Y | 9/2007 |
| DE | 10111049 A1 | 9/2002 |

(Continued)

OTHER PUBLICATIONS

Schwartz Am. J. Health-Syst. Pharm. (2007) 64(Supplement 2): S5-S13 (Year: 2007).*
Wong Chemistry of Protein Conjugation and Cross-linking CRC Press: Boca Raton: FL (1991) (Year: 1991).*
Weyerbrock et al. Journal of Neurosurgery (2003), 99(4), 728-737 (Year: 2003).*

(Continued)

*Primary Examiner* — Susan M Hanley
(74) *Attorney, Agent, or Firm* — Morrison & Foerster LLP

(57) ABSTRACT

The invention provides methods, compositions, and medical kits comprising a nitrite-reductase promoter, such as an allosteric modulator of hemoglobin, for use in treating medical disorders and preservation of blood products. In one aspect, the invention provides methods, compositions, and medical kits comprising an inorganic nitrite salt and a nitrite-reductase promoter, such as an allosteric modulator of hemoglobin, for use in treating medical disorders, such as cancer, cardiovascular disorders, ischemic conditions, hemolytic conditions, and bacterial infections. Exemplary inorganic nitrite salts include sodium nitrite and arginine nitrite. Exemplary allosteric modulators of hemoglobin described herein include alkyl-substituted and acyl-substituted di-nitroheterocycles.

6 Claims, 13 Drawing Sheets

(56) References Cited

U.S. PATENT DOCUMENTS

| | | | |
|---|---|---|---|
| 4,584,130 A * | 4/1986 | Bucci | C07C 317/00 514/13.4 |
| 4,765,539 A | 8/1988 | Noakes et al. | |
| 5,112,598 A | 5/1992 | Biesalski | |
| 5,336,784 A | 8/1994 | Hiskey et al. | |
| 5,521,203 A | 5/1996 | Adams et al. | |
| 5,556,611 A | 9/1996 | Biesalski | |
| 5,579,458 A | 11/1996 | Yokosuka et al. | |
| 5,580,988 A | 12/1996 | Dave | |
| 5,607,830 A | 3/1997 | Biesel et al. | |
| 5,679,777 A | 10/1997 | Anderson et al. | |
| 5,693,794 A | 12/1997 | Nielsen | |
| 5,698,155 A | 12/1997 | Grosswald et al. | |
| 5,950,619 A | 9/1999 | van der Linden et al. | |
| 5,954,047 A | 9/1999 | Armer et al. | |
| 5,970,974 A | 10/1999 | Van Der Linden et al. | |
| 6,133,320 A | 10/2000 | Yallampalli et al. | |
| 6,245,799 B1 | 6/2001 | Asselin et al. | |
| 6,391,911 B1 | 5/2002 | Bases | |
| 6,407,236 B1 | 6/2002 | Baraldi et al. | |
| 7,163,958 B2 | 1/2007 | Earl et al. | |
| 7,507,842 B2 | 3/2009 | Knox et al. | |
| 7,745,643 B2 | 6/2010 | Cannizzo et al. | |
| 8,178,698 B2 | 5/2012 | Cannizzo et al. | |
| 8,299,053 B2 | 10/2012 | Bednarski et al. | |
| 8,664,247 B2 | 3/2014 | Scicinski et al. | |
| 8,927,527 B2 | 1/2015 | Bednarski et al. | |
| 9,139,519 B2 | 9/2015 | Scicinski et al. | |
| 9,226,915 B2 | 1/2016 | Bednarski et al. | |
| 9,468,625 B2 | 10/2016 | Scicinski et al. | |
| 9,987,270 B1 | 6/2018 | Oronsky et al. | |
| 10,149,832 B2 | 12/2018 | Bednarski et al. | |
| 10,342,778 B1 | 7/2019 | Oronsky et al. | |
| 10,543,208 B2 | 1/2020 | Oronsky et al. | |
| 11,008,287 B2 | 5/2021 | Oronsky et al. | |
| 11,160,784 B1 | 11/2021 | Oronsky et al. | |
| 11,510,901 B2 | 11/2022 | Oronsky et al. | |
| 2002/0137770 A1 | 9/2002 | Nara et al. | |
| 2003/0092684 A1 * | 5/2003 | Fredeking | C07K 16/241 514/152 |
| 2004/0024057 A1 | 2/2004 | Earl et al. | |
| 2004/0167212 A1 | 8/2004 | Bednarski et al. | |
| 2005/0070872 A1 | 3/2005 | Sato et al. | |
| 2006/0111272 A1 | 5/2006 | Roberts et al. | |
| 2006/0211639 A1 * | 9/2006 | Bratzler | A61K 38/212 514/44 R |
| 2007/0135384 A1 | 6/2007 | Bednarski et al. | |
| 2008/0255149 A1 | 10/2008 | Dobler et al. | |
| 2008/0256149 A1 | 10/2008 | Bansal et al. | |
| 2009/0093644 A1 | 4/2009 | Cannizzo et al. | |
| 2009/0163466 A1 * | 6/2009 | Bednarski | A61P 35/00 514/210.17 |
| 2009/0192085 A1 | 7/2009 | Robson et al. | |
| 2010/0247682 A1 | 9/2010 | Gladwin et al. | |
| 2010/0260719 A1 * | 10/2010 | Zeldis | A61K 31/454 424/85.7 |
| 2011/0130572 A1 | 6/2011 | Cannizzo et al. | |
| 2011/0195947 A1 | 8/2011 | Straessler et al. | |
| 2012/0149678 A1 | 6/2012 | Oronsky et al. | |
| 2013/0053418 A1 | 2/2013 | Scicinski et al. | |
| 2013/0123216 A1 | 5/2013 | Bednarski et al. | |
| 2014/0220163 A1 | 8/2014 | Babadi et al. | |
| 2014/0308260 A1 | 10/2014 | Oronsky et al. | |
| 2014/0349988 A1 | 11/2014 | Scicinski et al. | |
| 2015/0190465 A1 | 7/2015 | Faivre et al. | |
| 2015/0246020 A1 | 9/2015 | Bednarski et al. | |
| 2016/0081981 A1 | 3/2016 | Scicinski et al. | |
| 2016/0199346 A1 | 7/2016 | Bednarski et al. | |
| 2018/0085346 A1 | 3/2018 | Bednarski et al. | |
| 2019/0125742 A1 | 5/2019 | Oronsky et al. | |
| 2019/0307723 A1 | 10/2019 | Oronsky et al. | |
| 2020/0046682 A1 | 2/2020 | Bednarski et al. | |
| 2020/0157047 A1 | 5/2020 | Oronsky et al. | |
| 2020/0254016 A1 | 8/2020 | Oronsky | |
| 2020/0345689 A1 | 11/2020 | Oronsky et al. | |
| 2020/0345690 A1 | 11/2020 | Oronsky et al. | |
| 2020/0375982 A1 | 12/2020 | Oronsky et al. | |
| 2021/0178050 A1 | 6/2021 | Oronsky et al. | |
| 2021/0244870 A1 | 8/2021 | Oronsky et al. | |
| 2022/0016077 A1 | 1/2022 | Bednarski et al. | |
| 2022/0054480 A1 | 2/2022 | Oronsky et al. | |

FOREIGN PATENT DOCUMENTS

| | | |
|---|---|---|
| EP | 412211 A1 | 2/1991 |
| JP | S48-030376 B | 9/1973 |
| JP | S5511509 A | 1/1980 |
| JP | H05155847 A | 6/1993 |
| JP | 2001506974 A | 5/2011 |
| JP | 2014530811 A | 11/2014 |
| RU | 2265440 C2 | 12/2005 |
| RU | 2411953 C1 | 2/2011 |
| WO | WO-1995032715 A1 | 12/1995 |
| WO | WO-1996036602 A1 | 11/1996 |
| WO | WO-1998016485 A1 | 4/1998 |
| WO | WO-1998016502 A1 | 4/1998 |
| WO | WO-1999016436 A1 | 4/1999 |
| WO | WO-1999059575 A1 | 11/1999 |
| WO | WO-2000006143 A1 | 2/2000 |
| WO | WO-2001077100 A2 | 10/2001 |
| WO | WO-2004032864 A2 | 4/2004 |
| WO | WO-2004098538 A2 | 11/2004 |
| WO | WO-2004113281 A1 | 12/2004 |
| WO | WO-2005046661 A2 | 5/2005 |
| WO | WO-2006102760 A1 | 10/2006 |
| WO | WO-2007022121 A2 | 2/2007 |
| WO | WO-2007022225 A2 | 2/2007 |
| WO | WO-2012078992 A1 | 6/2012 |
| WO | WO-2013052164 A1 | 4/2013 |
| WO | WO-2013052803 A2 | 4/2013 |
| WO | WO-2017123593 A1 | 7/2017 |

OTHER PUBLICATIONS

Anjaria et al. Expert Opinion Pharmacother. (2008) 9(6): 901-911 (Year: 2008).*

Takakura et al. J. Gastroenterol. (2006) 41: 77-8 (Year: 2006).*

Akhavan (2004). "Explosives and Propellants," Kirk-Othmer Encyclopedia of Chemical Technology, pp. 719-744.

Aiderman, (1984). "A Review of Cellulose Ethers in Hydrophilic Matrices for Oral Controlled-Release Dosage Forms," Int. J. Pharm. Tech. & Prod. Mfr., 5(3):1-9.

Archibald et al., (1990). "Synthesis and x-ray crystal structure of 1,3,3-trinitroazetidine," J. Org. Chem., 55:2920-2924.

Armstrong et al., (2002). "Role of Glutathione Depletion and Reactive Oxygen Species Generation in Apoptotic Signaling in a Human B Lymphoma Cell Line, Cell Death and Differentiation," Nature, 9:252-263.

Australian Examination Report received for Australian patent application No. 2006279589, dated May 18, 2012, 3 pages.

Bamba et al., (1979). "Release Mechanisms in Gelforming Sustained Release Preparations," Int. J. Pharm., 2:307-315.

Berge et al., (1997). "Pharmaceutical Salts," Journal of Pharmaceutical Sciences, 66(1):1-19.

Brown et al., (1998). "Tirapazamine: Laboratory Data Relevant to Clinical Activity," Anti-Cancer Drug Design, 13:529-539. Abstract Only.

Coburn et al., (1998). caplus an 1998:567551, RN 179894-08-7, 1 page.

Crowder et al., (1999). "Vibrational analysis of high-energy compounds: 1,3,3-trinitroazetidine and 1-acetvl-3, 3-dinitroazetidine," Journal of Energetic Materials, 17(1):49-68.

Crowder et al., (1999). caplus an 1999:171384, RN 179894-08-7,1 page.

Dave et al., (2000). "Convenient Acylative Dealkylation of Tertiary Amines," Journal of Organic Chemistry, 65:1207-1209.

Dave, (1996). "Acylative Dealkylation of N-tert-Butyl-3-substituted Azetidines: Facile Access to [1.1.0] Azabicyclobutane, 3-Hydroxyazetidinium Hydrochloride, and 3-Azetidinones," J. Org. Chem., 61:5453-5455.

(56) References Cited

OTHER PUBLICATIONS

During et al., (1989). "Controlled Release of Dopamine from a Polymeric Brain Implant: In Vivo Characterization," Annals of Neurology, 25(4):351-356. Abstract Only.

Feuer et al., (1954). "The Mannich reaction of certain dinitro alcohols with glycine and ethanolamine," Journal of American Chemical Society, 76:5124-5126.

Garver et al., (1984). "Catalyzed Oxidative Nitration of Nitronate Salts," J. Org. Chem. 50(10):1699-1702.

Gladwin et al., (2005). "The Emerging Biology of the Nitrite Anion," in Nature Chemistry and Biology, 1:308-31.

Goodson, (1984). "Dental Applications," Chapter 6 of Medical Applications of Controlled Release, 2:115-138.

Granelli et al., (2004). "SEL 1 Land Squamous Cell Carcinoma of the Esophagus," Clinical Cancer Research, 10:5857-5861.

Heller, (2010). "An Electrochemical Engineering Perspective of Nitric Oxide in Tumors: Why the Combination of an Allosteric Effector of Hemoglobin with Dietary Sodium Nitrite Should Be Effective in Treating Vascularized Tumors?," ECS Transactions, 28(33):1-6.

Hiskey et al., (1993). caplus an 1993:233785, RN 147636-85-9, 1 page.

Hiskey et al., (1994). caplus an 1994:700750, RN 158669-97-7, 1 page.

Hiskey et al., (1999). "Preparation of 1-Substituted-3,3-Dinitroazetidines," Journal of Energetic Materials, 17:233-254.

Hockel et al., (2001). "Tumor Hypoxia: Definitions and Current Clinical, Biologic, and Molecular Aspects," Journal of the National Cancer Institute, 93(4):266-276.

Howard et al., (1989). "Intracerebral Drug Delivery in Rats with Lesion-Induced Memory Deficits," J. Neurosurg., 71:105-112.

Huguenin et al., (2005). "Evaluation of the antitumoral potential of different nitric oxide-donating non-steroidal anti-inflammatory drugs (NO-NSAIDs) on human urological tumor cell lines," Cancer Letters, 218:163-170.

International Search Report and Written Opinion for PCT/US2011/064178 dated Apr. 17, 2012, 8 pages.

International Search Report and Written Opinion for PCT/US2012/038592 dated Aug. 10, 2012, 11 pages.

International Search Report and Written Opinion for PCT/US2012/058964, dated Apr. 5, 2013, 9 pages.

International Search Report for PCT/US2006/031722 dated May 29, 2007, 1 page.

International Search Report for PCT/US2006/031917 dated Jul. 20, 2007, 1 page.

International Search Report for PCT/US2011/021500 dated May 3, 2011, 4 pages.

Jia et al., (2002). "NO donors with anticancer activity," Expert Opin. Therapeut., 12(6):819-826.

Johnson et al., (2001). "Relationships Between Drug Activity in NCI Preclinical in Vitro and in Vivo Models and Early Clinical Trials," British J. Cancer, 84(10):1424-1431.

Kashfi et al., (2002). "Nitric Oxide-Donating Nonsteroidal Anti-Inflammatory Drugs Inhibit the Growth of Various Cultured Human Cancel Cells: Evidence of a Tissue Type-Independent Effect," J. Pharmacology Experimental Therapeutics, 303(3):1273-1282.

Katritzky et al., (1994). "Novel Syntheses of 1,3,3-Trinitroazetidine," J. Heterocyclic Chem., 31:271-275.

Konovalova et al., (2003). "Nitric oxide donor increases the efficiency of cytostatic therapy and retards the development of drug resistance," Nitric Oxide, 8(1):59-64.

Kornblum et al., (1983). "Oxidative Substitution of Nitroparaffin Salts," J. Org. Chem., 48:332-337.

Langer et al., (1983). "Chemical and Physical Structure of Polymers as Carriers for Controlled Release of Bioactive Agents: A Review," JMS-Rev. Macromol. Chem. Phys., pp. 61-126.

Langer et al., (1984). "Chapter 2: Medical Applications of Controlled Release," Classes of Systems, pp. 42-67.

Langer, (1990). "New Methods of Drug Delivery," Science, 249(4976):1527-1533.

Levy et al., (1985). "Inhibition of Calcification of Bioprosthetic Heart Valves by Local Controlled- Release Diphosphonate," Science, 228(4696):190-192.

Ling et al., (2005). "Phase I study of CM-Na combined with concurrent radiochemotherapy for advanced esophageal carcinoma," Chinese Journal of Cancer, 24(5):582-6. Abstract Only.

Lopez-Ferrer et al., (2002). "Differences in the O-Glycosylation Patterns Between Lung Squamous Cell Carcinoma and Adenocarcinoma," Am. J. Clin. Pathol., 118:749-755.

Lusk et al., (2004). "Electrochemical Oxidation of Alkylnitro Compounds PP-1345, A SERDP 'Seed' Activity," available online at <https://www.serdp-estcp.org/content/download/6439/85721/file/PP-1345-FR-01.pdf>, 30 pages.

Marchand et al., (1994). "Additions of X-Y Across the C(3)-N a-Bond in 1-Aza-3-ethylbicyclo[1.1.0]butane, Novel Routes to 3-Substituted Azetidines," Journal of Organic Chemistry, 59(18):5499-5501.

Marchand et al., (1995). "A Novel Approach to the Synthesis of 1,3,3-Trinitroazetidine," J. Org Chem., 60(15):4943-4946.

Maxwell et al., (1997). "Hypoxia-inducible factor-1 modulates gene expression in solid tumors and influences both angiogenesis and tumor growth," Proc. Natl. Acad. Sci. USA, 94:8104-8109.

McKenney et al., (1998). "Synthesis and thermal properties of 1,3-dinitro-3-(1', 3'-dinitroazetidin-3'-yl) azetidine (TNDAZ) and its admixtures with 1,3,3-trinitroazetidine (TNAZ)," Journal of Energetic Materials, 16:199-235.

Mendenhall et al., (2000). "Radiation Therapy for Squamous Cell Carcinoma of the Tonsillar Region: A Preferred Alternative to Surgery?" J. Clinical Oncology, 18(11):2219-2225.

Morales-Suarez-Varela et al., (1995). "Impact of Nitrates in Drinking Water on Cancer Mortality in Valencia, Spain," European Journal of Epidemiology, 11:15-21.

Muehlstaedt et al., (1975). caplus an 1976:89768, RN 58373-43-6, 1 page.

Nabi et al., (2001). "Primary squamous cell carcinoma of the prostate: a rare clinicopathological entity. Report of 2 cases and review of literature," Ural. Int., 66(4):216-219. Abstract Only.

Naimi et al., (2003). "Synthesis of 3'- and 5'-Nitrooxy Pyrimidine Nucleoside Nitrate Esters: "Nitric Oxide Donor" Agents for Evaluation as Anticancer and Antiviral Agents," J. Med. Chem., 46:995-1004.

Nara et al., (2002). caplus an 2002:169585, RN 402835-09-0, 1 page.

Newman et al., (2003). "Solid-state analysis of the active pharmaceutical ingredient in drug products," Drug Discovery Today, 8(19):898-905.

Nitrates and Nitrites Answers to Frequently Asked Questions, Ohio Bureau of Environmental Health, Health Assessment Section, Nov. 1, 2006, 2 pages.

Oxley et al., (1997). "Thermal Decomposition Pathways of 1,3,3-Trinitroazetidine (TNAZ), Related 3,3- Dinitroazetidium Salts, and 15N, 13C, and 2H Isotopomers," Journal of Physical Chemistry A, 101(24):4375-4383.

Padwa et al., (1985). "Diastereofacial selectivity in azomethine ylide cycloaddition reactions derived from chiral α-cyanoaminosilanes," Tetrahedron, 41(17):3529-3535.

Peiris et al., (2001). "Structures of dinitroazetidine and three of its carbonyl derivatives," Journal of Chemical Crystallography, 30(10):647-653.

Prezioso et al., (1994). "Genetic Toxicity Evaluation of 1,3,3-Trinitroazetidine, vol. IV: Summary Report on the Genotoxicity of TNAZ," AL/OE-TR-1994-0069 vol. IV of IV, Air Force Materiel Command, Wright-Patterson Air Force Base, Ohio, 22 pages.

Raleigh et al., (1999). "P269: Pharmacokinetics of Isotretinoin (ISO) in Rats Following Oral Dosing or Aerosol Inhalation," British J. Cancer, 80(suppl 2):96.

Remington, (1995). "The Science and Practice of Pharmacy," 19th Edition, vol. II, pp. 1495-1562, 1577-1614, and 1660-1692.

Rosenthal, (1999). "A Phase I Single-Dose Trial of Gadolinium Texaphyrin (Gd-Tex), a Tumor Selective Radiation Sensitizer Detectable by Magnetic Resonance Imaging," Clinical Cancer Research, 5(4):739-745.

(56) References Cited

OTHER PUBLICATIONS

Sandler, (1961). "Clinical evaluation of propatylnitrate in angina pectoris," British Medical Journal, 2(5269):1741-1744.
Sauder, (1989). "A Preliminary Trial of the Programmable Implantable Medication System for Insulin Delivery," The New England Journal of Medicine, 321(9):574-579.
Sausville et al., (2006). "Contributions of Human Tumor Xenografts to Anticancer Development," Cancer Research, 66(7):3351-3354.
Sefton, (1987). "Implantable Pumps," CRC Grit. Rev. Biomed. Eng., 14(3):201-237.
Shokeir, (2004). "Squamous Cell Carcinoma of the Bladder: pathology, diagnosis and treatment," BJU International, 93:216-220.
Sikder et al., (2004). "1,3,3-Trinitroazetidine (TNAZ), a melt-cast explosive: synthesis, characterization and thermal behavior," Journal of Hazardous Materials, 113:35-43.
Simpson et al., (1994). "Characterization of TNAZ," UCRL-ID-119672, Lawrence Livermore National Laboratory, 15 pages.
Smolen et al., (1984). "Chapter 7: Controlled Drug Bioavailability," Drug Product Design and Performance, pp. 203-237.
Stamler et al., (2002). "Inhaled ethyl nitrite gas for persistent pulmonary hypertension in infants," The Lancet, 360(9350):2077.
Straessler et al., (2012). "Development of a Safe and Efficient Two-Step Synthesis for Preparing 1- Bromoacetyl-3,3-dinitroazetidine, a Novel Clinical Anticancer Candidate," Organic Process Research & Development, 16:512-517.
Stratford et al., (1998). "Bioreductive drugs into the next millennium," Anti-Cancer Drug Design, 13:519-528.
Treat et al., (1988). "Liposome Encapsulated Doxorubicin: Preliminary Results of Phase I and Phase II Trials," Liposomes in the Therapy of Infectious Diseases and Cancer, Proceedings of the Ciba-Geigy-Squibb-UCLA Colloquium, pp. 353-365.
Verma et al., (2000). "Osmotically Controlled Oral Drug Delivery," Drug Dev. Ind. Pharm., 26(7):695-708.
Watt et al., (1998). "TNAZ Based Melt-Cast Explosives: Technology Review and AMRL Research Directions," Weapons Systems Division, Aeronautical and Maritime Research Laboratory, Melbourne, Australia. Report DSTO-TR-0702, 37 pages.
West, (1988). "Solid State Chemistry and its Applications," Wiley, New York, pp. 358 and 365.
Written Opinion of the International Searching Authority for PCT/US2006/031722 dated May 29, 2007, 3 pages.
Written Opinion of the International Searching Authority for PCT/US2006/031917 dated Jul. 20, 2007, 3 pages.
Written Opinion of the International Searching Authority for PCT/US2011/021500 dated Aug. 9, 2012, 4 pages.
Wu et al., (2011). "Reactive impurities in excipients: profiling, identification and mitigation of drug-excipient incompatibility," in AAPS PharmSciTech., 12(4):1248-1263.
Yarmukhamedov et al., (2005). "One-step synthesis of substituted 3,5-dinitropiperidines and 1,5-dinitro-3,7-diazabicyclo(3.3.1)nonanes from 1,3-dinitropropanes," Russian Chemical Bulletin, International Edition, 54(2):414-420.
Yen et al., (2004). "18F-FDG Uptake in Squamous Cell Carcinoma of the Cervix is Correlated with Glucose Transporter 1 Expression," The Journal of Nuclear Medicine, 45(1):22-29.
Zhang et al., (1998). caplus an 1998:460439, RN 211429-18-4, 1 page.
Brezezniak et al., (2016). "RRx-001-Induced Tumor Necrosis and Immune Cell Infiltration in an EGFR Mutation-Positive NSCLC with Resistance to EGFR Tyrosine Kinase Inhibitors: A Case Report," Case Rep Oncol., 9:45-50.
Cabrales et al., (2016). "A look inside the mechanistic black box: Are red blood cells the critical effectors of RRx-001 cytotoxicity?" Medical Oncology, 33(7):63, 7 Pages. Abstract Only.
Carter et al., (2016). "Partial response to carboplatin in an RRx-001 pretreated patient with EGFR-inhibitor-resistance and T790M-negative NSCLC," Respir. Aged Case Rep., 18:62-65.
Chawla et al., (2004). "Challenges in Polymorphism of Pharmaceuticals," CRIPS, 5(1):12-15.
ClinicalTrials.gov, (2015). "NCT02489903: An Open-label, Three Stage, Three Arm Pilot Study of RRx-001 for Second Line or Greater Small Cell Lung Cancer, Third Line or Greater Non-Small Lung Cancer, and Second Line or Greater High Grade Neuroendocrine Tumors Prior to Re-administration of Platinum Based Doublet Regimens (Triple Threat)", Available from the Internet, <https://clinicaltrials.gov/ct2/history/NCT02489903?V_1=View#StudyPageTop>, 12 pages.
ClinicalTrials.gov, (2015). "NCT01359982: Safety and Pharmacokinetic Study of RRx-001 in Cancer Subjects (DINAMIC)," available online at <https://clinicaltrials.gov/ct2/show/NCT02096354?term=RRx-001&draw=1&rank=11 >, 7 pages.
ClinicalTrials.gov, (2016). "NCT02096341: A Phase 1 Pilot Study of the Subcutaneous (s.c.) Route to Facilitate the Administration of RRx-001," available online at <https://clinicaltrials.gov/ct2/show/NCT02096341?term=RRx-001&draw=1&rank=3>, 5 pages.
ClinicalTrials.gov, (2018). "NCT03515538: Safety and Efficacy of RRx-001 in the Attenuation of Oral Mucositis in Patients Receiving Chemoradiation for the Treatment of Oral Cancers (PREVLAR)," retrieved from the internet <https://clinicaltrials.gov/ct2/show/NCT03515538>, 11 pages.
ClinicalTrials.gov, (2019). "NCT02489903: RRX-001 in Lung Cancer, Ovarian Cancer and Neuroendocrine Tumors Prior to Re-administration of Platinum Based Doublet Regimens (Quadruple Threat)", available online at <https://clinicaltrials.gov/ct2/history/NCT02489903?V_1=View#StudyPageTop>, 10 pages.
ClinicalTrials.gov, (2019). "NCT02452970: RRx-001 in Second Line Treatment of Advanced Cholangiocarcinoma Prior to Readministration of First-Line Therapy (EPIC)," available online at <https://clinicaltrials.gov/ct2/show/NCT02452970?term=RRx-001&draw=3&rank=1>, 6 pages.
ClinicalTrials.gov, (2019). "NCT02518958: A Phase I, Open-Label, Multiple Ascending Dose Study of RRx-001 and Nivolumab (PRIMETIME)," available online at <https://clinicaltrials.gov/ct2/show/NCT02518958?term=RRx-001&draw=1&rank=7>, 6 pages.
ClinicalTrials.gov, (2020). "NCT02871843: Phase 1 Two Part Dose Escalation Trial of RRx-001 + Radiation + Temozolomide and RRx-001 + Temozolomide Post-RT in Newly Diagnosed Glioblastoma and Anaplastic Gliomas (G-FORCE-1)," available online at <https://clinicaltrials.gov/ct2/show/NCT02871843>, 8 pages.
ClinicalTrials.gov, (2021). "NCT02215512: Dose-Escalation Study of RRx-001 in Combination With Whole Brain Radiation in Subjects With Brain Metastases (Brainstorm)," available online at <https://clinicaltrials.gov/ct2/show/NCT02215512>, 7 pages.
ClinicalTrials.gov, (2021). "NCT03699956: RRx-001 Sequentially With a Platinum Doublet or a Platinum Doublet in Third-Line or Beyond in Patients With Small Cell Lung Cancer (Replatinum)," available online at <https://clinicaltrials.gov/ct2/show/NCT03699956?term=RRx-001&draw=1&rank=5>, 8 pages.
ClinicalTrials.gov, (2022). "NCT02096354: A Phase 2 Randomized, Open-Label Study of RRx-001 vs Regorafenib in Subjects With Metastatic Colorectal Cancer (Rocket)," available online at <https://clinicaltrials.gov/ct2/show/NCT02096354?term=RRx-001&draw=1&rank=8>, 8 pages.
ClinicalTrials.gov, (2022). "NCT02801097: RRx-001 in Combination With Irinotecan in Metastatic or Advanced Cancer (Payload) (Payload)," available online at <https://clinicaltrials.gov/ct2/show/NCT02801097?term=RRx-001&draw=1 &rank=6>, 6 pages.
ClinicalTrials.gov, (2022). "NCT02871843: RRx-001 + Radiation + Temozolomide in Newly Diagnosed Glioblastoma and Anaplastic Gliomas (G-Force-1)," available online at <https://clinicaltrials.gov/ct2/show/NCT02096354?term=RRx-001&draw=1&rank=9>, 8 pages.
ClinicalTrials.gov, (2022). "NCT04525014: RRx-001 Given With Irinotecan and Temozolomide for Pediatric Patients With Recurrent or Progressive Malignant Solid and Central Nervous System Tumors (Pirate)," available online at <https://clinicaltrials.gov/ct2/show/NCT02096341?term=RRx-001&draw=1&rank=3>, 10 pages.
Dave, (1997), caplus an 1997:67373, RN 179894-08-7,1 page.
Dorman, (2000). "Fulminant babesiosis treated with clindamycin, quinine, and whole-blood exchange transfusion," Transfusion, 40(3):375-80.
Drumond et al., (2013). "Transmissible Venereal Tumor treated with Autohemotherapy," Acta Scientiae Veterinariae, 41:1107, 4 pages.

(56) References Cited

OTHER PUBLICATIONS

European Supplementary Search Report for European Patent Application No. EP12839088.7, published Apr. 28, 2015, 4 pages.
Fareed et al., (2000). "An update on herapins at the beginning of the new millennium," Semin Thromb Hemost., 26(Suppl 1):5-21.
Final Office Action received for U.S. Appl. No. 13/655,618 dated Jun. 12, 2014, 6 pages.
Final Office Action received for U.S. Appl. No. 13/655,618 dated Sep. 11, 2013, 4 pages.
Final Office Action received for U.S. Appl. No. 14/965,062 dated Feb. 6, 2017, 6 pages.
Final Office Action received for U.S. Appl. No. 16/284,035 dated May 26, 2022, 28 pages.
Final Office Action received for U.S. Appl. No. 16/284,035 dated Nov. 15, 2021, 24 pages.
Fitch et al., (2013). "Abstract WRM 267: High resolution MS proves that the developmental cancer drug, RRx-001, alkylates the hemoglobin beta chain," 44th Western Regional Meeting of the American Chemical Society, available online at <http://www.acswrm.org/wrm2013/files/Abstracts_SaturdayAM.pdf>, 1 page.
Grisham, (2017). "Pumped Up: Implanted Chemotherapy Device Improves Survival when Colorectal Cancer Spreads to the Liver," available online at <https://www.mskcc.org/news/pumped-implanted-chemotherapy-device-improves-survival-when-colorectal-cancer-spreads-liver>, 5 pages.
Hiskey et al., (1999). caplus an 1999:411860, RN 236102-58-2, 1 page.
Hong et al., (2008). Combining Targeted Therapies, Targeted Cancer Therapy, p. 362, 2 pages.
Ignarro, (2000). "Nitric Oxide Biology and Pathology," Academic Press, pp. 5, 895, and 908.
International Preliminary Report on Patentability for PCT/US2019/012696 dated Jul. 14, 2020, 8 pages.
International Preliminary Report on Patentability for PCT/US2019/012701 dated Jul. 14, 2020, 8 pages.
International Search Report and Written Opinion for PCT/US2017/012948 dated Mar. 28, 2017, 8 pages.
International Search Report and Written Opinion for PCT/US2017/056454 dated Feb. 6, 2018, 12 pages.
International Search Report and Written Opinion for PCT/US2018/041138 dated Oct. 5, 2018, 9 pages.
International Search Report and Written Opinion for PCT/US2019/012696 dated Sep. 6, 2019, 12 pages.
International Search Report and Written Opinion for PCT/US2019/012701 dated Sep. 4, 2019, 12 pages.
Jia, (2008). "A Guide to Pass the National Licensed Pharmacist Examination in Medicinal Chemistry," pp. 4-11, 9 pages. English abstract.
Kamran et al., (2016). "Radioprotective Agents: Strategies and Translational Advances," Medicinal Research Reviews, 36(3):461-493, 33 pages.
Kim et al., (2016). "Whole Brain Radiotherapy and RRx-001: Two Partial Responses in Radioresistant Melanoma Brain Metastases from a Phase 1/11 Clinical Trial: A TITE-CRM Phase 1/11 Clinical Trial," Translational Oncology, 9(2):108-113.
Li et al., (2006). caplus an 2006:150006, RN 179894-08-7, 1 page.
Li, (2014). "Nursing Comprehensive Skills Training," China Press of Traditional Chinese Medicine, 3 pages. English abstract.
Merck & Co., Inc., (2008). "TEMODAR Prescribing Information," 17 pages.
Miller et al., (2015). "CD47 Receptor Globally Regulates Metabolic Pathways That Control Resistance to Ionizing Radiation," J. Biol. Chem., 290:24858-24874.
Nih, (2018). "Vascular Tumor," available online at <htgs://www.cancer.gov/gublications/dictionaries/cancer-terms/def/vascular-tumor>, 1 page.
Ning et al., (2002). "The Antiangiogenic Agents SU5416 and SU6668 Increase the Antitumor Effects of Fractionated Irradiation," Radiation Research, 157:5-51.
Ning et al., (2012). "Dinitroazetidines Are a Novel class of Anticancer Agents and Hypoxia-Activated Radiation Sensitizers Developed from Highly Energetic Materials," Cancer Res., 72:2600-2608.
Ning et al., (2015). "Nrf2 activity as a potential biomarker for the pan-epigenetic anticancer agent, RRx-001," Oncotarget, 6(25):21547-21556.
Oberoi et al., (2013). "Nanocarriers for delivery of platinum anticancer drugs," Advanced Drug Delivery Reviews, 65(13):1667-1685.
Office Action received for U.S. Appl. No. 12/397,651 dated Feb. 11, 2011, 10 pages.
Office Action received for U.S. Appl. No. 12/397,651 dated Feb. 23, 2012, 8 pages.
Office Action received for U.S. Appl. No. 13/655,618 dated Feb. 25, 2014, 6 pages.
Office Action received for U.S. Appl. No. 13/655,618 dated May 2, 2013, 9 pages.
Office Action received for U.S. Appl. No. 14/849,783 dated Jan. 15, 2016, 5 pages.
Office Action received for U.S. Appl. No. 14/965,062 dated Aug. 11, 2016, 10 pages.
Office Action received for U.S. Appl. No. 14/965,062 dated Dec. 18, 2017, 8 pages.
Office Action received for U.S. Appl. No. 15/298,735 dated Aug. 30, 2018, 9 pages.
Office Action received for U.S. Appl. No. 15/669,403 dated Sep. 14, 2018, 9 pages.
Office Action received for U.S. Appl. No. 15/989,862 dated Feb. 8, 2019, 6 pages.
Office Action received for U.S. Appl. No. 16/284,035 dated Apr. 13, 2021, 17 pages.
Office Action received for U.S. Appl. No. 16/353,047 dated Aug. 31, 2020, 7 pages.
Office Action received for U.S. Appl. No. 16/712,148 dated Oct. 7, 2020, 7 pages.
Office Action received for U.S. Appl. No. 16/960,443 dated May 28, 2021, 25 pages.
Oronsky et al., (2017). "RRx-001: a systemically non-toxic M2-to-M1 macrophage stimulating and prosensitizing agent in Phase II clinical trials", Expert Opinion on investigational Drugs, 26(1):109-119.
Oronsky et al., (2015). "A Review of Two Promising Radiosensitizers in Brain Metastases: Rrx-001 and 2-Deoxyqlucose," J. Cancer Sci. Ther., 7:137-141.
Oronsky et al., (2016). "RRx-001, A novel dinitroazetidine radiosensitizer," Invest. New Drugs, 34(3):371-377.
Pinkel, (1958). "The use of body surface area as a criterion of drug dosage in cancer chemotherapy," Cancer Research, 18:853-856.
Rafikova et al., (2004). "Control of Plasma Nitric Oxide Bioactivity by Perfluorocarbons Physiological Mechanisms and Clinical Implications," Circulation., 110:3573-3580.
Reid et al., (2014). "Two Case Reports of Resensitization to Previous Chemotherapy with the Novel Hypoxia-Activated Hypomethylating Anticancer Agent RRx-001 in Metastatic Colorectal Cancer Patients," Case Rep. Oncol., 7(1):79-85.
Reid et al., (2015). "Safety and activity of RRx-001 in patients with advanced cancer: a first-in-human, open-label, dose-escalation phase 1 study," Lancet Oncol, 16:1133-42.
Rupnow et al., (1998). "p53 Mediates Apoptosis Induced by C-Myc Activation in Hypoxic or Gamma Irradiated Fibroblasts," Cell Death and Differentiation, 7:141-147.
Scicinski et al., (2012). "Preclinical Evaluation of the Metabolism and Disposition of RRx-001, a Novel Investigative Anticancer Agent", Drug Metabolism and Disposition, 40(9):1810-1816.
Scicinski et al., (2014). "Development of methods for the bioanalysis of RRx-001 and metabolites", Bioanalysis, 6(7):947-956.
Scicinski et al., (2015). "NO to cancer: The complex and multifaceted role of nitric oxide and the epigenetic nitric oxide donor, RRx-001," Redox Biology, 6:1-8.
Thomas, (2016). "Mucositis in Cancer Patients: A Review," available online at <https://www.uspharmacist.com/article/mucositis-in-cancer-patients-a-review#:~:text=Mucositis%20is%20a%20common%

(56) References Cited

OTHER PUBLICATIONS

20complication,the%20gastrointestinga%20(GI)%20tract.&text=Although%20mucositis%20can%20occur%20anywhere,site%22is%20the%20oral%20cavity>, 10 pages.

Watt et al., (2000). "Evaluation of 1,3,3-Trinitrozaetidine (TNAZ)—A High Performance Melt-Castable Explosive," Weapons Systems Division, Aeronautical and Maritime Research Laboratory, Melbourne, Australia. Report No. DSTO-TR-1000, 34 pages.

Wilson et al., (1998). "Radiation-activated prodrugs as hypoxia-selective cytotoxins: model studies with nitroarylmethyl quaternary salts," Anti-Cancer Drug Design, 13:663-685.

Yamaguchi et al., (2001). "Photodynamic Therapy with Motexafin Lutetium (Lu-Tex) Reduces Experimental Graft Coronary Artery Disease," Transplantation, 71(11):1526-1532.

You, (2011). "代动力学性质, 不但增加了血药浓度, 且延长作用时间," Medicinal Chemistry, pp. 585-588, 5 pages. English abstract.

Zervoudakis et al., (2017). "Treatment Options in Colorectal Liver Metastases: Hepatic Arterial Infusion," Visc Med, 33:47-53.

Zhu et al., (2017). "Amino-functionalized nano-vesicles for enhanced anticancer efficacy and reduced myelotoxicity of carboplatin," Colloids and Surfaces, B, Biointerfaces, 157:56-64.

Zuo, (2015). "Chapter 16: Cell Death," Medical Cell Biology, pp. 230-235, 7 pages. English abstract.

Office Action received for U.S. Appl. No. 17/223,422 dated Sep. 19, 2022, 7 pages.

\* cited by examiner

METHODS AND COMPOSITIONS COMPRISING A NITRITE-REDUCTASE PROMOTER FOR TREATMENT OF MEDICAL DISORDERS AND PRESERVATION OF BLOOD PRODUCTS

CROSS REFERENCE TO RELATED APPLICATIONS

This application is a continuation patent application under 35 U.S.C. § 120 of U.S. patent application Ser. No. 14/349,010, filed on Apr. 1, 2014, which is a national stage entry of International Application No. PCT/US2012/058964, filed on Oct. 5, 2012, which claims the benefit of and priority to U.S. Provisional Patent Application No. 61/544,375, filed on Oct. 7, 2011, the contents of each of which are hereby incorporated by reference herein, in their entirety.

FIELD OF THE INVENTION

The invention provides methods, compositions, and medical kits comprising a nitrite-reductase promoter, such as an allosteric modulator of hemoglobin, for use in treating medical disorders and preservation of blood products.

BACKGROUND

Cancer, cardiovascular disorders, ischemic conditions, and bacterial infections remain a significant health problem for people in many developed countries. The need for cancer treatments, for example, has prompted the United States National Cancer Institute to coordinate large-scale research efforts, impacting over six hundred universities, hospitals, and cancer centers located in the United States and over twenty foreign countries. Past research efforts have lead to significant advances in the detection, evaluation, and treatment of cancer, cardiovascular disorders, ischemic conditions, and bacterial infections. However, despite these developments, these medical conditions remain significant health problems for many patients.

According to current statistics, cancer is a leading cause of death worldwide. Approximately one million people are diagnosed with cancer each year in the United States, and approximately half a million cancer patients die annually despite the significant progress made during the last decade in the diagnosis and treatment of cancer. Leading types of cancer that affect a substantial number of patients include colon cancer, breast cancer, prostate cancer, and skin cancer. The need exists for improved drugs and therapeutic methods for treating cancer.

Cardiovascular disorders that affect a significant number of patients include atherosclerosis, arteriosclerosis, myocardial infarction, angina pectoris, cardiac failure, embolism, thrombus, and hypertension. Hypertension is particularly prevalent, with some estimates suggesting approximately twenty-five percent of the adult population worldwide being hypertensive. Although dietary and lifestyle changes may reduce blood pressure, medications are often necessary to reduce blood pressure to an acceptable level in hypertensive patients. Examples of anti-hypertensive drugs include angiotensin-converting enzyme (ACE) inhibitors, alpha blockers, angiotensin II receptor antagonists, beta blockers, calcium channel blockers, diuretics, and direct renin inhibitors. Without treatment, hypertensive patients can have a significantly higher risk of cardiovascular disorders and a reduced life expectancy. The need exists for improved drugs and therapeutic methods for treating cardiovascular disorders.

Also, current therapies for treating bacterial infections are insufficient because many prominent, infection-causing bacterial strains have developed resistance to current antibiotics. Antibiotic resistance can result in severe adverse outcomes, such as increased mortality, morbidity, and medical care costs for patients suffering from common infections. Infections due to organisms such as methicillin-resistant *Staphylococcus aureus* (MRSA) occur with increasing frequency in hospitals and are becoming more difficult to treat with conventional antibiotics. For example, a recently discovered strain of *Staphylococcus aureus* was resistant to treatment with vancomycin, a drug generally regarded as a last line of defense against certain infections. Thus, infection by antibiotic-resistant organisms is a significant health threat for which new methods and compositions for treatment are needed.

Another important medical therapy is blood transfusions. Blood transfusions are a ubiquitous part of healthcare delivery. In the United States (US), someone needs blood about every two seconds and according to the 2009 National Blood Collection and Utilization Survey Report (NBCUS), a total of 15 million units of blood were transfused. Currently, blood products can be stored only for short periods of time. Thus, one unmet medical need is for compositions and methods capable of extending the storage life of blood products.

Accordingly, there is need for new therapeutic methods and compositions for extending the storage life of blood products, enhancing the benefits of blood transfusions, and treating disorders such as cancer, cardiovascular disorders, ischemic conditions, and bacterial infections. The present invention addresses these needs and provides other related advantages.

SUMMARY

The invention provides methods, compositions, and medical kits comprising a nitrite-reductase promoter, such as an allosteric modulator of hemoglobin, for use in treating medical disorders and preservation of blood products. For example, in certain aspects, the invention provides methods, compositions, and medical kits comprising an inorganic nitrite salt and a nitrite-reductase promoter, such as an allosteric modulator of hemoglobin, for use in treating medical disorders, such as cancer, cardiovascular disorders, ischemic conditions, hemolytic conditions, and bacterial infections. In other aspects, the invention provides agents (e.g., allosteric modulator of hemoglobin) for treating a patient suffering from reduced blood volume (e.g., a patient suffering from hemorrhagic shock), performing a blood transfusion to a patient, treating a patient suffering from anemia, and preserving an isolated blood product. Various aspects and embodiments of the invention are described in further detail below.

One aspect of the invention provides a method of treating or preventing a disorder selected from the group consisting of cancer, a cardiovascular disorder, an ischemic condition, a hemolytic condition, or a bacterial infection. The method comprises administering to a patient in need thereof a therapeutically effective amount of (i) an inorganic nitrite salt, and (ii) an allosteric modulator of hemoglobin that promotes nitrite reductase activity. In certain embodiments, the allosteric modulator of hemoglobin is a compound embraced by Formula, I or Formula II, wherein Formula I is represented by:

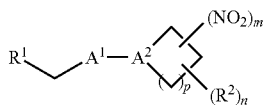

or a pharmaceutically acceptable salt or solvate thereof, wherein the variables are as defined in the detailed description, and Formula II is represented by:

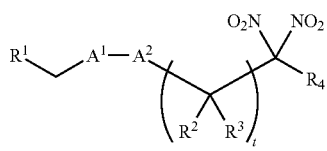

or a pharmaceutically acceptable salt or solvate thereof, wherein the variables are as defined in the detailed description.

Another aspect of the invention provides a method of increasing the amount of nitric oxide produced by hemoglobin in a patient. The method comprises administering to a patient in need thereof a therapeutically effective amount of (i) an inorganic nitrite salt, and (ii) an allosteric modulator of hemoglobin that promotes nitrite reductase activity.

Another aspect of the invention provides a pharmaceutical composition comprising (i) an inorganic nitrite salt, and (ii) an allosteric modulator of hemoglobin that promotes nitrite reductase activity. Still another aspect of the invention provides a kit for treating a medical disorder. The kit comprises (i) an inorganic nitrite salt, (ii) an allosteric modulator of hemoglobin, and (iii) instructions for using the kit to treat a medical disorder.

Another aspect of the invention provides a method of treating a patient suffering from reduced blood volume. The method comprises administering to a patient in need thereof a blood product by injection and a therapeutic agent selected from the group consisting of an organonitro compound of Formula I, organonitro compound of Formula II, hemoglobin conjugate of Formula III, hemoglobin conjugate of Formula IV, and an erythrocyte cell that has been exposed to an organonitro compound of Formula I or II; wherein Formula I is represented by:

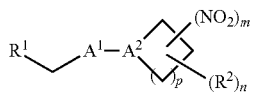

or a pharmaceutically acceptable salt or solvate thereof wherein the variables are as defined in the detailed description, Formula II is represented by:

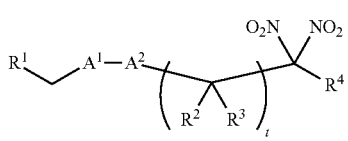

or a pharmaceutically acceptable salt or solvate thereof wherein, the variables are as defined in the detailed description, Formula III is represented by:

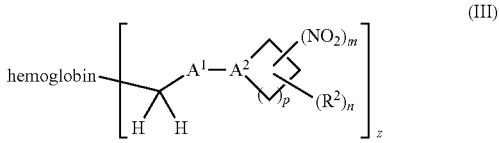

or a pharmaceutically acceptable salt or solvate thereof, wherein the variables are as defined in the detailed description, and Formula IV is represented by:

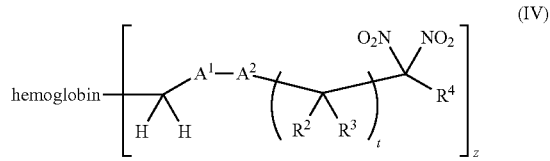

or a pharmaceutically acceptable salt or solvate thereof wherein the variables are as defined in the detailed description.

Another aspect of the invention provides a method of performing a blood transfusion to a patient. The method comprises administering to a patient in need thereof a blood product by injection and a therapeutic agent selected from the group consisting of an organonitro compound of Formula organonitro compound of Formula II, hemoglobin conjugate of Formula, III, hemoglobin conjugate of Formula IV, and an erythrocyte cell that has been exposed to an organonitro compound of Formula I or II, wherein Formula I is represented by:

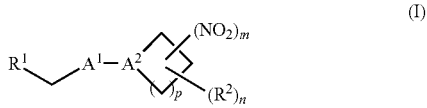

or a pharmaceutically acceptable salt or solvate thereof, wherein the variables are as defined in the detailed description. Formula I is represented by:

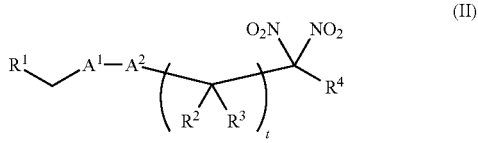

or a pharmaceutically acceptable salt or solvate thereof: wherein the variables are as defined in the detailed description, Formula III is represented by:

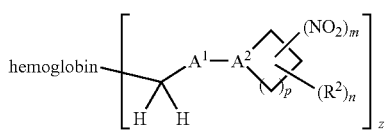

(III)

or a pharmaceutically acceptable salt or solvate thereof, wherein the variables are as defined in the detailed description, and Formula IV is represented by:

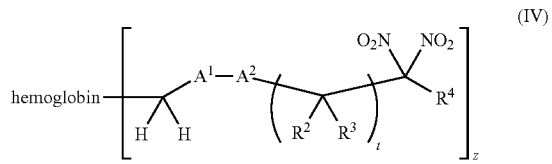

(IV)

or a pharmaceutically acceptable salt or solvate thereof, wherein the variables are as defined in the detailed description.

Another aspect of the invention provides a method of treating a patient suffering from anemia. The method comprises administering to a patient in need thereof a therapeutic agent selected from the group consisting of an organonitro compound of Formula I, organonitro compound of Formula II, hemoglobin conjugate of Formula III, hemoglobin conjugate of Formula IV, and an erythrocyte cell that has been exposed to an organonitro compound of Formula I or II; wherein Formula I is represented by:

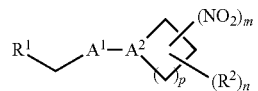

(I)

or a pharmaceutically acceptable salt or solvate thereof wherein the variables are as defined in the detailed description, Formula II is represented by:

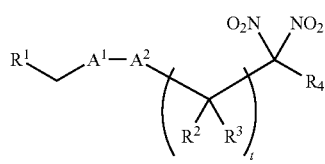

(II)

or a pharmaceutically acceptable salt or solvate thereof, wherein the variables are as defined in the detailed description, Formula III is represented by:

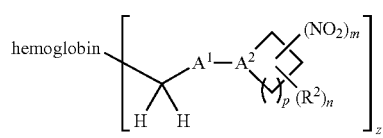

(III)

or a pharmaceutically acceptable salt or solvate thereof, wherein the variables are as defined in the detailed description, and Formula IV is represented by:

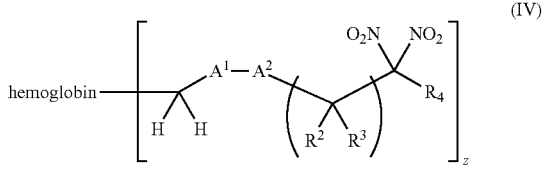

(IV)

or a pharmaceutically acceptable salt or solvate thereof, wherein the variables are as defined in the detailed description.

Another aspect of the invention provides a method of preserving an isolated blood product. The method comprises exposing the isolated blood product to an agent selected from the group consisting of an organonitro compound of Formula I, organonitro compound of Formula II, hemoglobin conjugate of Formula III, hemoglobin conjugate of Formula IV, and an erythrocyte cell that has been exposed to an organonitro compound of Formula I or II, wherein Formula I is represented by:

(I)

or a pharmaceutically acceptable salt or solvate thereof, wherein the variables are as defined in the detailed description, Formula II is represented by:

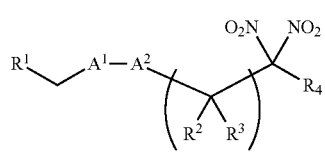

(II)

or a pharmaceutically acceptable salt or solvate thereof: wherein the variables are as defined in the detailed description, Formula III is represented by:

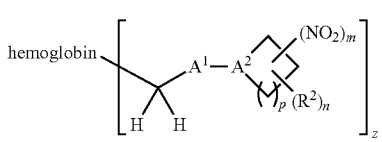

(III)

or a pharmaceutically acceptable salt or solvate thereof, wherein the variables are as defined in the detailed description, and Formula IV is represented by:

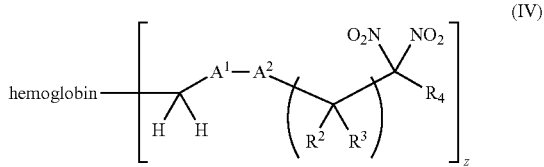

(IV)

or a pharmaceutically acceptable salt or solvate thereof, wherein the variables are as defined in the detailed description.

Another aspect of the invention provides an isolated blood product composition. The composition comprises (i) a blood product, and (ii) an agent selected from the group consisting of an organonitro compound of Formula I, organonitro compound of Formula II, hemoglobin conjugate of Formula III, hemoglobin conjugate of Formula IV, and an erythrocyte cell that has been exposed to an organonitro compound of Formula I or II; wherein Formula I is represented by:

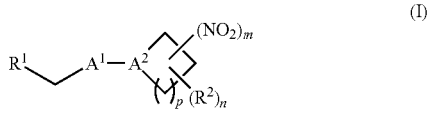

(I)

or a pharmaceutically acceptable salt or solvate thereof wherein the variables are as defined in the detailed description, Formula II is represented by:

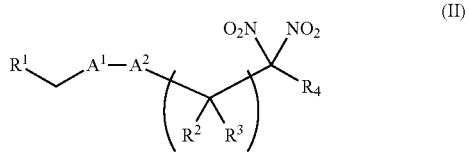

(II)

or a pharmaceutically acceptable salt or solvate thereof, wherein the variables are as defined in the detailed description, Formula III is represented by:

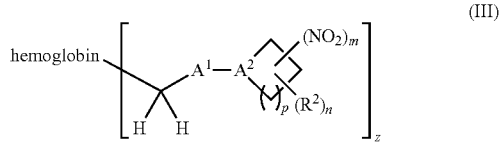

(III)

or a pharmaceutically acceptable salt or solvate thereof, wherein the variables are as defined in the detailed description, and Formula IV is represented by:

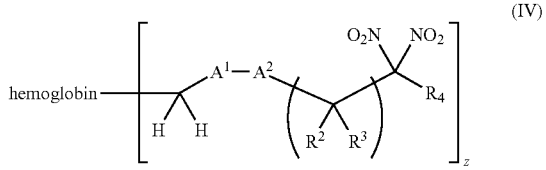

(IV)

or a pharmaceutically acceptable salt or solvate thereof wherein the variables are as defined in the detailed description.

Another aspect of the invention provides an isolated hemoglobin conjugate represented by Formula III or IV:

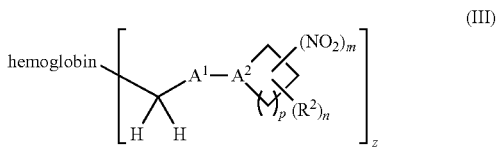

(III)

or a pharmaceutically acceptable salt or solvate thereof, wherein the variables are as defined in the detailed description, and Formula IV is represented by:

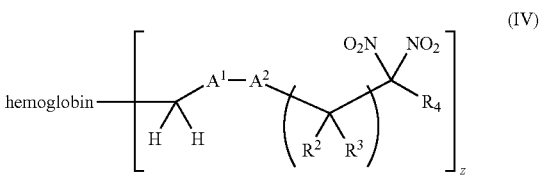

(IV)

or a pharmaceutically acceptable salt or solvate thereof, wherein the variables are as defined in the detailed description Another aspect of the invention provides pharmaceutical compositions comprising a pharmaceutically acceptable carrier and a hemoglobin conjugate as defined in the detailed description, such as a hemoglobin conjugate of Formula III or IV.

DETAILED DESCRIPTION OF THE INVENTION

Figure 1:
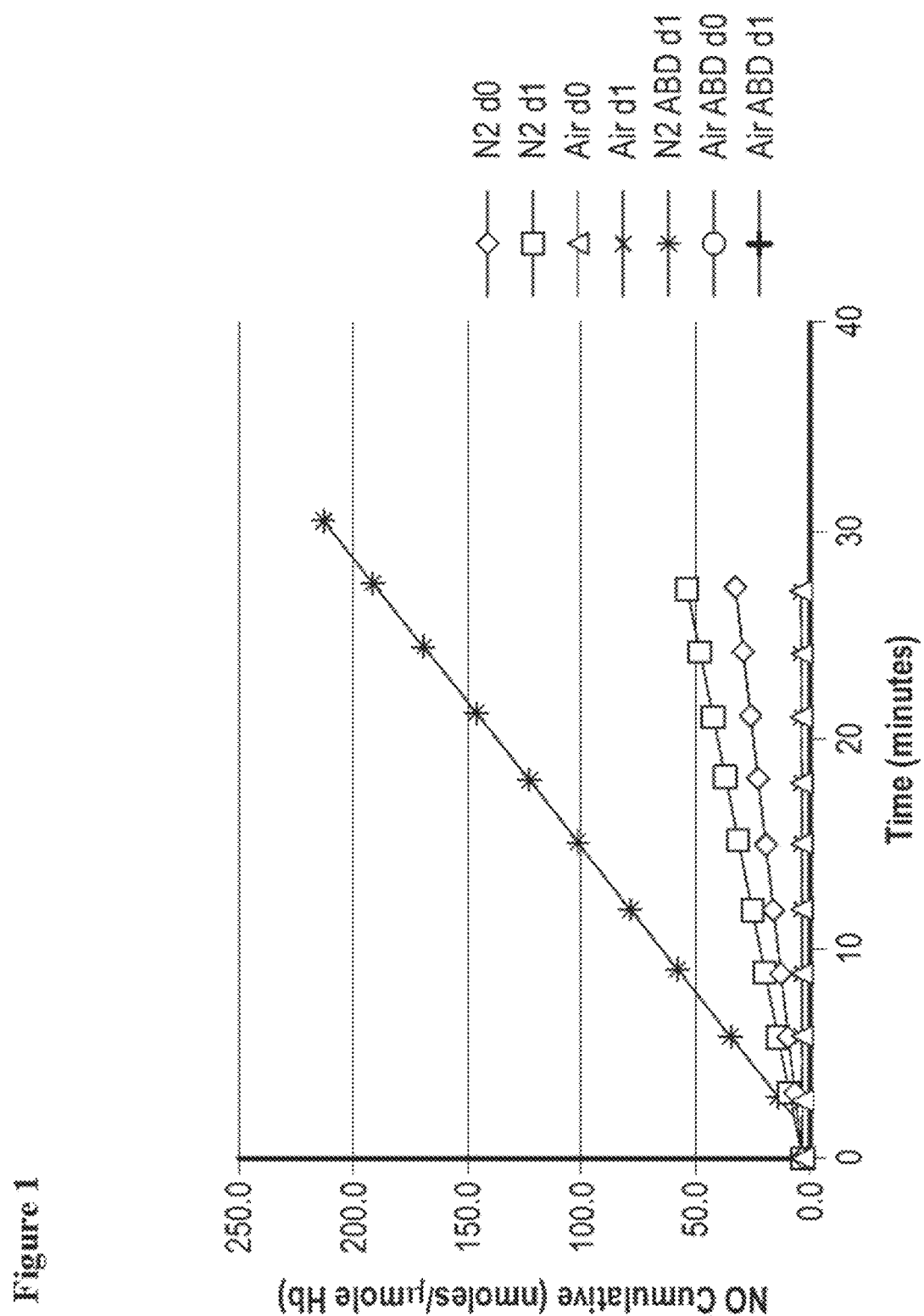
FIG. 1 is a graph showing the cumulative amount of nitric oxide formed from a blood sample over a thirty-minute time period for multiple experiments (experimental conditions varied include using air atmosphere, $N_2$ atmosphere, and/or the presence or absence of ABDNAZ), as described in Example 1.
Figure 2:
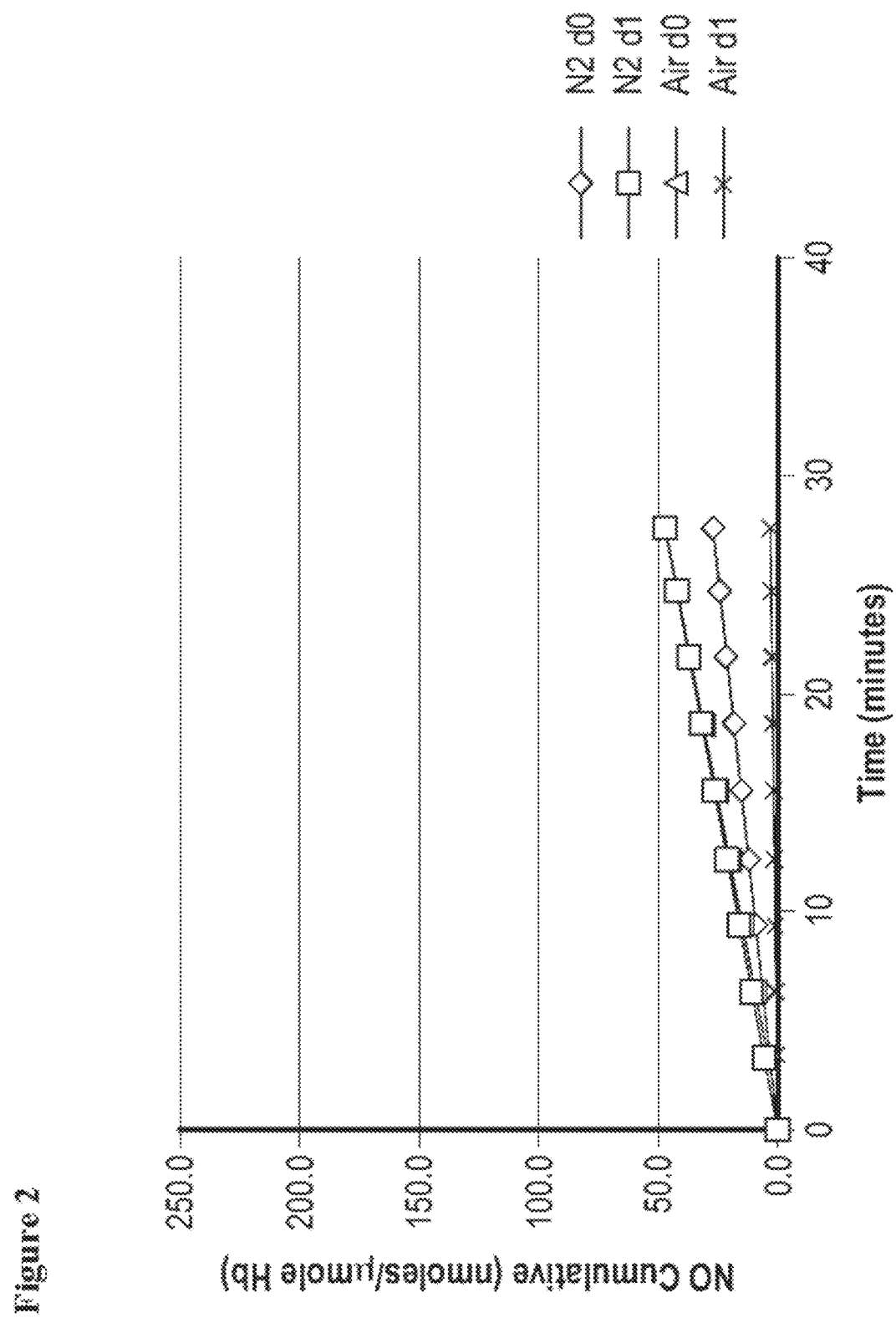
FIG. 2 is a graph showing the cumulative amount of nitric oxide formed from a blood sample over a thirty-minute time period under an air atmosphere or $N_2$ atmosphere (where d0 refers to the first experiment, and d1 refers to the second repetition of the experiment), as described in Example 1.

The invention provides methods, compositions, and medical kits comprising a nitrite-reductase promoter, such as an allosteric modulator of hemoglobin, for use in treating medical disorders and preservation of blood products. For example, in certain aspects, the invention provides methods, compositions, and medical kits comprising an inorganic nitrite salt and a nitrite-reductase promoter, such as an allosteric modulator of hemoglobin, for use in treating medical disorders, such as cancer, cardiovascular disorders, ischemic conditions, hemolytic conditions, and bacterial infections. In other aspects, the invention provides agents (e.g., allosteric modulator of hemoglobin) for treating a patient suffering from reduced blood volume (e.g., a patient suffering from hemorrhagic shock), performing a blood transfusion to a patient, treating a patient suffering from anemia, and preserving an isolated blood product. The practice of the present invention employs, unless otherwise indicated, conventional techniques of organic chemistry, pharmacology, cell biology, and biochemistry. Such techniques are explained in the literature, such as in "Comprehensive Organic Synthesis" (B. M. Trost & I. Fleming, eds., 1991-1992); "Current protocols in molecular biology" (F. M. Ausubel et al., eds., 1987, and periodic updates); and "Current protocols in immunology" (J. E. Coligan et al., eds., 1991), each of which is herein incorporated by reference in its entirety. Various aspects of the invention are set forth below in sections; however, aspects of the invention described in one particular section are not to be limited to any particular section.

I. Definitions

To facilitate an understanding of the present invention, a number of terms and phrases are defined below.

The terms "a" and "an" as used herein mean "one or more" and include the plural unless the context is inappropriate.

The term "blood product" means (i) whole blood, or (ii) component(s) isolated from whole.

The term "alkyl" as used herein refers to a saturated straight or branched hydrocarbon, such as a straight or branched group of 1-12, 1-10, or 1-6 carbon atoms, referred to herein as $C_1$-$C_{12}$alkyl, $C_1$-$C_{10}$alkyl, and $C_1$-$C_6$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "haloalkyl" refers to an alkyl group that is substituted with at least one halogen. For example, —CH$_2$F, —CHF$_2$, —CF$_3$, —CH$_2$—CF$_3$, —CF$_2$CF$_3$, and the like.

The term "aralkyl" refers to an alkyl group substituted with an aryl group.

The term "heteroaralkyl" refers to an alkyl group substituted with a heteroaryl group.

The term "aryl" is art-recognized and refers to a carbocyclic aromatic group. Representative aryl groups include phenyl, naphthyl, anthracenyl, and the like. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "aryl" also includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. In certain embodiments, the aryl group is not substituted, i.e., it is unsubstituted.

The "heteroaryl" is art-recognized and refers to aromatic groups that include at least one ring heteroatom. In certain instances, a heteroaryl group contains 1, 2, 3, or 4 ring heteroatoms. Representative examples of heteroaryl groups includes pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "heteroaryl" also includes polycyclic ring systems having two or more rings in which two or more carbons are common to two adjoining rings (the rings are "fused rings") wherein at least one of the rings is heteroaromatic and, e.g., the other ring(s) may be cycloalkyls, cycloalkenyls, cycloalkynyls, and/or aryls. In certain embodiments, the heteroaryl is a bicyclic aromatic ring in which both ring of the bicyclic system are heteroaromatic. In certain embodiments, the heteroaryl group is not substituted, i.e., it is unsubstituted.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

As used herein, the term "heterocyclic" represents, for example, an aromatic or nonaromatic ring containing one or more heteroatoms. The heteroatoms can be the same or different from each other. Examples of heteroatoms include, but are not limited to nitrogen, oxygen and sulfur. Aromatic and nonaromatic heterocyclic rings are well-known in the art. Some nonlimiting examples of aromatic heterocyclic rings include pyridine, pyrimidine, indole, purine, quinoline and isoquinoline. Nonlimiting examples of nonaromatic heterocyclic compounds include piperidine, piperazine, morpholine, pyrrolidine and pyrazolidine. Examples of oxygen containing heterocyclic rings include, but not limited to furan, oxirane, 2H-pyran, 4H-pyran, 2H-chromene, and benzofuran. Examples of sulfur-containing heterocyclic rings include, but are not limited to, thiophene, benzothiophene, and parathiazine. Examples of nitrogen containing rings include, but not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include, but are not limited to, phenothiazine, morpholine, parathiazine, oxazine, oxazole, thiazine, and thiazole. The heterocyclic ring is optionally further substituted at one or more ring positions with, for example, halogen, azide, alkyl, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like.

The terms "amine" and "amino" are art-recognized and refer to both unsubstituted and substituted amines, e.g., a moiety represented by the general formula —N(R$^{50}$)(R$^{51}$), wherein R$^{50}$ and R$^{51}$ each independently represent hydrogen, alkyl, cycloalkyl, heterocyclyl, alkenyl, aryl, aralkyl, or —(CH$_2$)$_m$—R$^{61}$; or R$^{50}$ and R$^{51}$, taken together with the N atom to which they are attached complete a heterocycle having from 4 to 8 atoms in the ring structure; R$^{61}$ represents an aryl, a cycloalkyl, a cycloalkenyl, a heterocycle or a polycycle; and m is zero or an integer in the range of 1 to 8. In embodiments, R$^{50}$ and R$^{51}$ each independently represent hydrogen, alkyl, alkenyl, or —(CH$_2$)$_m$—R$^{61}$.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and, the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R$_{61}$, where m and R$_{61}$ are described above.

The terms "ABDNAZ" and "RRx-001" are used interchangeably and refer to the compound having the following structure:

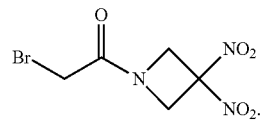

Certain compounds contained in compositions of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

As used herein, the terms "subject" and "patient" refer to organisms to be treated by the methods of the present invention. Such organisms are preferably mammals (e.g., murines, simians, equines, bovines, porcines, canines, felines, and the like), and more preferably humans. The term "non-anemic patient" refers to a patient that does not suffer from anemia.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in viva or ex viva.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "isolated" refers to material that is removed from its original environment (e.g., the natural environment if it is naturally occurring).

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

II. Combination Therapy of Inorganic Nitrite Salt and Nitrite-Reductase Promoter The invention provides combination therapy using an inorganic nitrite salt in combination with a nitrite-reductase promoter. Exemplary inorganic nitrite salts and exemplary nitrite-reductase promoters for use in the combination therapy methods, pharmaceutical compositions, and medical kits are described below. In addition, because the combination therapy may optionally comprise administration of one or more additional therapeutic agents for treatment of the designated medical disorder, exemplary additional therapeutic agents for treating exemplary medical disorders are described below.

A. Inorganic Nitrite Salts

The inorganic nitrite salt may be an alkali metal nitrite salt, an alkaline earth metal nitrite salt, or ammonium nitrite salt. Exemplary alkali metal nitrite salts include sodium nitrite, potassium nitrite, lithium nitrite, cesium nitrite, and rubidium nitrite. Exemplary alkaline earth metal nitrite salts include magnesium nitrite, calcium nitrite, barium nitrite, and strontium nitrite. Additional exemplary metal-based inorganic nitrite salts include silver (I) nitrite ($AgNO_2$), cobalt(II) nitrite ($Co(NO_2)_2$), and zinc nitrite ($Zn(NO_2)_2$). The alkali metal nitrite salt, alkaline earth metal nitrite salt, or ammonium nitrite salt may be in the form of solvate, such as a hydrate (e.g., a mono-hydrate or dehydrate). Alternatively, the alkali metal nitrite salt, alkaline earth metal nitrite salt, or ammonium nitrite salt may be anhydrous.

Exemplary ammonium nitrite salts include compounds embraced by the formula $NO_2$—$N(R')_4$, wherein R' represents independently for each occurrence hydrogen, optionally substituted alkyl, optionally substituted heteroalkyl, optionally substituted cycloalkyl, optionally substituted heterocycloalkyl, optionally substituted aryl, optionally substituted aralkyl, optionally substituted heteroaryl, or optionally substituted heteroaralkyl. In certain other embodiments, the ammonium nitrite salt is arginine nitrite, ammonium nitrite ($NH_4O_2$), or tetramethylammonium nitrite.

B. Nitrite-Reductase Promoters

The nitrite reductase promoter enhances conversion of nitrite to nitric oxide in vivo. One exemplary class of nitrite-reductase promoters is an allosteric modulator of hemoglobin, such as compounds that bind to the beta-cysteine-93 residue of hemoglobin to enhance the nitrite-reductase activity of hemoglobin. Another exemplary class of nitrite-reductase promoters is an agent that modulates the oxygen binding affinity of hemoglobin and/or erythrocyte cells, such as an agent that increases oxygen binding affinity of hemoglobin and/or erythrocyte cells. Co-administration of a nitrite reductase promoter with an inorganic nitrite salt results in increased levels of nitric oxide in vivo. One benefit of the combination therapy is that the nitrite reductase promoter allows for generation of beneficial levels of nitric oxide in vivo, while minimizing the amount of inorganic nitrite salt that must be administered to the patient.

Exemplary allosteric modulators of hemoglobin contemplated for use in the methods, compositions, and kits include nitrosating agents such as S-nitroso-N-acetylcysteine, S-nitrosocysteinylglycine, S-nitrosocysteine, S-nitrosohomocysteine, metal nitrosyl complexes, S-nitro compounds, S-nitroso compounds, thionitrites, diazeniumdiolates, and other related nitrosating agents as described in Feelisch, M. and Stamler, J. S., "Donors of Nitrogen Oxides" chapter 7, pp. 71-115 in Methods in Nitric Oxide Research (Freelisch, M. and Stamler, J. S., eds.) John Wiley and Sons, Ltd., Chichester, U.K. (1996), the contents of which are hereby incorporated by reference in their entirety. A nitrosating agent can be chosen for minimal oxidation of the heme iron of hemoglobin, and maximum activity in nitosylating thiol groups such as found on cysteine. Other exemplary allosteric modulators of hemoglobin contemplated for use in the methods, compositions, and kits include 4-pyridylmethyl chloride, an alkoxyalkylchloride, dimethoxymethane, N-(hydroxymethane, N-(hydroxymethyl)acetamide, triphenylmethyl chloride, acetyl chloride, 2-chloroacetic acid, acetic anhydride, a haloacetamide (such as, iodoacetamide, bromoacetamide, chloroacetamide, or fluoroacetamide), a haloacetate (such as iodoacetate, bromoacetate, chloroacetate, or fluoroacetate), benzyl chloride, benzoyl chloride, di-tert-butyl dicarbonate, p-hydroxyphenacyl bromide, p-acetoxybenzyl chloride, p-methoxybenzyl chloride, 2,4-dinitrophenyl fluoride, tetrahydropyran, acetamidohydroxymethane, acetone, bis-carboethoxyethene, 2,2,2-trichloroethoxycarbonyl chloride, tert-butoxycarbonyl chloride, an alkyl isocyanate, and an alkoxyalkyl isocyanate. In certain other embodiments, the allosteric modulator of hemoglobin is an optionally substituted alkyl-R*, optionally substituted aralkyl-R*, or optionally substituted heteroaralkyl-R*, wherein R* is a leaving group, such as halogen, an alkyl sulfonate, arylsulfonate, alkyl acetate, or haloalkyl acetate. In certain other embodiments, the allosteric modulator of hemoglobin is an optionally substituted alkyl-NCO, optionally substituted aryl-NCO, optionally substituted aralkyl-NCO, optionally substituted heterocycyl-NCO, optionally substituted heteroaryl-NCO, or optionally substituted heteroaralkyl-NCO. In certain other embodiments, the allosteric modulator of hemoglobin is an optionally substituted alkyl-C(O)X, optionally substituted aryl-C(O)X, optionally substituted aralkyl-C(O)X, optionally substituted heterocycyl-C(O)X, optionally substituted heteroaryl-C(O)X, or optionally substituted heteroaralkyl-C(O)X, where X is a leaving group, such as halogen or —OC(O)alkyl.

In certain embodiments, the sulfhydryl of the β93-cysteine on hemoglobin may be alkylated with an allosteric modulator of hemoglobin that is a derivatized dextran. For example, in certain embodiments, the dextran may be derivatized to contain a free amino group (e.g., using cyanogen bromide and diaminoethane), and the free amino group may be acylated with an alkylating moiety (e.g., bromoacetyl bromide) that can alkylate the sulfhydryl of the β93-cysteine.

In certain other embodiments, the allosteric modulator of hemoglobin is a polyalkylene glycol. Polyalkylene glycols containing a reactive group are contemplated to react with the β93-cysteine residue of hemoglobin to modulate hemoglobin activity. In certain embodiments, the polyalkylene glycol contains a maleimide group, such as (polyethylene glycol)-maleimide. In certain other embodiments, the polyalkylene glycol contains a N-hydroxysuccinimide group. The polyethylene glycol may have a weight average molecular weight of about 200 g/mol to about 100,000 g/mol, about 200 g/mol to about 20,000 g/mol, about 200 g mol to about 1,000 g/mol, or about 1,000 g/mol to about 10,000 g/mol.

In certain other embodiments, the allosteric modulator of hemoglobin is an organonitro compound embraced by Formula I:

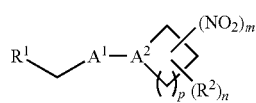

(I)

or a pharmaceutically acceptable salt or solvate thereof, wherein:
$A^1$ is —C(O)— or —$(C(R^3)_2)_x C(O)(C(R^3)_2)_x$—;
$A^2$ is N or —C($R^4$)—;
$R^1$ is halogen, —OS(O)$_2 R^5$, or —OC(O)CF$_3$;
$R^2$ is $C_1$-$C_6$alkyl;
$R^3$ and $R^4$ each represent independently for each occurrence hydrogen or $C_1$-$C_5$alkyl;

$R^5$ is $C_1$-$C_6$alkyl, $C_1$-$C_6$haloalkyl, aryl, or aralkyl;
m and p are independently 1, 2, or 3; and n and x each represent independently for each occurrence 0, 1, 2, or 3.

In certain embodiments, the allosteric modulator of hemoglobin is an organonitro compound embraced by Formula I as defined by particular definitions for variables in Formula I, such as where $A^1$ is —C(O)—. In certain other embodiments, $A^1$ is —$(C(R^3)_2)_x C(O)(C(R^3)_2)_x$—. In certain other embodiments, $A^1$ is —$C(O)(C(R^3)_2)_x$—.

In certain embodiments, $A^2$ is N. In certain other embodiments, $A^2$ is —C($R^4$)—.

In certain embodiments, $R^1$ is halogen, —OS(O)$_2 R^5$, or —OC(O)CF$_3$. In certain other embodiments, $R^1$ is halogen. In certain other embodiments, $R^1$ is —OS(O)$_2 R^5$. In certain other embodiments, $R^1$ is —OC(O)CF$_3$. In certain other embodiments, $R^1$ is chloro, bromo, —OS(O)$_2$-(para-methylphenyl), —OS(O)$_2 CH_3$, —OS(O)$_2 CF_3$, or —OC(O)CF$_3$. In certain embodiments, $R^1$ is bromo.

In certain embodiments, m is 2. In certain other embodiments, m is 1.

In certain embodiments, n is 0. In certain other embodiments, n is 1. In certain other embodiments, n is 2.

In certain embodiments, p is 1. In certain other embodiments, p is 2. In certain other embodiments, p is 3.

The description above describes multiple embodiments relating to compounds of Formula I. The patent application specifically contemplates all combinations of the embodiments. For example, the invention contemplates a compound of Formula I wherein $A^1$ is —C(O)—, $A^2$ is N, $R^1$ is halogen, and n is 0.

In certain embodiments, the compound is a compound of Formula I-A:

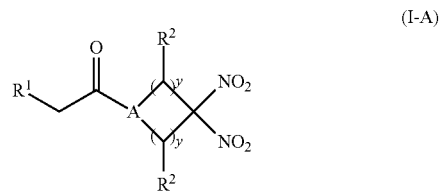

(I-A)

or a pharmaceutically acceptable salt or solvate thereof, wherein:
A is N or C(H);
$R^1$ is chloro, bromo, —OS(O)$_2$—($C_1$-$C_6$alkyl), —OS(O)$_2$—($C_1$-$C_6$haloalkyl), —OS(O)$_2$-(para-methylphenyl), or —OC(O)CF$_3$;
$R^2$ represents independently for each occurrence hydrogen or methyl; and
y represents independently for each occurrence 1 or 2.

In certain embodiments, the allosteric modulator of hemoglobin is an organonitro compound embraced by Formula I-A as defined by particular definitions for variables in Formula I-A, such as where A is N. In certain other embodiments, A is C(H).

In certain embodiments, $R^1$ is chloro or bromo. In certain embodiments, $R^1$ is chloro. In certain other embodiments, $R^1$ is bromo. In certain embodiments, $R^1$ is —OS(O)$_2$—($C_1$-$C_6$alkyl), —OS(O)$_2$—($C_1$-$C_6$haloalkyl), or —OS(O)$_2$-(para-methylphenyl). In certain other embodiments, $R^1$ is —OS(O)$_2 CH_3$, —OS(O)$_2 CF_3$, or —OS(O)$_2$-(para-methylphenyl). In certain other embodiments, $R^1$ is —OC(O)CF$_3$.

In certain embodiments, $R^2$ is hydrogen or methyl. In certain embodiments, $R^2$ is hydrogen.

In certain embodiments, y is 1. In certain embodiments, one occurrence of y is 1, and the other occurrence of y is 2. In certain other embodiments, y is 2.

The description above describes multiple embodiments relating to compounds of Formula I-A. The patent application specifically contemplates all combinations of the embodiments. For example, the invention contemplates a compound of Formula I-A wherein A is N, $R^1$ is chloro or bromo, and $R^2$ is hydrogen.

In certain embodiments, the compound is

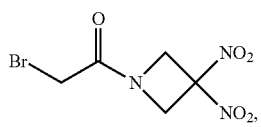

or a pharmaceutically acceptable salt or solvate thereof. In certain other embodiments, the compound is

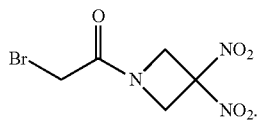

In certain other embodiments, the allosteric modulator of hemoglobin is an organonitro compound embraced by Formula II:

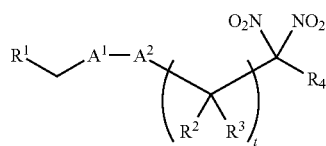

or a pharmaceutically acceptable salt or solvate thereof: wherein:

$A^1$ is —C(O)— or —(C($R^5$)$_2$)$_x$C(O)(C($R^5$)$_2$)$_x$—;
$A^2$ is —N($R^5$)— or —C($R^2$)($R^2$)—;
$R^1$ is halogen, —OS(O)$_2R^6$, or —OC(O)CF$_3$;
$R^2$ and $R^3$ each represent independently for each occurrence hydrogen or $C_1$-$C_6$alkyl; or $R^2$ and $R^3$ are taken together with the carbon atom to which they are attached to form a 3-6 membered, saturated carbocyclic ring;
$R^4$ is hydrogen or $C_1$-$C_6$alkyl;
$R^5$ represents independently for each occurrence hydrogen or $C_1$-$C_6$alkyl;
$R^6$ is $C_1$-$C_6$alkyl, $C_1$-$C_6$haloalkyl, aryl, or aralkyl;
t is an integer in the range from 1 to 12; and
x represents independently for each occurrence 0, 1, 2, or 3.

In certain embodiments, the allosteric modulator of hemoglobin is an organonitro compound embraced by Formula II as defined by particular definitions for variables in Formula II, such as where $A^1$ is —C(O)—. In certain other embodiments, $A^1$ is —(C($R^5$)$_2$)$_x$C(O)(C($R^5$)$_2$)$_x$—. In certain other embodiments, $A^1$ is —C(O)(C($R^5$)$_2$)$_x$—.

In certain embodiments, $A^2$ is —N($R^5$)—. In certain other embodiments, $A^2$ is —C($R^2$)($R^3$)—.

In certain embodiments, $R^1$ is halogen. In certain other embodiments, $R^1$ is —OS(O)$_2R^6$. In certain other embodiments, $R^1$ is —OC(O)CF$_3$. In certain other embodiments, $R^1$ is chloro, bromo, —OS(O)$_2$-(para-methylphenyl), —OS(O)$_2$CH$_3$, —OS(O)$_2$CF$_3$, or —OC(O)CF$_3$. In certain embodiments, $R^1$ is bromo.

In certain embodiments, $R^2$ and $R^3$ each represent independently for each occurrence hydrogen or $C_1$-$C_6$alkyl. In certain other embodiments, $R^2$ and $R^3$ each represent independently for each occurrence hydrogen, methyl, ethyl, or propyl. In certain other embodiments, $R^2$ and $R^3$ each represent independently for each occurrence hydrogen or methyl. In certain embodiments, $R^2$ and $R^3$ are hydrogen.

In certain embodiments, $R^4$ is hydrogen, methyl, ethyl, propyl, butyl, or pentyl. In certain other embodiments, $R^4$ is methyl, ethyl or propyl. In certain other embodiments, $R^4$ is methyl.

In certain embodiments, $R^5$ is hydrogen or methyl. In certain other embodiments, $R^5$ is hydrogen.

In certain embodiments, $R^6$ is $C_1$-$C_6$alkyl or $C_1$-$C_6$haloalkyl. In certain other embodiments, $R^6$ is methyl, ethyl, or trifluoromethyl. In certain other embodiments, $R^6$ is aryl, such as phenyl.

In certain embodiments, t is 1, 2, 3, 4, 5 or 6. In certain other embodiments, t is 1, 2, or 3. In certain other embodiments, t is 1. In certain embodiments, x is 1 or 2.

The description above describes multiple embodiments relating to compounds of Formula II. The patent application specifically contemplates all combinations of the embodiments. For example, the invention contemplates a compound of Formula II wherein $A^1$ is —C(O)—, $A^2$ is —N($R^5$)—, and $R^2$ and $R^3$ are hydrogen.

In certain embodiments, the compound is a compound of Formula II-A:

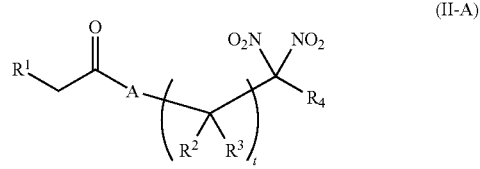

or a pharmaceutically acceptable salt or solvate thereof: wherein:

A is —N($R^5$)— or —C($R^2$)($R^3$)—;
$R^1$ is chloro, bromo, —OS(O)$_2$—($C_1$-$C_6$alkyl), —OS(O)$_2$—($C_1$-$C_6$haloalkyl), —OS(O)$_2$-(para-methylphenyl), or —OC(O)CF$_3$;
$R^2$, $R^3$, and $R^5$ each represent independently for each occurrence hydrogen or methyl;
$R^4$ is hydrogen or $C_1$-$C_6$alkyl; and
t is 1, 2, or 3.

In certain embodiments, the allosteric modulator of hemoglobin is an organonitro compound embraced by Formula II-A as defined by particular definitions for variables in Formula II-A, such as where A is —N($R^5$)—. In certain other embodiments, A is —N(CH$_3$)—. In certain other embodiments, A is —C($R^2$)($R^3$)—. In certain other embodiments, A is —CH$_2$—.

In certain embodiments, $R^1$ is chloro. In certain other embodiments, $R^1$ is bromo. In certain embodiments, $R^1$ is —OS(O)$_2$—($C_1$-$C_6$alkyl), —OS(O)$_2$—($C_1$-$C_6$haloalkyl), or —OS(O)$_2$-(para-methylphenyl). In certain other embodiments, $R^1$ is —OS(O)$_2$CH$_3$, —OS(O)$_2$CF$_3$, of —OS(O)$_2$-(para-methylphenyl). In certain other embodiments, $R^1$ is —OC(O)CF$_3$.

In certain embodiments, $R^2$ and $R^3$ are hydrogen.

In certain embodiments, $R^4$ is hydrogen, methyl, ethyl, propyl, butyl, or pentyl. In certain other embodiments, $R^4$ is methyl, ethyl or propyl. In certain other embodiments, $R^4$ is methyl.

In certain embodiments, $R^5$ is hydrogen or methyl. In certain other embodiments, $R^1$ is hydrogen.

The description above describes multiple embodiments relating to compounds of Formula II-A. The patent application specifically contemplates all combinations of the embodiments. For example, the invention contemplates a compound of Formula II-A wherein A is —N(R$^5$)—, and $R^2$ and $R^3$ are hydrogen.

In certain other embodiments, the allosteric modulator of hemoglobin is one of the compounds listed in Tables 1, 2, or 3 below or a pharmaceutically acceptable salt or solvate thereof.

TABLE 1

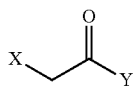

| Compound No. | X | Y |
|---|---|---|
| I-1 | Br | |
| I-2 | Br | |
| I-3 | Br | |
| I-4 | Br | |
| I-5 | Br | |
| I-6 | Br | |
| I-7 | Br | |

TABLE 1-continued

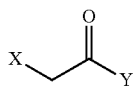

| Compound No. | X | Y |
|---|---|---|
| I-8 | Br | 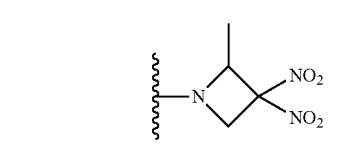 [SMILES: *N1CC([N+](=O)[O-])([N+](=O)[O-])C1C] |
| I-9 | Br | 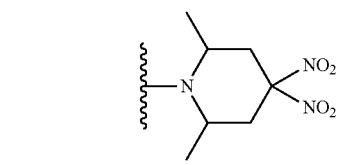 [SMILES: *N1C(C)CC([N+](=O)[O-])([N+](=O)[O-])CC1C] |
| I-10 | Br | 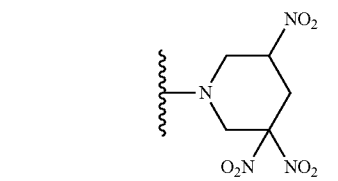 |
| I-11 | Br | 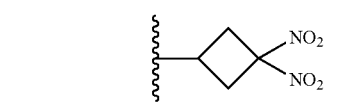 |
| I-12 | Br | 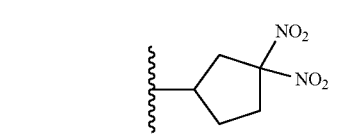 [SMILES: *C1CCC([N+](=O)[O-])([N+](=O)[O-])C1] |
| I-13 | Br | 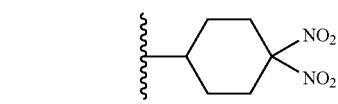 |
| I-14 | Br | 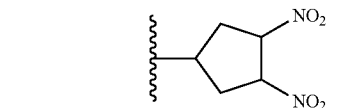 |
| I-15 | Br | 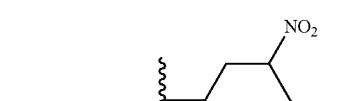 |
| I-16 | Br | 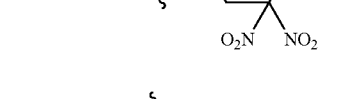 |

TABLE 1-continued

X—CH2—C(=O)—Y

| Compound No. | X | Y |
|---|---|---|
| I-17 | Br | cyclopentyl-NO2 |
| I-18 | Br | dimethyl-cyclobutyl-(NO2)2 |
| I-19 | Cl | azetidinyl-(NO2)2 |
| I-20 | Cl | methyl-azetidinyl-(NO2)2 |
| I-21 | Cl | piperidinyl-(NO2)2 |
| I-22 | Cl | cyclobutyl-(NO2)2 |
| I-23 | I | azetidinyl-(NO2)2 |
| I-24 | I | methyl-azetidinyl-(NO2)2 |
| I-25 | I | piperidinyl-(NO2)2 |
| I-26 | I | cyclobutyl-(NO2)2 |
| I-27 | —OS(O)2CH3 | azetidinyl-(NO2)2 |
| I-28 | —OS(O)2CH3 | cyclopentyl-(NO2)2 |
| I-29 | —OS(O)2CF3 | azetidinyl-(NO2)2 |
| I-30 | —OS(O)2CF3 | cyclopentyl-(NO2)2 |
| I-31 | —O—S(O)2—C6H4—CH3 | azetidinyl-(NO2)2 |
| I-32 | —O—S(O)2—C6H4—CH3 | cyclopentyl-(NO2)2 |
| I-33 | —OC(O)CF3 | azetidinyl-(NO2)2 |
| I-34 | —OC(O)CF3 | methyl-pyrrolidinyl-NO2 |
| I-35 | —OC(O)CF3 | cyclohexyl-(NO2)3 |

TABLE 2
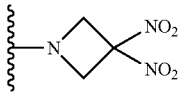
| Compound No. | X | A | Y |
|---|---|---|---|
| II-1 | Br | —CH₂C(O)— | 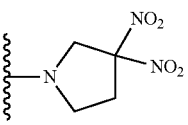 [SMILES: *N1CCC([N+](=O)[O-])([N+](=O)[O-])C1] |
| II-2 | Br | —CH₂C(O)— | 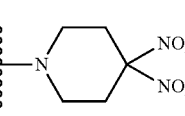 |
| II-3 | Br | —CH₂C(O)— | 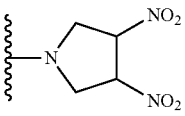 |
| II-4 | Br | —CH₂C(O)— | 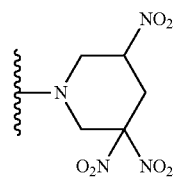 |
| II-5 | Br | —CH₂C(O)— | 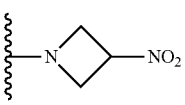 [SMILES: *N1CC([N+](=O)[O-])C1] |
| II-6 | Br | —CH₂C(O)— | 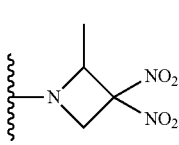 |
| II-7 | Br | —CH₂C(O)— | 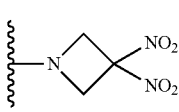 |
| II-8 | Br | —C(O)CH₂CH₂— | 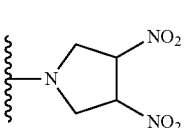 |
| II-9 | Br | —C(O)CH₂CH₂— | 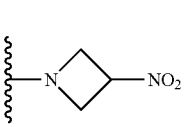 |
| II-10 | Br | —C(O)CH₂CH₂— |  |

TABLE 2-continued
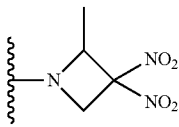
| Compound No. | X | A | Y |
|---|---|---|---|
| II-11 | Br | —C(O)CH$_2$CH$_2$— | 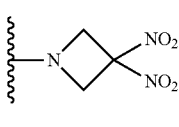 |
| II-12 | Br | —CH$_2$— | 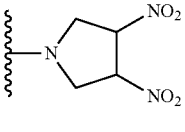 |
| II-13 | Br | —CH$_2$— | 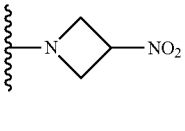 |
| II-14 | Br | —CH$_2$— | 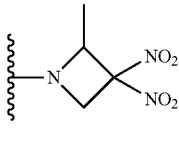 |
| II-15 | Br | —CH$_2$— | 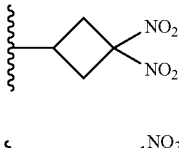 |
| II-16 | Br | —CH$_2$C(O)— | 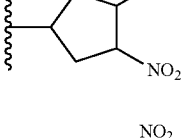 |
| II-17 | Br | —CH$_2$C(O)— | 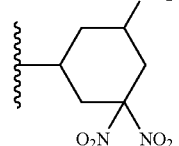 |
| II-18 | Br | —C(O)CH$_2$CH$_2$— | 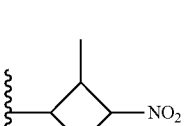 |
| II-19 | Br | —C(O)CH$_2$CH$_2$— | |
| II-20 | Br | —CH$_2$— | 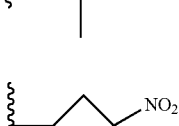 |

TABLE 2-continued

X̰–CH₂–A–(Y)

| Compound No. | X | A | Y |
|---|---|---|---|
| II-21 | Br | —CH₂— | 3,4-dinitrocyclopentyl |
| II-22 | Br | —CH₂— | 2,3-dimethyl-4-nitrocyclobutyl |
| II-23 | Cl | —CH₂C(O)— | 3,3-dinitroazetidin-1-yl |
| II-24 | Cl | —C(O)CH₂CH₂— | 3,3-dinitroazetidin-1-yl |
| II-25 | Cl | —CH₂— | 3,3-dinitroazetidin-1-yl |
| II-26 | Cl | —CH₂C(O)— | 3,3-dinitrocyclobutyl |
| II-27 | Cl | —C(O)CH₂CH₂— | 3,4-dinitrocyclopentyl |
| II-28 | Cl | —CH₂— | 2,3-dimethyl-4-nitrocyclobutyl |
| II-29 | —OS(O)₂CH₃ | —CH₂C(O)— | 3,3-dinitroazetidin-1-yl |
| II-30 | —OS(O)₂CH₃ | —CH₂C(O)— | 3,3-dinitrocyclobutyl |
| II-31 | —OS(O)₂CH₃ | —C(O)CH₂CH₂— | 3,3-dinitroazetidin-1-yl |

TABLE 2-continued

X−CH2−A−Y

| Compound No. | X | A | Y |
|---|---|---|---|
| II-32 | —OS(O)₂CH₃ | —CH₂— | N-pyrrolidine-3,4-di(NO₂) |
| II-33 | —OC(O)₂CF₃ | —CH₂C(O)— | N-azetidine-3,3-di(NO₂) |
| II-34 | —OS(O)₂CF₃ | —CH₂C(O)— | cyclobutane-3,3-di(NO₂) |
| II-35 | —OS(O)₂CF₃ | —C(O)CH₂CH₂— | N-azetidine-3,3-di(NO₂) |
| II-36 | —OS(O)₂CF₃ | —CH₂— | N-pyrrolidine-3,4-di(NO₂) |
| II-37 | —O—S(O)₂—C₆H₄— | —CH₂C(O)— | N-azetidine-3,3-di(NO₂) |
| II-38 | —O—S(O)₂—C₆H₄— | —CH₂C(O)— | cyclobutane-3,3-di(NO₂) |
| II-39 | —O—S(O)₂—C₆H₄— | —C(O)CH₂CH₂— | N-azetidine-3,3-di(NO₂) |
| II-40 | —O—S(O)₂—C₆H₄— | —CH₂— | N-pyrrolidine-3,4-di(NO₂) |
| II-41 | —OC(O)CF₃ | —CH₂C(O)— | N-azetidine-3,3-di(NO₂) |
| II-42 | —OC(O)CF₃ | —CH₂C(O)— | cyclobutane-3,3-di(NO₂) |
| II-43 | —OC(O)CF₃ | —C(O)CH₂CH₂— | N-azetidine-3,3-di(NO₂) |

TABLE 2-continued

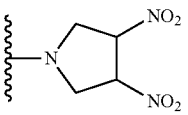

| Compound No. | X | A | Y |
|---|---|---|---|
| II-44 | —OC(O)CF$_3$ | —CH$_2$— | pyrrolidinyl with 3,4-di-NO$_2$ |

TABLE 3

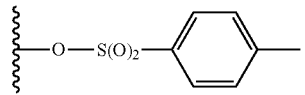

| Compound No. | X | Y | Z |
|---|---|---|---|
| III-1 | Br | —N(H)CH$_2$— | methyl |
| III-2 | Br | —N(H)CH$_2$— | ethyl |
| III-3 | Br | —N(H)CH$_2$— | n-pentyl |
| III-4 | Br | —N(H)CH$_2$— | hydrogen |
| III-5 | Br | —N(H)CH$_2$CH$_2$— | methyl |
| III-6 | Br | —N(H)(CH$_2$)$_4$— | methyl |
| III-7 | Br | —N(CH$_3$)CH$_2$— | methyl |
| III-8 | Br | —N(CH$_3$)(CH$_2$)$_3$— | methyl |
| III-9 | Br | —N(H)C(CH$_3$(H)— | methyl |
| III-10 | Br | —N(H)C(CH$_3$)(H)CH$_2$— | methyl |
| III-11 | Br | —CH$_2$— | methyl |
| III-12 | Br | —(CH$_2$)$_2$— | methyl |
| III-13 | Br | —CH$_2$— | ethyl |
| III-14 | Br | —(CH$_2$)$_4$— | isopropyl |
| III-15 | Br | —(CH$_2$)$_2$— | n-pentyl |
| III-16 | Br | —CH$_2$— | hydrogen |
| III-17 | Br | —CH$_2$CH$_2$C(CH$_3$)$_2$— | methyl |
| III-18 | Br | —CH$_2$C(CH$_3$)$_2$CH$_2$— | methyl |
| III-19 | Cl | —N(H)CH$_2$— | methyl |
| III-20 | Cl | —N(H)CH$_2$— | ethyl |
| III-21 | Cl | —N(CH$_3$)CH$_2$— | methyl |
| III-22 | Cl | —(CH$_2$)$_2$— | methyl |
| III-23 | I | —N(H)CH$_2$— | methyl |
| III-24 | I | —N(H)CH$_2$— | ethyl |
| III-25 | I | —N(CH$_3$)CH$_2$— | methyl |
| III-26 | I | —(CH$_2$)$_2$— | methyl |
| III-27 | —OS(O)$_2$CH$_3$ | —N(H)CH$_2$— | methyl |
| III-28 | —OS(O)$_2$CH$_3$ | —N(CH$_3$)CH$_2$— | methyl |
| III-29 | —OS(O)$_2$CF$_3$ | —N(H)CH$_2$— | methyl |
| III-30 | —OS(O)$_2$CF$_3$ | —N(CH$_3$)CH$_2$— | methyl |
| III-31 | —O—S(O)$_2$-(p-tolyl) | —N(H)CH$_2$— | methyl |
| III-32 | —O—S(O)$_2$-(p-tolyl) | —N(CH$_3$)CH$_2$— | methyl |
| III-33 | —OC(O)CF$_3$ | —N(H)CH$_2$— | methyl |
| III-34 | —OC(O)CF$_3$ | —N(CH$_3$)CH$_2$— | methyl |
| III-35 | —OC(O)CF$_3$ | —(CH$_2$)$_2$— | methyl |

Methods for preparing compounds described herein are illustrated in the following synthetic schemes. These schemes are given for the purpose of illustrating the invention, and should not be regarded in any manner as limiting the scope or the spirit of the invention. Starting materials shown in the schemes can be obtained from commercial sources or can be prepared based on procedures described in the literature.

The synthetic route illustrated in Scheme 1 depicts a general method for preparing cyclic geminal di-nitro compounds. In the first step, chloro epoxide A1 is reacted with t-butylamine to provide hydroxy heterocyclic compound B1. Mesylation of the hydroxyl group of heterocyclic compound B1 with methylsulfonyl chloride gives mesylate C1, which upon reacting with $NaNO_2$ generates cyclic mono-nitro compound D1. Further nitration of compound D1 can be carried out using $NaNO_2$ in the presence of $Na_2S_2O_8$ and $K_3Fe(CN)_6$ to provide geminal di-nitro heterocyclic compound E1. Reacting compound E1 with boron trifluoride etherate and acetyl bromide F provides the desired product G1. Further description of related synthetic procedures are described in, for example, Archibald et al. in *J. Org. Chem.* 1990, 55, 2920-2924; U.S. Pat. No. 7,507,842; and J. P. Agrawal, R. D. Hodgson, *Organic Chemistry of Explosives*, Wiley & Sons, England, 2007 and references cited therein.

This synthetic procedure illustrated in Scheme 1 and described above is contemplated to be applicable to preparing compounds having various substituents at the $R_1$, $R_2$, $R_3$ and $R_4$ positions. If a particular epoxide compound embraced by A1 should contain a functional group sensitive to one or more of the synthetic transformations in Scheme 1, then standard protecting group strategies are contemplated to be applied. For further description of protecting group strategies and procedures, see, for example, Greene, T. W.; Wuts, P. G. M. *Protective Groups in Organic Synthesis*, $2^{nd}$ ed.; Wiley, New York, 1991.

SCHEME 1

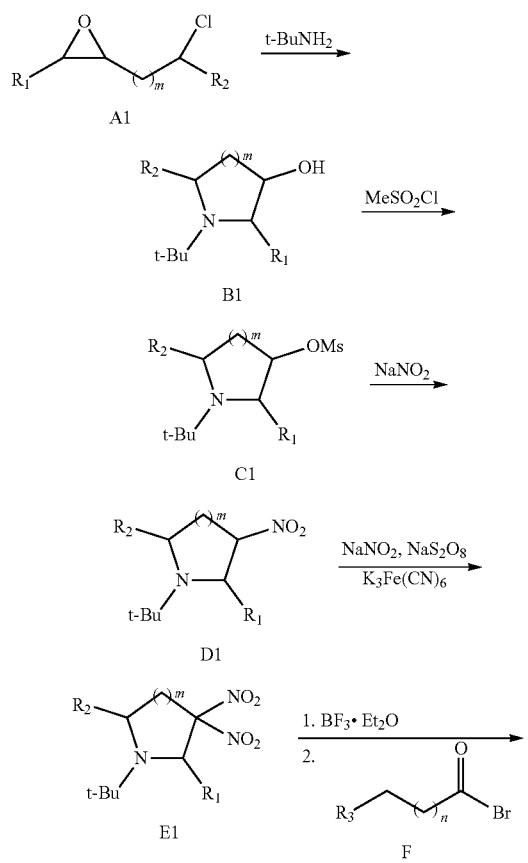

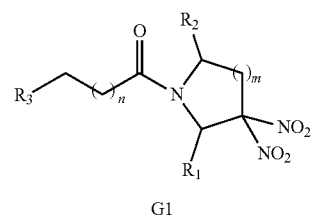

$R_1$ and $R_2$ are, for example, independently H, alkyl, or arylalkyl;
$R_3$ is, for example, halogen, —$OCOCF_3$, or —$OSO_2R_4$ wherein $R_4$ is alkyl, aryl, or arylalky;
n is, for example, 0, 1, or 2;
m is, for example, 0, 1, or 2.

Scheme 2 illustrates a more specific embodiment of the synthetic route shown in Scheme 1 when m is 0. In the first step, epoxide A2 is reacted with t-butylamine to provide hydroxyl azetidine B2. Mesylation of the hydroxyl group of azetidine B2 with methylsulfonyl chloride gives azetidine mesylate C2, which upon reacting with $NaNO_2$ generates mono-nitro azetidine D2. Further nitration of mono-nitro azetidine D2 with $NaNO_2$ in the presence of $Na_2S_2O_8$ and $K_3Fe(CN)_6$ furnishes the germinal di-nitro azetidine E2. Reaction of azetidine E2 with boron trifluoride etherate and acetyl bromide compound F provides the desired di-nitro azetidine product G2. This synthetic procedure is contemplated to be applicable to preparing compounds having various substituents at the $R_1$, $R_2$, $R_3$ and $R_4$ positions. If a particular epoxide compound embraced by A2 should contain a functional group sensitive to one or more of the synthetic transformations in Scheme 2, then standard protecting group strategies are contemplated to be applied. For further description of protecting group strategies and procedures, see, for example, Greene, T. W.; Wuts, P. G. M. *Protective Groups in Organic Synthesis*, $2^{nd}$ ed.; Wiley, New York, 1991. Furthermore, mono-nitro compounds can be prepared by treating mono-nitro compound D2 with a Lewis Acid (e.g., boron trifluoride etherate) and acetyl bromide compound F to provide the desired mono-nitro product.

SCHEME 2

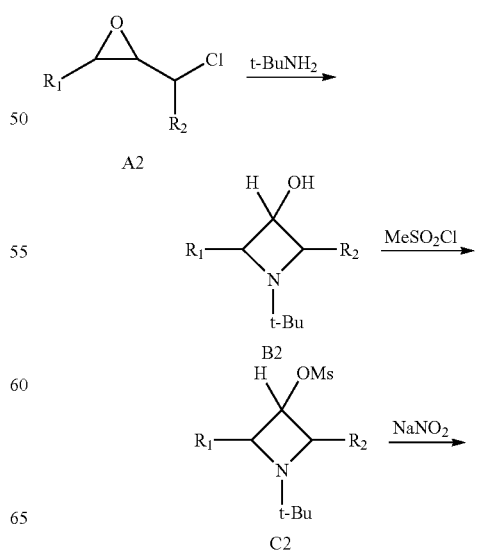

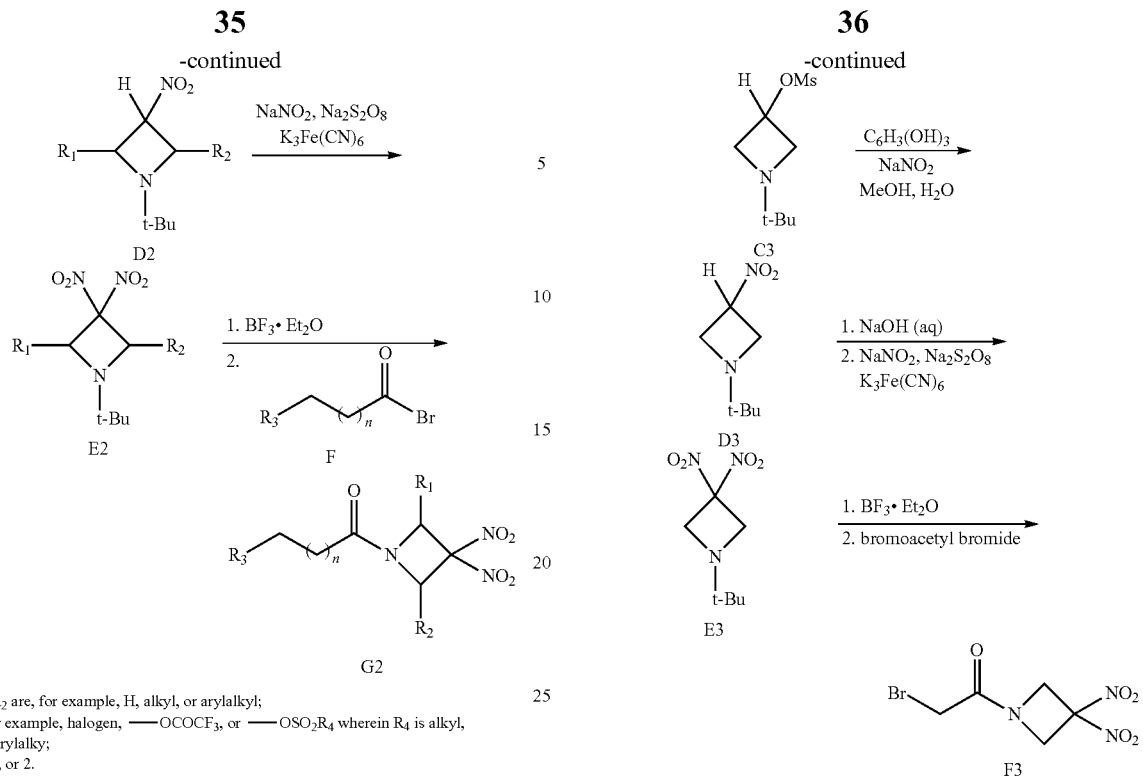

$R_1$ and $R_2$ are, for example, H, alkyl, or arylalkyl;
$R_3$ is, for example, halogen, —OCOCF$_3$, or —OSO$_2$R$_4$ wherein $R_4$ is alkyl, aryl, or arylalky;
n is 0, 1, or 2.

Scheme 3 illustrates another more particular embodiment of the synthetic route shown in Scheme 1 when both $R_1$ and $R_2$ are hydrogen and m is 0. In the first step, commercially available epichlorohydrin A3 is reacted with t-butylamine to provide hydroxyl azetidine B3. Mesylation of the hydroxyl group of azetidine B3 with methylsulfonyl chloride gives azetidine mesylate C3, which upon reacting with NaNO$_2$ generates mono-nitro azetidine D3. Further nitration of mono-nitro azetidine D3 with NaNO$_2$ in the presence of Na$_2$S$_2$O$_8$ and K$_3$Fe(CN)$_6$ furnishes the geminal di-nitro azetidine E3. Reaction of azetidine E3 with boron trifluoride etherate and bromoacetyl bromide provides the desired di-nitro azetidine F3. Further description of related synthetic procedures are described in, for example, Archibald et al. in *J Org. Chem.* 1990, 55, 2920-2924; U.S. Pat. No. 7,507,842; and J. P. Agrawal, R. D. Hodgson, *Organic Chemistry of Explosives*, Wiley & Sons, England, 2007 and references cited therein. Furthermore, mono-nitro compounds can be prepared by treating mono-nitro compound D3 with a Lewis Acid (e.g., boron trifluoride etherate) and acetyl bromide compound F to provide the desired mono-nitro product.

Scheme 4 illustrates an alternative exemplary procedure for preparing cyclic germinal di-nitro compounds. In the first step, heterocyclic compound A4 is reacted with an oxidant, such as pyridinium dichromate (PDC), to provide heterocyclic ketone B4. Reaction of ketone B4 with hydroxylamine gives heterocyclic oxime C4, which upon reaction with N-bromosuccinimide (NBS) produces bromo nitro compound D4. Reaction of compound D4 with NaBH$_4$ furnishes mono-nitro compound E4. Reaction of mono-nitro compound E4 with NaNO$_2$ in the presence of Na$_2$S$_2$O$_8$ and K$_3$Fe(CN)$_6$ provides geminal di-nitro heterocyclic compound F4. Reaction of compound F4 with a deprotecting agent and acetyl bromide compound F provides the desired cyclic geminal di-nitro product G4. Further description of related synthetic procedures are described in, for example, Archibald et al. in *J. Org. Chem.* 1990, 55, 2920-2924; U.S. Pat. No. 7,507,842; and J. P. Agrawal, R. D. Hodgson, *Organic Chemistry of Explosives*, Wiley & Sons, England, 2007 and references cited therein. Furthermore, mono-nitro compounds can be prepared by treating mono-nitro compound D4 with a deprotecting agent and acetyl bromide compound F to provide the desired mono-nitro product.

SCHEME 3

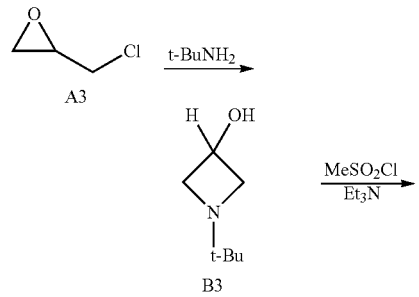

SCHEME 4

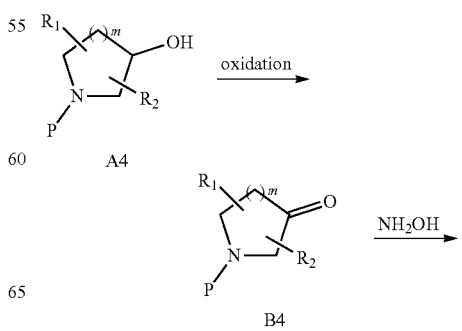

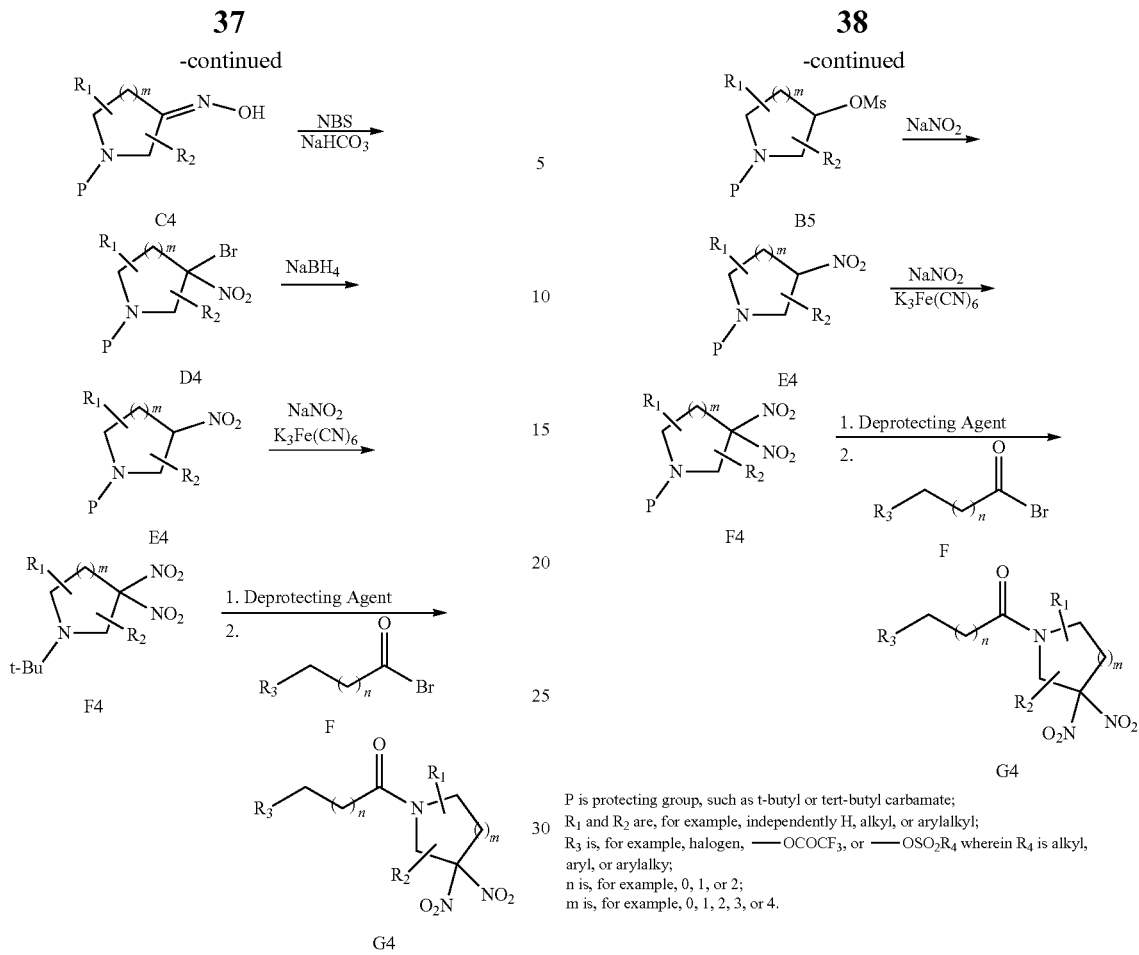

P is protecting group, such as t-butyl or tert-butyl carbamate;
R₁ and R₂ are, for example, independently H, alkyl, or arylalkyl;
R₃ is, for example, halogen, ──OCOCF₃, or ──OSO₂R₄ wherein R₄ is alkyl, aryl, or arylalky;
n is, for example, 0, 1, or 2;
m is, for example, 0, 1, 2, 3, or 4.

Scheme 5 illustrates yet another exemplary procedure for preparing cyclic geminal di-nitro compounds with initial steps different from those shown in Scheme 4. In the first step, heterocyclic compound A4 is reacted with methylsulfonyl chloride to provide heterocyclic mesylate B5. Reaction of mesylate B5 with NaNO₂ gives mono-nitro compound E4. Nitration of compound E4 with NaNO₂ in the presence of Na₂S₂O₈ and K₃Fe(CN)₆ provides geminal di-nitro compound F4. Reaction of compound F4 with a deprotecting agent and acetyl bromide compound F provides the desired di-nitro product G4. Further description of related synthetic procedures are described in, for example, Archibald et al. in *J. Org. Chem.* 1990, 55, 2920-2924; U.S. Pat. No. 7,507,842; and J. P. Agrawal, R. D. Hodgson, *Organic Chemistry of Explosives*, Wiley & Sons, England, 2007 and references cited therein.

P is protecting group, such as t-butyl or tert-butyl carbamate;
R₁ and R₂ are, for example, independently H, alkyl, or arylalkyl;
R₃ is, for example, halogen, ──OCOCF₃, or ──OSO₂R₄ wherein R₄ is alkyl, aryl, or arylalky;
n is, for example, 0, 1, or 2;
m is, for example, 0, 1, 2, 3, or 4.

The synthetic route illustrated in Scheme 6 depicts an exemplary method for preparing cyclic vicinal di-nitro compounds. In the first step, cycloalkene A6 is reacted with N₂O₄ to provide vicinal di-nitro compound B6. Reaction of compound B6 with a deprotecting agent and acetyl bromide compound F provides the desired vicinal di-nitro product C6. Further description of related synthetic procedures are described in, for example, Archibald et al. in *J. Org. Chem.* 1990, 55, 2920-2924; U.S. Pat. No. 7,507,842; and J. P. Agrawal, R. D. Hodgson, *Organic Chemistry of Explosives*, Wiley & Sons, England, 2007 and references cited therein. This synthetic procedure is contemplated to be applicable to preparing compounds having various substituents at the R₁, R₂, R₃ and R₄ positions. If a particular cycloalkene compound embraced by A6 should contain a functional group sensitive to one or more of the synthetic transformations in Scheme 6, then standard protecting group strategies are contemplated to be applied. For further description of protecting group strategies and procedures, see, for example, Greene, T. W.; Wuts, P. G. M. *Protective Groups in Organic Synthesis*, 2ⁿᵈ ed.; Wiley, New York, 1991.

SCHEME 5

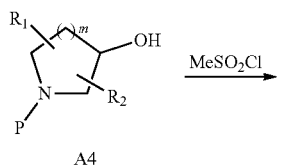

SCHEME 6

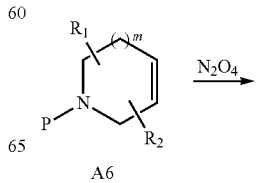

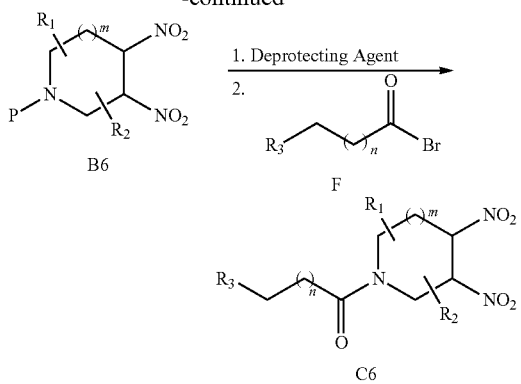
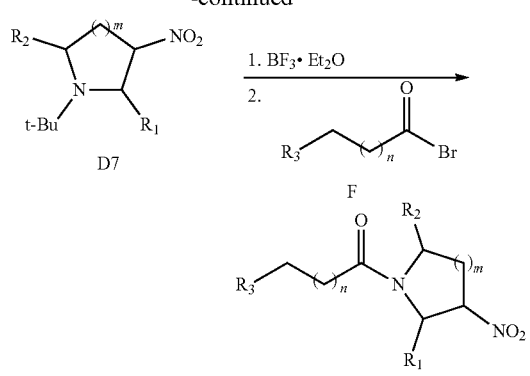

P is protecting group, such as t-butyl or tert-butyl carbamate;
R₁ and R₂ are, for example, independently H, alkyl, or arylalkyl;
R₃ is, for example, halogen, —OCOCF₃, or —OSO₂R₄ wherein R₄ is alkyl, aryl, or arylalky;
n is, for example, 0, 1, or 2;
m is, for example, 0, 1, 2, 3, or 4.

R₁ and R₂ are, for example, independently H, alkyl, or arylalkyl;
R₃ is, for example, halogen, —OCOCF₃, or —OSO₂R₄ wherein R₄ is alkyl, aryl, or arylalky;
n is, for example, 0, 1, or 2;
m is, for example, 0, 1, or 2.

The synthetic route illustrated in Scheme 7 depicts a general method for preparing cyclic mono-nitro compounds. In the first step, chloro epoxide A7 is reacted with t-butylamine to provide hydroxy heterocyclic compound B7. Mesylation of the hydroxyl group of heterocyclic compound B7 with methylsulfonyl chloride gives mesylate C7 which upon reacting with NaNO₂ generates cyclic mono-nitro compound D7. Reaction of compound D7 with boron trifluoride etherate and acetyl bromide F provides the desired product G7. Further description of related synthetic procedures are described in, for example, Archibald et al, in *J. Org. Chem.* 1990, 55, 2920-2924; U.S. Pat. No. 7,507,842; and J. P. Agrawal, R. D. Hodgson, *Organic Chemistry of Explosives*, Wiley & Sons, England, 2007 and references cited therein. This synthetic procedure illustrated in Scheme 7 is contemplated to be applicable to preparing compounds having various substituents at the R₁, R₂, R₃ and R₄ positions. If a particular epoxide compound embraced by A7 should contain a functional group sensitive to one or more of the synthetic transformations in Scheme 7, then standard protecting group strategies are contemplated to be applied. For further description of protecting group strategies and procedures, see, for example, Greene, T. W.; Wuts, P. G. M. *Protective Groups in Organic Synthesis*, 2$^{nd}$ ed.; Wiley, New York, 1991.

SCHEME 7

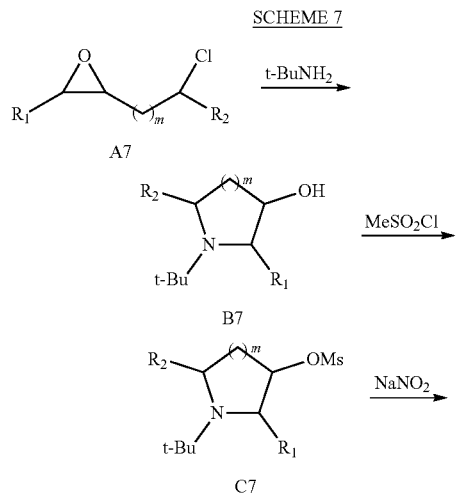

The synthetic routes described above can be modified to prepare compounds having an alkyl halide attached to the ring nitrogen atom. Exemplary synthetic procedures for preparing such compounds include reducing the amide group of compound G1-G4, G7, and C6 to an amine. Alternatively, compound F used in the procedures above could be replaced with an appropriately protected alkylhalide, such that after the alkylation reaction, the protected alkyl group attached to the ring nitrogen atom is deprotected and converted to an alkyl chloride or bromide.

Scheme 8 depicts another exemplary method for preparing cyclic mono-nitro and di-nitro compounds. Reaction of ketone B8 with hydroxylamine gives heterocyclic hydroxylamine C8, which upon reaction with N-bromosuccinimide (NBS) produces bromo nitro compound D8. Reaction of compound D8 with NaBH₄ furnishes mono-nitro compound E8. The hydroxyl protecting group (P, which may be, for example, a tert-butyldimethylsilyl group) and the 1,2-dihydroxyethane protecting group are removed using standard deprotection conditions. Exemplary deprotection conditions for removing a tert-butyldimethyl silyl group include addition of tetra-n-butylammonium fluoride. Exemplary deprotection conditions for removing a 1,2-dihydroxyethane protecting group include addition of hydrochloric acid and water. Hydroxy-ketone F8 can be converted to α-bromo ketone G8 by first reacting compound F8 with methanesulfonyl chloride to form a mesylate and then adding sodium bromide to form α-bromo ketone G8.

Di-nitro compounds can be prepared by reacting mono-nitro compound E8 with NaNO₂ in the presence of Na₂S₂O₈ and K₃Fe(CN)₆ to provide geminal di-nitro heterocyclic compound H8. The hydroxyl protecting group (P, which may be, for example, a tert-butyldimethyl silyl group) and the 1,2-dihydroxyethane protecting group of compound H8 may be removed using standard deprotection conditions. Exemplary deprotection conditions for removing a tert-butyldimethyl silyl group include addition of tetra-n-butylammonium fluoride. Exemplary deprotection conditions for removing a 1,2-dihydroxyethane protecting group include addition of hydrochloric acid and water. Hydroxy-ketone 18 can be converted to α-bromo ketone J8 by first reacting compound 18 with methanesulfonyl chloride to form a mesylate and then adding sodium bromide to form ca-bromo ketone J8. Further description of related synthetic procedures are described in, for example, Archibald et al. in *J.*

Org. Chem. 1990, 55, 2920-2924 and J. P. Agrawal, R. D. Hodgson, *Organic Chemistry of Explosives*, Wiley & Sons, England, 2007 and references cited therein.

SCHEME 8

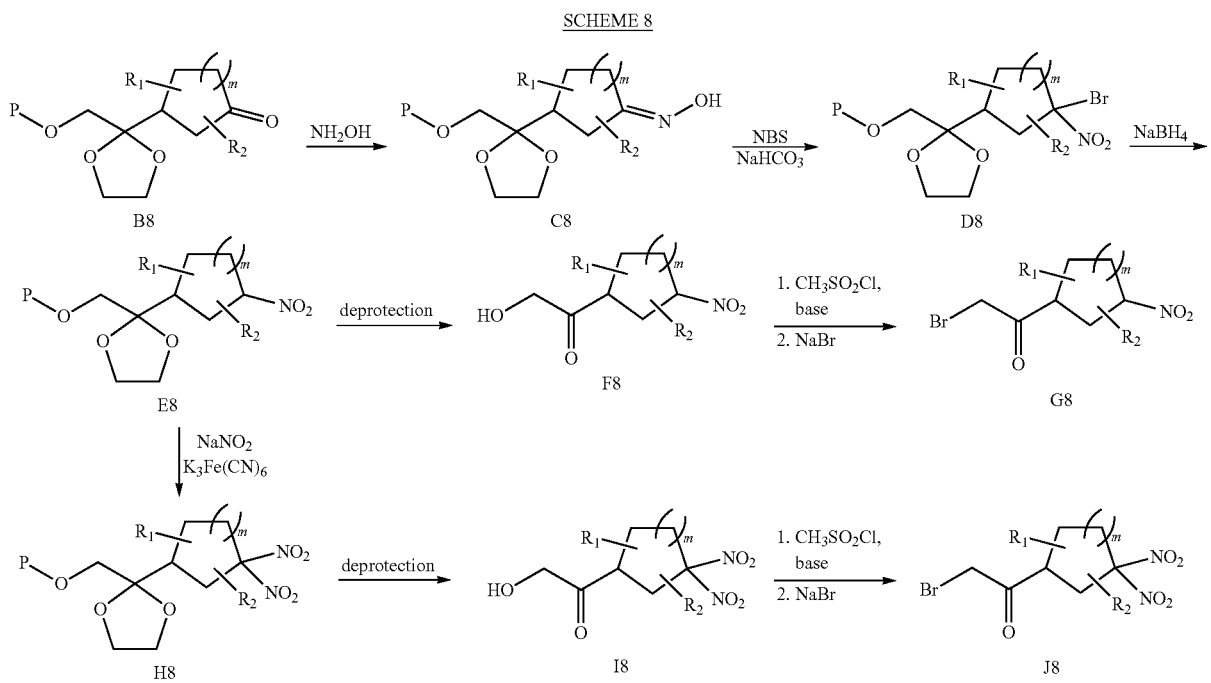

P is protecting group, such as t-butyl or tert-butyl carbamate;
$R_1$ and $R_2$ are, for example, independently H, alkyl, or arylalkyl;
$R_3$ is, for example, halogen, —OCOCF$_3$, or —OSO$_2$R$_4$ wherein $R_4$ is alkyl, aryl, or arylalkyl;
n is, for example, 0, 1, or 2;
m is, for example, 0, 1, 2, 3, or 4.

Scheme 9 illustrates an exemplary procedure for preparing acyclic geminal di-nitro compounds. In the first step, protected amino alcohol A9 is reacted with methylsulfonyl chloride to provide mesylate B9. Reaction of mesylate B9 with NaNO$_2$ gives mono-nitro compound E9. Nitration of compound E9 with NaNO$_2$ in the presence of Na$_2$S$_2$O$_8$ and K$_3$Fe(CN) provides geminal di-nitro compound F9. Reaction of compound F9 with a deprotecting agent and acetyl bromide compound F provides the desired di-nitro product G9. Further description of related synthetic procedures are described in, for example, Archibald et al. in *J. Org. Chem.* 1990, 55, 2920-2924; U.S. Pat. No. 7,507,842; and J. P. Agrawal, R. D. Hodgson, *Organic Chemistry of Explosives*, Wiley & Sons, England, 2007 and references cited therein

SCHEME 9

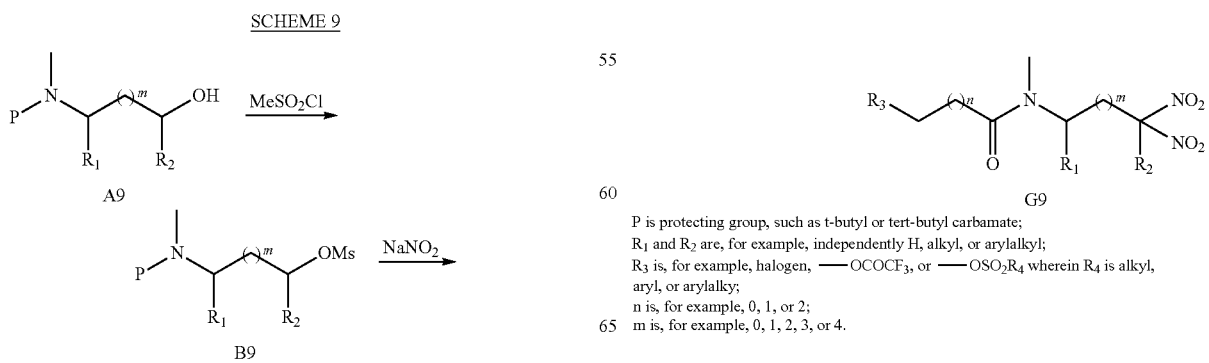

P is protecting group, such as t-butyl or tert-butyl carbamate;
$R_1$ and $R_2$ are, for example, independently H, alkyl, or arylalkyl;
$R_3$ is, for example, halogen, —OCOCF$_3$, or —OSO$_2$R$_4$ wherein $R_4$ is alkyl, aryl, or arylalky;
n is, for example, 0, 1, or 2;
m is, for example, 0, 1, 2, 3, or 4.

II. Therapeutic Applications of Combination Therapy with Inorganic Nitrite Salt and Nitrite-Reductase Promoter The invention provides methods for treating medical disorders using an inorganic nitrite salt in combination with an allosteric modulator of hemoglobin. The methods are contemplated to provide particular advantages in treating or preventing various medical disorders, such as a disorder selected from the group consisting of cancer, a cardiovascular disorder, an ischemic condition, a hemolytic condition, and a bacterial infection. Various aspects of the therapeutic methods are described in detail below.

A. General Therapeutic Methods

The therapeutic methods described herein are particularly well-suited for treatment of diseases associated with hypoxic conditions or ischemic conditions, or otherwise may be treated or prevented using increased levels of nitric oxide. Accordingly, one aspect of the invention provides a method of treating or preventing a disorder selected from the group consisting of cancer, a cardiovascular disorder, an ischemic condition, a hemolytic condition, or a bacterial infection. The method comprises administering to a patient in need thereof a therapeutically effective amount of (i) an inorganic nitrite salt, and (ii) a nitrite reductase promoter, which preferably is an allosteric modulator of hemoglobin that promotes nitrite reductase activity.

Exemplary Cancers

Exemplary types of cancer contemplated to be treated include brain cancer, bladder cancer, breast cancer, cervical cancer, colon cancer, colorectal cancer, endometrial cancer, esophageal cancer, leukemia, lung cancer, liver cancer, melanoma, ovarian cancer, pancreatic cancer, prostate cancer, rectal cancer, renal cancer, stomach cancer, testicular cancer, or uterine cancer.

In certain embodiments, the cancer is a vascularized tumor, solid tumor, squamous cell carcinoma, adenocarcinoma, small cell carcinoma, melanoma, glioma, neuroblastoma, sarcoma (e.g., an angiosarcoma or chondrosarcoma), larynx cancer, parotid cancer, bilary tract cancer, thyroid cancer, acral lentiginous melanoma, actinic keratoses, acute lymphocytic leukemia, acute myeloid leukemia, adenoid cystic carcinoma, adenomas, adenosarcoma, adenosquamous carcinoma, anal canal cancer, anal cancer, anorectum cancer, astrocytic tumor, bartholin gland carcinoma, basal cell carcinoma, biliary cancer, bone cancer, bone marrow cancer, bronchial cancer, bronchial gland carcinoma, carcinoid, cholangiocarcinoma, chondosarcoma, choriod plexus papilloma/carcinoma, chronic lymphocytic leukemia, chronic myeloid leukemia, clear cell carcinoma, connective tissue cancer, cystadenoma, digestive system cancer, duodenum cancer, endocrine system cancer, endodermal sinus tumor, endometrial hyperplasia, endometrial stromal sarcoma, endometrioid adenocarcinoma, endothelial cell cancer, ependymal cancer, epithelial cell cancer, Ewing's sarcoma, eye and orbit cancer, female genital cancer, focal nodular hyperplasia, gallbladder cancer, gastric antrum cancer, gastric fundus cancer, gastrinoma, glioblastoma, glucagonoma, heart cancer, hemangiblastomas, hemangioendothelioma, hemangiomas, hepatic adenoma, hepatic adenomatosis, hepatobiliary cancer, hepatocellular carcinoma, Hodgkin's disease, ileum cancer, insulinoma, intaepithelial neoplasia, interepithelial squamous cell neoplasia, intrahepatic bile duct cancer, invasive squamous cell carcinoma, jejunum cancer, joint cancer, Kaposi's sarcoma, pelvic cancer, large cell carcinoma, large intestine cancer, leiomyosarcoma, lentigo maligna melanomas, lymphoma, male genital cancer, malignant melanoma, malignant mesothelial tumors, medulloblastoma, medulloepithelioma, meningeal cancer, mesothelial cancer, metastatic carcinoma, mouth cancer, mucoepidermoid carcinoma, multiple myeloma, muscle cancer, nasal tract cancer, nervous system cancer, neuroepithelial adenocarcinoma nodular melanoma, non-epithelial skin cancer, non-Hodgkin's lymphoma, oat cell carcinoma, oligodendroglial cancer, oral cavity cancer, osteosarcoma, papillary serous adenocarcinoma, penile cancer, pharynx cancer, pituitary tumors, plasmacytoma, pseudosarcoma, pulmonary blastoma, rectal cancer, renal cell carcinoma, respiratory system cancer, retinoblastoma, rhabdomyosarcoma, sarcoma, serous carcinoma, sinus cancer, skin cancer, small cell carcinoma, small intestine cancer, smooth muscle cancer, soft tissue cancer, somatostatin-secreting tumor, spine cancer, squamous cell carcinoma, striated muscle cancer, submesothelial cancer, superficial spreading melanoma, T cell leukemia, tongue cancer, undifferentiated carcinoma, ureter cancer, urethra cancer, urinary bladder cancer, urinary system cancer, uterine cervix cancer, uterine corpus cancer, uveal melanoma, vaginal cancer, verrucous carcinoma, VIPoma, vulva cancer, well differentiated carcinoma, or Wilms tumor.

The therapeutic methods may optionally comprise exposing the patient to a chemotherapeutic agent or radiation. One exemplary form of radiation is gamma rays, such as those produced from a $^{137}Cs$ source. The amount of radiation can be optimized for particular conditions. In certain embodiments, the quantity of radiation applied to the patient is at least about 2 Gy, about 5 Gy, about 10 Gy, or about 15 Gy. Exemplary chemotherapeutic agents include azacitidine, azathioprine, bleomycin, carboplatin, capecitabine, carmustine, cisplatin, chlorambucil, cyclophosphamide, cytarabine, dacarbazine, daunorubicin, docetaxel, doxifluridine, doxorubicin, epirubicin, epothilone, etoposide, fluorouracil, fulvestrant, gemcitabine, hydroxyurea, idarubicin, imatinib, lomustine, mechlorethamine, mercaptopurine, methotrexate, mitoxantrone, oxaliplatin, paclitaxel, pemetrexed, procarbazine, raloxifene, teniposide, temozolomide, thiotepa, tioguanine, tamoxifen, toremifene, valrubicin, vinblastine, vincristine, vindesine, vinorelbine, and pharmaceutically acceptable salts thereof.

Exemplary Cardiovascular Disorders

Exemplary cardiovascular disorders include pulmonary hypertension, systemic hypertension, angina (e.g., Prinzmetal's angina), Cardiac syndrome X, myocardial infarction, peripheral artery disease, Raynaud's disease, pulmonary embolism, and intravascular thrombosis. In certain embodiments, the cardiovascular disorder is pulmonary hypertension, systemic hypertension, angina (e.g., Prinzmetal's angina), Cardiac syndrome X, myocardial infarction, peripheral artery disease, or Raynaud's disease.

Exemplary Ischemic Conditions

Exemplary ischemic conditions include stroke, an ischemic central nervous system event, cardiac ischemia syndrome, myocardial ischemia, and tissue damage due to hypoxia.

Exemplary Hemolytic Conditions

Exemplary hemolytic conditions include sickle cell disease (including sickle cell crisis), thalassemia, hemoglobin C disease, hemoglobin SC disease, sickle thalassemia, hereditary spherocytosis, hereditary elliptocytosis, hereditary ovalcytosis, glucose-6-phosphate deficiency and other red blood cell enzyme deficiencies, paroxysmal nocturnal hemoglobinuria (PNH), paroxysmal cold hemoglobinuria (PCH), thrombotic thrombocytopenic purpura/hemolytic uremic syndrome (TTP/HUS), idiopathic autoimmune hemolytic anemia, drug-induced immune hemolytic anemia, secondary immune hemolytic anemia, non-immune hemolytic anemia caused by chemical or physical agents, malaria, falciparum malaria, bartonellosis, babesiosis, clostridial infection, severe *Haemophilus influenzae* type b infection, extensive burns, transfusion reaction, rhabdomyolysis (myoglobinemia), transfusion of aged blood, cardiopulmonary bypass, and hemodialysis.

Exemplary Bacterial Infections

The bacterial infection may be a gram-positive bacterial infection or a gram-negative bacterial infection. In certain embodiments, the bacterial infection is a gram-positive cocci bacterial infection or a gram-positive bacilli bacterial infection. In certain other embodiments, the bacterial infection is a gram-negative bacterial infection. In certain other embodiments, the bacterial infection is a gram-negative cocci bacterial infection or a gram-negative bacilli bacterial infection.

The type of bacterial infection can also be characterized according to whether the bacterial infection is caused by anaerobic or aerobic bacteria. In certain embodiments, the bacterial infection is an anaerobic bacterial infection. In certain other embodiments, the bacterial infection is an aerobic bacterial infection.

In certain embodiments, the bacterial infection is a mycobacterial infection. In more particular embodiments, the bacterial infection is an infection of bacteria selected from the group consisting of *Mycobacterium tuberculosis, Staphylococcus aureus, Staphylococcus epidermidis, Enterococcus faecalis, Enterococcus faecium, Streptococcus pneumoniae, Streptococcus pyogenes, Mycobacterium smegmatis, Bacillus anthracis, Escherichia coli, Proteus mirabilis, Pseudomonas aeruginosa, Acinetobacter baumannii, Yersinia enterocolytica, Francisella tularensis, Eubacterium lentum, Bacteroides fragilis, Fusobacterium nucleatum, Porphyromonas asaccharolyticus, Clostridium perfringens,* and *Clostridium difficile*. In still other embodiments the bacterial infection is an infection of *Mycobacterium tuberculosis* bacteria (abbreviated as "MTB" or "TB").

In certain other embodiments, the bacterial infection is due to a member of the genus *Peptostreptococci*, a *Peptostreptococci asaccharolyticus*, a *Peptostreptococci magnus*, a *Peptostreptococci micros*, a *Peptostreptococci prevotii*, a member of the genus *Porphyromonas*, a *Porphyromonas asaccharolytica*, a *Porphyromonas canoris*, a *Porphyromonas gingivalis*, a *Porphyromonas macaccae*, a member of the genus *Actinomyces*, an *Actinomyces israelii*, an *Actinomyces odontolyticus*, a member of the genus *Clostridium*, a *Clostridium innocuum*, a *Clostridium clostridioforme*, a *Clostridium difficile*, a member of the genus *Anaerobiospirillum*, a member of the genus *Bacteroides*, a *Bacteroides tectum*, a *Bacteroides ureolyticus*, a *Bacteroides gracilis* (*Campylobacter gracilis*), a member of the genus a *Prevotella*, a *Prevotella intermedia*, a *Prevotella heparinolytica*, a *Prevotella oris-buccae*, a *Prevotella bivia*, a *Prevotella melaninogenica*, a member of the genus *Fusobacterium*, a *Fusobacterium naviforme*, a *Fusobacterium necrophorum*, a *Fusobacterium varium*, a *Fusobacterium ulcerans*, a *Fusobacterium russii*, a member of the genus *Bilophila*, or a *Bilophila wadsworthia*.

In certain other embodiments, the bacterial infection is due to an antibiotic-resistant bacteria, both aerobic and anaerobic, Gram positive and Gram negative.

Additional Medical Conditions

Additional medical conditions contemplated for treatment or prevention using compositions described herein include nitrogen oxide related rheumatoid arthritis, diabetes (including neuropathies and vasculopathies), and systemic lupus erythematosus.

Additional Considerations

The patient is preferably a human, such as a human suffering from a tumor. The particular combination of inorganic nitrite salt and allosteric modulator of hemoglobin may be selected according to the medical disorder suffered by the patient. For example, in certain embodiments, the inorganic nitrite salt is one of the generic or specific nitrite salts described in Section II, such as alkali metal nitrite, in particular, sodium nitrite. In certain other embodiments, the allosteric modulator of hemoglobin is one of the generic or specific allosteric modulators of hemoglobin described in Section II, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Further yet, for example, with regards to Formula I, in certain embodiments, the compound corresponds to Formula I where $A^1$ is —C(O)—. In certain other embodiments, $A^1$ is —$(C(R^3)_2)_xC(O)(C(R^3)_2)_x$—. In certain other embodiments. $A^1$ is —$C(O)(C(R^3))_2)_x$—.

In certain embodiments, $A^2$ is N. In certain other embodiments, $A^2$ is —$C(R^4)$—.

In certain embodiments, $R^1$ is halogen, —$OS(O)_2R^5$, or —$OC(O)CF_3$. In certain other embodiments, $R^1$ is halogen. In certain other embodiments, $R^1$ is —$OS(O)_2R^5$. In certain other embodiments, $R^1$ is —$OC(O)CF_3$. In certain other embodiments, $R^1$ is chloro, bromo, —$OS(O)_2$-(para-methylphenyl), —$OS(O)_2CH_3$, —$OS(O)_2CF_3$, or —$OC(O)CF_3$. In certain embodiments, $R^1$ is bromo.

In certain embodiments, m is 2. In certain other embodiments, m is 1. In certain embodiments, n is 0. In certain other embodiments, n is 1. In certain other embodiments, n is 2. In certain embodiments, p is 1. In certain other embodiments, p is 2. In certain other embodiments, p is 3.

In certain embodiments, the allosteric modulator of hemoglobin is a compound of Formula I-A:

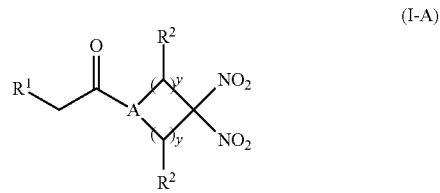

(I-A)

or a pharmaceutically acceptable salt or solvate thereof, wherein:

A is N or C(H);

$R^1$ is chloro, bromo, —$OS(O)_2$—($C_1$-$C_6$alkyl), —$OS(O)_2$—($C_1$-$C_6$haloalkyl), —$OS(O)_2$-(para-methylphenyl), or —$OC(O)CF_3$;

$R^2$ represents independently for each occurrence hydrogen or methyl;

y represents independently for each occurrence 1 or 2.

In certain embodiments, A is N. In certain other embodiments, A is C(H).

In certain embodiments, $R^1$ is chloro, in certain other embodiments, $R^1$ is bromo.

In certain embodiments, $R^1$ is —$OS(O)_2$—($C_1$-$C_6$alkyl), —$OS(O)_2$—($C_1$-$C_6$haloalkyl), or —$OS(O)_2$-(para-methylphenyl). In certain other embodiments, $R^1$ is —OS(O)$_2$CH$_3$, —OS(O)$_2$CF$_3$, or —OS(O)$_2$-(para-methylphenyl). In certain other embodiments, $R^1$ is —OC(O)CF$_3$.

In certain embodiments, $R^2$ is hydrogen or methyl. In certain embodiments, $R^2$ is hydrogen.

In certain embodiments, y is 1. In certain embodiments, one occurrence of y is 1, and the other occurrence of y is 2. In certain other embodiments, y is 2.

In certain embodiments, the allosteric modulator of hemoglobin is

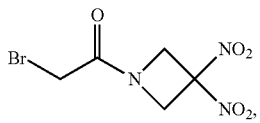

or a pharmaceutically acceptable salt or solvate thereof. In certain other embodiments, the allosteric modulator of hemoglobin is

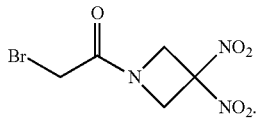

In certain other embodiments, the allosteric modulator of hemoglobin is one of the compounds listed in Tables 1 and 2 herein or a pharmaceutically acceptable salt or solvate thereof.

The description above describes multiple embodiments relating to methods of treating various disorders using an inorganic nitrite salt in combination with an allosteric modulator of hemoglobin. The patent application specifically contemplates all combinations of the embodiments. For example, the invention contemplates treating a tumor by administering a therapeutically effective amount of sodium nitrite in combination with a compound of Formula I-A wherein A is N, $R^1$ is chloro or bromo, and $R^1$ is hydrogen. Further, for example, the invention contemplates treating a tumor by administering a therapeutically effective amount of sodium nitrite in combination with a compound of Formula II wherein $A^1$ is —C(O)—, $A^2$ is N($R^5$), and $R^2$ and $R^3$ are hydrogen.

B. Methods of Increasing the Amount of Nitric Oxide Produced by Hemoglobin

Another aspect of the invention provides a method of increasing the amount of nitric oxide produced by hemoglobin in a patient. The method comprises administering to a patient in need thereof a therapeutically effective amount of (i) an inorganic nitrite salt, and (ii) a nitrite reductase promoter, preferably an allosteric modulator of hemoglobin that promotes nitrite reductase activity. In certain embodiments, the allosteric modulator of hemoglobin is administered at a dosage sufficient to cause a ten percent increase in the rate at which hemoglobin converts nitrite to nitric oxide in vivo. In certain other embodiments, the dose of inorganic nitrite salt and dose of allosteric modulator of hemoglobin are sufficient to cause a ten percent increase in the rate at which hemoglobin converts nitrite to nitric oxide in vivo.

C. Methods of Preventing Sickling of a Red Blood Cell

Another aspect of the invention provides a method of preventing sickling of a red blood cell susceptible to sickling. The method comprises exposing said red blood cell to an effective amount of (i) an inorganic nitrite salt, and (ii) a nitrite reductase promoter (which preferably is an allosteric modulator of hemoglobin that promotes nitrite reductase activity) to prevent sickling of the red blood cell.

In certain embodiments, the red blood cell is a red blood cell in a patient suffering from sickle cell anemia. In certain embodiments, less than 10% of a population of said red blood cells convert to sickle form when exposed to an effective amount of (i) an inorganic nitrite salt, and (ii) an allosteric modulator of hemoglobin that promotes nitrite reductase activity, under hypoxic conditions. In certain embodiments, the hypoxic condition is characterized by a pO$_2$ of less than about 10 mm Hg.

D. Dosing Amounts

Generally, the combination of pharmaceutical agents is delivered to the patient in an effective amount. Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient. The selected dosage level will depend upon a variety of factors including the activity of the particular compound of the present invention employed, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

In general, a suitable daily dose of a compound of the invention will be that amount of the compound which is the lowest dose effective to produce a therapeutic effect. If desired, the effective daily dose of the active compound may be administered as two, three, four, five, six or more sub-doses administered separately at appropriate intervals throughout the day, optionally, in unit dosage forms. Preferred dosing is one administration per day.

In certain embodiments, an inorganic nitrite is administered at a daily dosage of from about 0.1 μg/kg to about 10 mg/kg, about 1 μg to about 5 mg/kg, about 0.05 mg/kg to about 10 mg/kg, about 0.1 mg/kg to about 5 mg/kg, about 0.5 mg/kg to about 5 mg/kg, about 0.5 mg/kg to about 3 mg/kg, about 0.1 mg/kg to about 1.5 mg/kg, about 0.1 mg/kg to about 0.35 mg/kg, about 0.35 mg/kg to about 0.75 mg/kg, or about 0.75 mg/kg to about 1 mg/kg. In certain other embodiments, an inorganic nitrite may be administered in an amount such that the plasma concentration of nitrite ion is from about 0.05 μM to about 200 μM, about 0.1 μM to about 100 μM, about 0.5 μM to about 100 μM, about 0.1 μM to about 100 μM, or about 1 μM to about 100 μM for a desired period of time. In certain embodiments, the desired plasma concentration is maintained for a period of from about 1 hour to about 20 hours, about 1 hour to about 10 hours, or about 1 hour to about 5 hours.

C. Combination Therapy

The therapeutic methods embrace combination therapy, which includes the administration of an inorganic nitrite salt in combination with an allosteric modulator of hemoglobin as part of a specific treatment regimen intended to provide the beneficial effect from the co-action of these therapeutic agents. Administration of these therapeutic agents in combination typically is carried out over a defined time period (e.g., hours or days depending upon the combination selected). The combination therapy may involve administration of two or more of these therapeutic agents as part of separate monotherapy regimens that result in the combinations of the present invention. Combination therapy also includes administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues.

It is understood that the therapeutic agents can be administered by the same route or by different routes. For example, a first therapeutic agent of the combination selected may be administered by intravenous administration while the other therapeutic agent(s) of the combination may be administered orally. Alternatively, for example, all therapeutic agents may be administered orally or all therapeutic agents may be administered by intravenous injection.

IV. Treating Patients with Reduced Blood Volume and/or in Need of Transfusion One aspect of the invention provides a method of treating a patient suffering from reduced blood volume. The method comprises administering to a patient in need thereof a blood product by injection and a therapeutic agent selected from the group consisting of an organonitro compound of Formula I, organonitro compound of Formula II, hemoglobin conjugate of Formula III, hemoglobin conjugate of Formula IV, and an erythrocyte cell that has been exposed to an organonitro compound of Formula I or II; wherein Formula I is represented by:

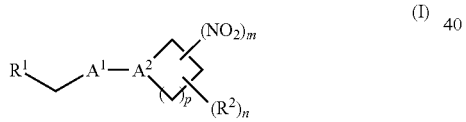

(I)

or a pharmaceutically acceptable salt or solvate thereof, wherein:
$A^1$ is —C(O)— or —$(C(R^3)_2)_x C(O)(C(R^3)_2)_x$—;
$A^2$ is N or —$C(R^4)$—;
$R^1$ is halogen, —$OS(O)_2 R^5$, or —$OC(O)CF_3$;
$R^2$ is $C_1$-$C_6$alkyl;
$R^3$ and $R^4$ each represent independently for each occurrence hydrogen or $C_1$-$C_5$alkyl;
$R^5$ is $C_1$-$C_6$alkyl, $C_1$-$C_6$haloalkyl, aryl, or aralkyl;
m and p are independently 1, 2, or 3; and
n and x each represent independently for each occurrence 0, 1, 2, or 3;
Formula II is represented by:

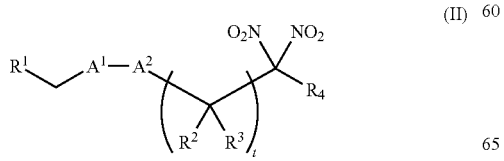

(II)

or a pharmaceutically acceptable salt or solvate thereof: wherein:
$A^1$ is —C(O)— or —$(C(R^5)_2)_x C(O)(C(R^5)_2)_x$—;
$A^2$ is —$N(R^5)$— or —$C(R^2)(R^3)$—;
$R^1$ is halogen, —$OS(O)_2 R^6$, or —$OC(O)CF_3$;
$R^2$ and $R^3$ each represent independently for each occurrence hydrogen or $C_1$-$C_6$alkyl; or
$R^2$ and $R^3$ are taken together with the carbon atom to which they are attached to form a 3-6 membered, saturated carbocyclic ring;
$R^4$ is hydrogen or $C_1$-$C_6$alkyl;
$R^5$ represents independently for each occurrence hydrogen or $C_1$-$C_6$alkyl;
$R^6$ is $C_1$-$C_6$alkyl, $C_1$-$C_6$haloalkyl, aryl, or aralkyl;
t is an integer in the range from 1 to 12; and
x represents independently for each occurrence 0, 1, 2, or 3;
Formula III is represented by:

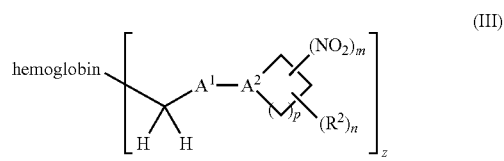

(III)

or a pharmaceutically acceptable salt or solvate thereof, wherein:
$A^1$ is —C(O)— or —$C(O)(C(R^3)_2)_x$—;
$A^2$ is N or —$C(R^4)$—;
$R^2$ is $C_1$-$C_6$alkyl;
$R^3$ and $R^4$ each represent independently for each occurrence hydrogen or $C_1$-$C_5$alkyl;
m and p are independently 1, 2, or 3;
n is 0, 1, 2, or 3;
x is 1, 2, or 3; and
z is an integer from 1 to 10; and
Formula IV is represented by:

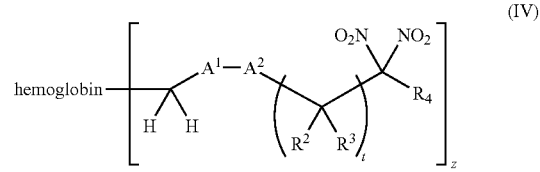

(IV)

or a pharmaceutically acceptable salt or solvate thereof, wherein:
$A^1$ is —C(O)— or —$C(O)(C(R^5)_2)_x$—;
$A^2$ is —$N(R^5)$— or —$C(R^2)(R^3)$—;
$R^2$ and $R^3$ each represent independently for each occurrence hydrogen or $C_1$-$C_6$alkyl; or
$R^2$ and $R^3$ are taken together with the carbon atom to which they are attached to form a 3-6 membered, saturated carbocyclic ring;
$R^4$ is hydrogen or $C_1$-$C_6$alkyl;
$R^5$ represents independently for each occurrence hydrogen or $C_1$-$C_6$alkyl;
t is an integer in the range from 1 to 12;
x is 1, 2, or 3; and
z is an integer from 1 to 10.

In certain embodiments, the patient suffering from reduced blood volume is suffering from hemorrhagic shock.

Hemorrhagic shock is characterized by rapid and significant loss of blood (hypovolemia), resulting in the inadequate delivery of oxygen and nutrients to meet metabolic demands. Compensatory mechanisms are often activated to preserve perfusion selectively to the brain and heart at the expense of other organ systems with progressive development of shock at the cellular and tissue level due to blood flow redistribution. The present method provides a treatment for such hemorrhagic shock.

Another aspect of the invention provides a method of performing a blood transfusion to a patient. The method comprises administering to a patient in need thereof a blood product by injection and a therapeutic agent selected from the group consisting of an organonitro compound of Formula I, organonitro compound of Formula II, hemoglobin conjugate of Formula III, hemoglobin conjugate of Formula IV, and an erythrocyte cell that has been exposed to an organonitro compound of Formula I or II, wherein Formula I is represented by:

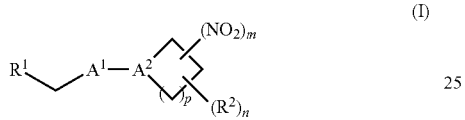

or a pharmaceutically acceptable salt or solvate thereof, wherein:
$A^1$ is —C(O)— or —(C(R$^3$)$_2$)$_x$C(O)(C(R$^3$)$_2$)$_x$—;
$A^2$ is N or —C(R$^4$)—;
$R^1$ is halogen, —OS(O)$_2$R$^5$, or —OC(O)CF$_3$;
$R^2$ is $C_1$-$C_6$alkyl;
$R^3$ and $R^4$ each represent independently for each occurrence hydrogen or $C_1$-$C_5$alkyl;
$R^5$ is $C_1$-$C_6$alkyl, $C_1$-$C_6$haloalkyl, aryl, or aralkyl;
m and p are independently 1, 2, or 3; and
n and x each represent independently for each occurrence 0, 1, 2, or 3;
Formula II is represented by:

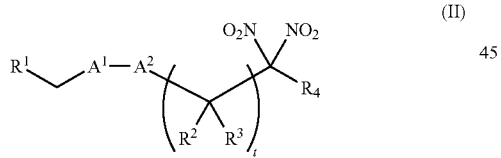

or a pharmaceutically acceptable salt or solvate thereof:
wherein:
$A^1$ is —C(O)— or —(C(R$^5$)$_2$)$_x$C(O)(C(R$^5$)$_2$)$_x$—;
$A^2$ is —N(R$^5$)— or —C(R$^2$)(R$^3$)—;
$R^1$ is halogen, —OS(O)$_2$R$^6$, or —OC(O)CF$_3$;
$R^2$ and $R^3$ each represent independently for each occurrence hydrogen or $C_1$-$C_6$alkyl; or
$R^2$ and $R^3$ are taken together with the carbon atom to which they are attached to form a 3-6 membered, saturated carbocyclic ring;
$R^4$ is hydrogen or $C_1$-$C_6$alkyl;
$R^5$ represents independently for each occurrence hydrogen or $C_1$-$C_6$alkyl;
$R^6$ is $C_1$-$C_6$alkyl, $C_1$-$C_6$haloalkyl, aryl, or aralkyl;
t is an integer in the range from 1 to 12; and
x represents independently for each occurrence 0, 1, 2, or 3;

Formula III is represented by:

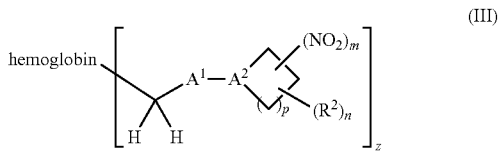

or a pharmaceutically acceptable salt or solvate thereof, wherein:
$A^1$ is —C(O)— or —C(O)(C(R$^3$)$_2$)$_x$—;
$A^2$ is N or —C(R$^4$)—;
$R^2$ is $C_1$-$C_6$alkyl;
$R^3$ and $R^4$ each represent independently for each occurrence hydrogen or $C_1$-$C_5$alkyl;
m and p are independently 1, 2, or 3;
n is 0, 1, 2, or 3;
x is 1, 2, or 3; and
z is an integer from 1 to 10; and
Formula IV is represented by:

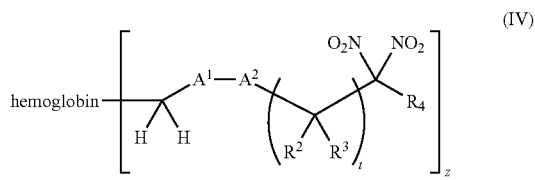

or a pharmaceutically acceptable salt or solvate thereof, wherein:
$A^1$ is —C(O)— or —C(O)(C(R$^5$)$_2$)$_x$—;
$A^2$ is —N(R$^5$)— or —C(R$^2$)(R$^3$)—;
$R^2$ and $R^3$ each represent independently for each occurrence hydrogen or $C_1$-$C_6$alkyl; or
$R^2$ and $R^3$ are taken together with the carbon atom to which they are attached to form a 3-6 membered, saturated carbocyclic ring;
$R^4$ is hydrogen or $C_1$-$C_6$alkyl;
$R^5$ represents independently for each occurrence hydrogen or $C_1$-$C_6$alkyl;
t is an integer in the range from 1 to 12;
x is 1, 2, or 3; and
z is an integer from 1 to 10.

In certain embodiments, the blood product comprises erythrocyte cells. In certain embodiments, the blood product comprises blood plasma. In certain other embodiments, the blood product comprises erythrocyte cells and blood plasma.

In certain other embodiments, the blood product and organonitro compound are administered to the patient concurrently.

In certain embodiments, the blood product is administered to the patient separately from the therapeutic agent.

In certain embodiments, the patient receives, by intravenous injection, a single composition comprising blood product and the therapeutic agent. In other certain embodiments, the patient receives, by intravenous injection, a single composition comprising a therapeutic agent, plasma, and erythrocyte cells. One exemplary composition is provided below in Table 1.

TABLE 1

Exemplary Composition for Intravenous Injection*

| Component | Amount |
|---|---|
| Erythrocyte cells (vol %) | 35-60 |
| Plasma (mL) | 17 |
| Anticoagulant | As needed (e.g., 4 mL) |
| Therapeutic Agent (e.g., ABDNAZ) | As needed, such as, an amount to treat hemorrhagic shock. |

*Amounts are based on a composition having a total volume of 282 mL.

In certain embodiments, the method further comprises administering an alkali metal nitrite to the patient. In other embodiments, the method further comprises administering sodium nitrite to the patient.

In certain embodiments, the patient receives a single composition comprising blood product, therapeutic agent, and an alkali metal nitrite.

In certain embodiments, the therapeutic agent is an organonitro compound of Formula I. In certain other embodiments, the therapeutic agent is an erythrocyte cell that has been exposed to an organonitro compound of Formula I, and said therapeutic agent is administered by injection (such as intravenous injection).

In certain embodiments, $A^1$ is —C(O)—, and $A^2$ is N.
In certain embodiments, $R^1$ is bromo.
In certain embodiments, n is 0, and m is 2.

The description above describes multiple embodiments relating to compounds of Formula I. The patent application specifically contemplates all combinations of the embodiments. For example, the invention contemplates a compound of Formula I wherein $A^1$ is —C(O)—, $A^2$ is N, $R^1$ is halogen, and n is 0.

In certain embodiments, the therapeutic agent is a compound of Formula I-A:

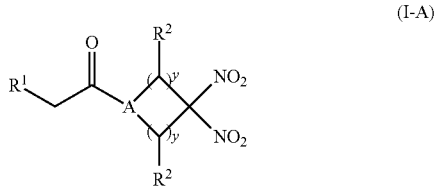

(I-A)

or a pharmaceutically acceptable salt or solvate thereof, wherein:

A is N or C(H);

$R^1$ is chloro, bromo, —OS(O)$_2$—(C$_1$-C$_6$alkyl), —OS(O)$_2$—(C$_1$-C$_6$haloalkyl), —OS(O)$_2$-(para-methylphenyl), or —OC(O)CF$_3$;

$R^2$ represents independently for each occurrence hydrogen or methyl; and y represents independently for each occurrence 1 or 2.

In certain embodiments, the therapeutic agent is compound embraced by Formula I-A as defined by particular definitions for variables in Formula I-A, such as where A is N. In certain other embodiments, A is C(H).

In certain embodiments, $R^1$ is chloro or bromo. In certain embodiments, $R^1$ is chloro. In certain other embodiments, $R^1$ is bromo. In certain embodiments, $R^1$ is —OS(O)$_2$—(C$_1$-C$_6$alkyl), —OS(O)$_2$—(C$_1$-C$_6$haloalkyl), or —OS(O)$_2$-(para-methylphenyl). In certain other embodiments, $R^1$ is —OS(O)$_2$CH$_3$, —OS(O)$_2$CF$_3$, or —OS(O)$_2$-(para-methylphenyl). In certain other embodiments, $R^1$ is —OC(O)CF$_3$.

In certain embodiments, $R^2$ is hydrogen or methyl. In certain embodiments, $R^2$ is hydrogen.

In certain embodiments, y is 1. In certain embodiments, one occurrence of y is 1, and the other occurrence of y is 2. In certain other embodiments, y is 2.

The description above describes multiple embodiments relating to compounds of Formula I-A. The patent application specifically contemplates all combinations of the embodiments. For example, the invention contemplates a compound of Formula I-A wherein A is N, $R^1$ is chloro or bromo, and $R^2$ is hydrogen.

In certain embodiments, the therapeutic agent is

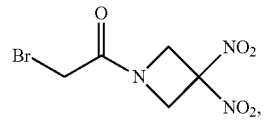

or a pharmaceutically acceptable salt thereof.

In certain embodiments, the therapeutic agent an organonitro compound embraced by Formula II as defined by particular definitions for variables in Formula II, such as where A is —C(O)—. In certain other embodiments, $A^1$ is —(C(R$^5$)$_2$)$_x$C(O)(C(R$^5$)$_2$)$_x$—. In certain other embodiments, $A^1$ is —C(O)(C(R$^5$)$_2$)$_x$—.

In certain embodiments, $A^2$ is —N(R$^5$)—. In certain other embodiments, $A^2$ is —C(R$^2$)(R$^3$)—.

In certain embodiments, $R^1$ is halogen. In certain other embodiments, $R^1$ is —OS(O)$_2$R$^6$. In certain other embodiments, $R^1$ is —OC(O)CF$_3$. In certain other embodiments, $R^1$ is chloro, bromo, —OS(O)$_2$-(para-methylphenyl), —OS(O)$_2$CH$_3$, —OS(O)$_2$CF$_3$, or —OC(O)CF$_3$. In certain embodiments, $R^1$ is bromo.

In certain embodiments, $R^2$ and $R^3$ each represent independently for each occurrence hydrogen or C$_1$-C$_6$alkyl. In certain other embodiments, $R^2$ and $R^3$ each represent independently for each occurrence hydrogen, methyl, ethyl, or propyl. In certain other embodiments, $R^2$ and $R^3$ each represent independently for each occurrence hydrogen or methyl. In certain embodiments, $R^2$ and $R^3$ are hydrogen.

In certain embodiments, $R^4$ is hydrogen, methyl, ethyl, propyl, butyl, or pentyl. In certain other embodiments, $R^4$ is methyl, ethyl or propyl. In certain other embodiments, $R^4$ is methyl.

In certain embodiments, $R^5$ is hydrogen or methyl. In certain other embodiments, $R^5$ is hydrogen.

In certain embodiments, $R^6$ is C$_1$-C$_6$alkyl or C$_1$-C$_6$haloalkyl. In certain other embodiments, $R^6$ is methyl, ethyl, or trifluoromethyl. In certain other embodiments, $R^6$ is aryl, such as phenyl.

In certain embodiments, t is 1, 2, 3, 4, 5 or 6. In certain other embodiments, t is 1, 2, or 3. In certain other embodiments, t is 1. In certain embodiments, x is 1 or 2.

The description above describes multiple embodiments relating to compounds of Formula II. The patent application specifically contemplates all combinations of the embodiments. For example, the invention contemplates a compound of Formula II wherein $A^1$ is —C(O)—, $A^2$ is —N(R$^5$)—, and $R^2$ and $R^3$ are hydrogen.

In certain embodiments, the therapeutic agent is a compound of Formula II-A:

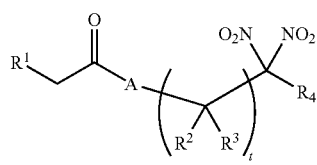

(II-A)

or a pharmaceutically acceptable salt or solvate thereof: wherein:

A is —N(R$^5$)— or —C(R$^2$)(R$^3$)—;
R$^1$ is chloro, bromo, —OS(O)$_2$—(C$_1$-C$_6$alkyl), —OS(O)$_2$—(C$_1$-C$_6$haloalkyl), —OS(O)$_2$-(para-methylphenyl), or —OC(O)CF$_3$;
R$^2$, R$^3$, and R$^5$ each represent independently for each occurrence hydrogen or methyl;
R$^4$ is hydrogen or C$_1$-C$_6$alkyl; and
t is 1, 2, or 3.

In certain embodiments, the therapeutic agent is an organonitro compound embraced by Formula II-A as defined by particular definitions for variables in Formula II-A, such as where A is —N(R$^5$)—. In certain other embodiments, A is —N(CH$_3$)—. In certain other embodiments, A is —C(R$^2$)(R$^3$)—. In certain other embodiments, A is —CH$_2$—.

In certain embodiments, R$^1$ is chloro. In certain other embodiments, R$^1$ is bromo. In certain embodiments, R$^1$ is —OS(O)$_2$—(C$_1$-C$_6$alkyl), —OS(O)$_2$—(C$_1$-C$_6$haloalkyl), or —OS(O)$_2$-(para-methylphenyl). In certain other embodiments, R$^1$ is —OS(O)$_2$CH$_3$, —OS(O)$_2$CF$_3$, or —OS(O)$_2$-(para-methylphenyl). In certain other embodiments, R$^1$ is —OC(O)CF$_3$.

In certain embodiments, R$^2$ and R$^3$ are hydrogen.
In certain embodiments, R$^4$ is hydrogen, methyl, ethyl, propyl, butyl, or pentyl. In certain other embodiments, R$^4$ is methyl, ethyl or propyl. In certain other embodiments, R$^4$ is methyl.

1 In certain embodiments, R$^5$ is hydrogen or methyl. In certain other embodiments, R$^5$ is hydrogen.

The description above describes multiple embodiments relating to compounds of Formula II-A. The patent application specifically contemplates all combinations of the embodiments. For example, the invention contemplates a compound of Formula II-A wherein A is —N(R$^5$)—, and R$^2$ and R$_3$ are hydrogen.

In certain embodiments, the therapeutic agent is a hemoglobin conjugate of Formula III, and said therapeutic agent is administered by injection (such as intravenous injection).

In certain embodiments, A$^1$ is —C(O)— and A$^2$ is N.
In certain embodiments, n is 0, and m is 2.
In certain embodiments, the therapeutic agent is

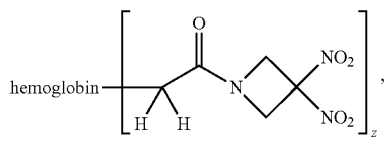

or a pharmaceutically acceptable salt thereof, where z is an integer from 1 to 10.

The therapeutic agents of Formulae I and II can be prepared based on the procedures described in Schemes 1-9 above. The hemoglobin conjugates of Formulae III and IV can be prepared by admixing hemoglobin and a therapeutic agent of Formulae I and II, respectively, to form the hemoglobin conjugate. In certain embodiments, the beta-cysteine-93 residue of hemoglobin reacts with the therapeutic agents of Formulae I and II form a thioether bond due to reaction of the thiol group of the beta-cysteine-93 residue of hemoglobin with the carbon atom bearing the R$^1$ group in Formulae I and II.

V. Treating Patients with Anemia

One aspect of the invention provides a method of treating a patient suffering from anemia. The method comprises administering to a patient in need thereof a therapeutic agent selected from the group consisting of an organonitro compound of Formula I, organonitro compound of Formula II, hemoglobin conjugate of Formula III, hemoglobin conjugate of Formula IV, and an erythrocyte cell that has been exposed to an organonitro compound of Formula I or II; wherein Formula I is represented by:

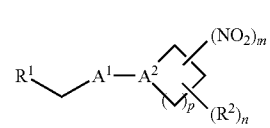

(I)

or a pharmaceutically acceptable salt or solvate thereof, wherein:

A$^1$ is —C(O)— or —(C(R$^2$)$_2$)$_x$C(O)(C(R$^3$)$_2$)$_x$—;
A$^2$ is N or —C(R$^4$)—;
R$^1$ is halogen, —OS(O)$_2$R$^5$, or —OC(O)CF$_3$;
R$^2$ is C$_1$-C$_6$alkyl;
R$^3$ and R$^4$ each represent independently for each occurrence hydrogen or C$_1$-C$_5$alkyl;
R$_5$ is C$_1$-C$_6$alkyl, C$_1$-C$_6$haloalkyl, aryl, or aralkyl;
m and p are independently 1, 2, or 3; and
n and x each represent independently for each occurrence 0, 1, 2, or 3; Formula II is represented by:

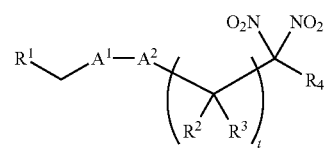

(II)

or a pharmaceutically acceptable salt or solvate thereof: wherein:

A$^1$ is —C(O)— or —(C(R$^5$)$_2$)$_x$C(O)(C(R$^5$)$_2$)$_x$—;
A$^2$ is —N(R$^5$)— or —C(R$^2$)(R$^3$)—;
R$^1$ is halogen, —OS(O)$_2$R$^6$, or —OC(O)CF$_3$;
R$^2$ and R$^3$ each represent independently for each occurrence hydrogen or C$_1$-C$_6$alkyl; or
R$^2$ and R$^3$ are taken together with the carbon atom to which they are attached to form a 3-6 membered, saturated carbocyclic ring;
R$^4$ is hydrogen or C$_1$-C$_5$alkyl;
R$^5$ represents independently for each occurrence hydrogen or C$_1$-C$_6$alkyl;
R$^6$ is C$_1$-C$_6$alkyl, C$_1$-C$_6$haloalkyl, aryl, or aralkyl;
t is an integer in the range from 1 to 12; and x represents independently for each occurrence 0, 1, 2, or 3;
Formula III is represented by:

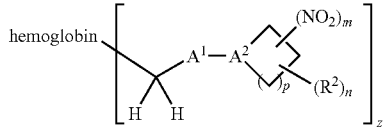

or a pharmaceutically acceptable salt or solvate thereof, wherein:
$A^1$ is —C(O)— or —C(O)(C($R^3$)$_2$)$_x$—;
$A^2$ is N or —C($R^4$)—;
$R^2$ is $C_1$-$C_6$alkyl
$R^3$ and $R^4$ each represent independently for each occurrence hydrogen or $C_1$-$C_5$alkyl;
m and p are independently 1, 2, or 3;
n is 0, 1, 2, or 3;
x is 1, 2, or 3; and
z is an integer from 1 to 10; and
Formula IV is represented by:

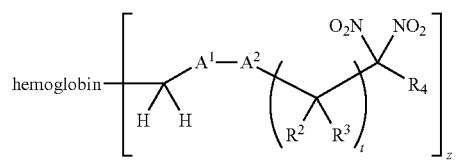

or a pharmaceutically acceptable salt or solvate thereof, wherein:
$A^1$ is —C(O)— or —C(O)(C($R^5$)$_2$)$_x$—;
$A^2$ is —N($R^5$)— or —C($R^2$)($R^3$)—;
$R^2$ and $R^3$ each represent independently for each occurrence hydrogen or $C_1$-$C_6$alkyl; or
$R^2$ and $R^3$ are taken together with the carbon atom to which they are attached to form a 3-6 membered, saturated carbocyclic ring;
$R^4$ is hydrogen or $C_1$-$C_6$alkyl;
$R^5$ represents independently for each occurrence hydrogen or $C_1$-$C_6$alkyl;
t is an integer in the range from 1 to 12;
x is 1, 2, or 3; and
z is an integer from 1 to 10.

In certain embodiments, the method further comprises administering a blood product to the patient by injection (such as intravenous injection).

In certain embodiments, the blood product comprises erythrocyte cells. In certain other embodiments, the blood product comprises blood plasma. In certain embodiments, the blood product comprises erythrocyte cells and blood plasma.

In certain embodiments, the blood product and organonitro compound are administered to the patient concurrently. In certain other embodiments, the blood product is administered to the patient separately from the therapeutic agent.

In certain embodiments, the patient receives, by intravenous injection, a single composition comprising blood product and the therapeutic agent. In certain other embodiments, the patient receives, by intravenous injection, a single composition comprising a therapeutic agent, plasma, and erythrocyte cells. One exemplary composition is provided below in Table 2.

TABLE 2

Exemplary Composition for Intravenous Injection*

| Component | Amount |
|---|---|
| Erythrocyte cells (vol %) | 35-60 |
| Plasma (mL) | 17 |
| Anticoagulant | As needed (e.g., 4 mL) |
| Therapeutic Agent (e.g., ABDNAZ) | As needed, such as, an amount to treat hemorrhagic shock. |

*Amounts are based on a composition having a total volume of 282 mL.

In certain embodiments, the method further comprises administering an alkali metal nitrite to the patient. In other embodiments, the method further comprises administering sodium nitrite to the patient.

In certain embodiments, the therapeutic agent is an organonitro compound of Formula I. In certain other embodiments, the therapeutic agent is an erythrocyte cell that has been exposed to an organonitro compound of Formula I, and said therapeutic agent is administered by injection (such as intravenous injection).

In certain embodiments, $A^1$ is —C(O)—, and $A^2$ is N.
In certain embodiments, $R^1$ is bromo.
In certain embodiments, n is 0, and m is 2.

The description above describes multiple embodiments relating to compounds of Formula I. The patent application specifically contemplates all combinations of the embodiments. For example, the invention contemplates a compound of Formula I wherein $A^1$ is —C(O)—, $A^2$ is N, $R^1$ is halogen, and n is 0.

In certain embodiments, the therapeutic agent is a compound of Formula I-A:

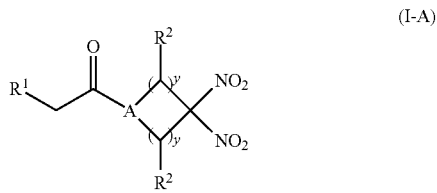

or a pharmaceutically acceptable salt or solvate thereof, wherein:
A is N or C(H);
$R^1$ is chloro, bromo, —OS(O)$_2$—($C_1$-$C_6$alkyl), —OS(O)$_2$—($C_1$-$C_6$haloalkyl), —OS(O)$_2$-(para-methylphenyl), or —OC(O)CF$_3$;
$R^2$ represents independently for each occurrence hydrogen or methyl; and
y represents independently for each occurrence 1 or 2.

In certain embodiments, the therapeutic agent is compound embraced by Formula I-A as defined by particular definitions for variables in Formula I-A, such as where A is N. In certain other embodiments, A is C(H).

In certain embodiments, $R^1$ is chloro or bromo. In certain embodiments, $R^1$ is chloro. In certain other embodiments, $R^1$ is bromo. In certain embodiments, $R^1$ is —OS(O)$_2$—($C_1$-$C_6$alkyl), —OS(O)$_2$—($C_1$-$C_6$haloalkyl), or —OS(O)$_2$-(para-methylphenyl). In certain other embodiments, $R^1$ is —OS (O)$_2$CH$_3$, —OS(O)$_2$CF$_3$, or —OS(O)$_2$-(para-methylphenyl) In certain other embodiments, R$_1$ is —OC(O)CF$_3$.

In certain embodiments, R$^2$ is hydrogen or methyl. In certain embodiments, R$^2$ is hydrogen.

In certain embodiments, y is 1. In certain embodiments, one occurrence of y is 1, and the other occurrence of y is 2. In certain other embodiments, y is 2.

The description above describes multiple embodiments relating to compounds of Formula I-A. The patent application specifically contemplates all combinations of the embodiments. For example, the invention contemplates a compound of Formula I-A wherein A is N, R$^1$ is chloro or bromo, and R$^2$ is hydrogen.

In certain embodiments, the therapeutic agent is

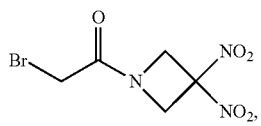

or a pharmaceutically acceptable salt thereof.

In certain embodiments, the therapeutic agent an organonitro compound embraced by Formula II as defined by particular definitions for variables in Formula II, such as where A$^1$ is —C(O)—. In certain other embodiments, A$^1$ is —(C(R$^5$)$_2$)$_x$C(O)(C(R$^5$)$_2$)$_x$—. In certain other embodiments, A$^1$ is —C(O)(C(R$^5$)$_2$)$_x$—.

In certain embodiments, A$^2$ is —N(R$^5$)—. In certain other embodiments, A$^2$ is —C(R$^2$)(R$^3$)—.

In certain embodiments, R$^1$ is halogen. In certain other embodiments, R$^1$ is —OS(O)$_2$R$^6$. In certain other embodiments, R$^1$ is —OC(O)CF$_3$. In certain other embodiments, R$^1$ is chloro, bromo, —OS(O)$_2$-(para-methylphenyl), —OS(O)$_2$CH$_3$, —OS(O)$_2$CF$_3$, or —OC(O)CF$_3$. In certain embodiments, R$^1$ is bromo.

In certain embodiments, R$^2$ and R$^3$ each represent independently for each occurrence hydrogen or C$_1$-C$_6$alkyl. In certain other embodiments, R$^2$ and R$^3$ each represent independently for each occurrence hydrogen, methyl, ethyl, or propyl. In certain other embodiments, R$^2$ and R$^3$ each represent independently for each occurrence hydrogen or methyl. In certain embodiments, R$^2$ and R$^3$ are hydrogen.

In certain embodiments, R$^4$ is hydrogen, methyl, ethyl, propyl, butyl, or pentyl. In certain other embodiments, R$^4$ is methyl, ethyl or propyl. In certain other embodiments, R$^4$ is methyl.

In certain embodiments, R$^5$ is hydrogen or methyl. In certain other embodiments, R$^5$ is hydrogen.

In certain embodiments, R$^6$ is C$_1$-C$_6$alkyl or C$_1$-C$_6$haloalkyl. In certain other embodiments, R$^6$ is methyl, ethyl, or trifluoromethyl. In certain other embodiments, R$^6$ is aryl, such as phenyl.

In certain embodiments, t is 1, 2, 3, 4, 5 or 6. In certain other embodiments, t is 1, 2, or 3. In certain other embodiments, t is 1. In certain embodiments, x is 1 or 2.

The description above describes multiple embodiments relating to compounds of Formula II. The patent application specifically contemplates all combinations of the embodiments. For example, the invention contemplates a compound of Formula II wherein A$^1$ is —C(O)—, A$^2$ is —N(R$^5$)—, and R$^2$ and R$^3$ are hydrogen.

In certain embodiments, the therapeutic agent is a compound of Formula II-A:

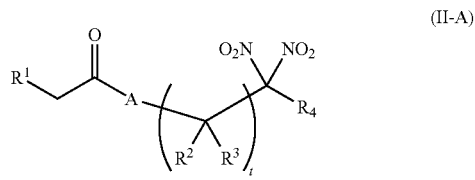

or a pharmaceutically acceptable salt or solvate thereof: wherein:
A is —N(R$^5$)— or —C(R$^2$)(R$^3$)—;
R$^1$ is chloro, bromo, —OS(O)$_2$—(C$_1$-C$_6$alkyl), —OS(O)$_2$—(C$_1$-C$_6$haloalkyl), —OS(O)$_2$-(para-methylphenyl), or —OC(O)CF$_3$;
R$^2$, R$^3$, and R$^5$ each represent independently for each occurrence hydrogen or methyl;
R$^4$ is hydrogen or C$_1$-C$_6$alkyl; and
t is 1, 2, or 3.

In certain embodiments, the therapeutic agent is an organonitro compound embraced by Formula II-A as defined by particular definitions for variables in Formula II-A, such as where A is —N(R$^5$)—. In certain other embodiments, A is —N(CH$_3$)—. In certain other embodiments, A is —C(R$^2$)(R$^3$)—. In certain other embodiments, A is —CH$_2$—.

In certain embodiments, R$^1$ is chloro. In certain other embodiments, R$^1$ is bromo. In certain embodiments, R$^1$ is —OS(O)$_2$—(C$_1$-C$_6$alkyl), —OS(O)$_2$—(C$_1$-C$_6$haloalkyl), or —OS(O)$_2$-(para-methylphenyl). In certain other embodiments, R$^1$ is —OS(O)$_2$CH$_3$, —OS(O)$_2$CF$_3$, or —OS(O)$_2$-(para-methylphenyl). In certain other embodiments, R$^1$ is —OC(O)CF$_3$.

In certain embodiments, R$^2$ and R$^3$ are hydrogen.

In certain embodiments, R$^4$ is hydrogen, methyl, ethyl, propyl, butyl, or pentyl. In certain other embodiments, R$^4$ is methyl, ethyl or propyl. In certain other embodiments, R$^4$ is methyl.

In certain embodiments, R$^5$ is hydrogen or methyl. In certain other embodiments, R$^5$ is hydrogen.

The description above describes multiple embodiments relating to compounds of Formula II-A. The patent application specifically contemplates all combinations of the embodiments. For example, the invention contemplates a compound of Formula II-A wherein A is —N(R$^5$)—, and R$^2$ and R$^3$ are hydrogen.

In certain embodiments, the therapeutic agent is a hemoglobin conjugate of Formula iii, and said therapeutic agent is administered by injection (such as intravenous injection).

In certain embodiments, A$^1$ is —C(O)— and A$^2$ is N.

In certain embodiments, n is 0, and m is 2.

In certain embodiments, the therapeutic agent is

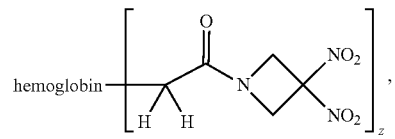

or a pharmaceutically acceptable salt thereof where z is an integer from 1 to 10.

The therapeutic agents of Formulae I and II can be prepared based on the procedures described in Schemes 1-9 above. The hemoglobin conjugates of Formulae III and IV can be prepared by admixing hemoglobin and a therapeutic agent of Formulae I and II, respectively, to form the hemoglobin conjugate. In certain embodiments, the beta-cysteine-93 residue of hemoglobin reacts with the therapeutic agents of Formulae I and II form a thioether bond due to reaction of the thiol group of the beta-cysteine-93 residue of hemoglobin with the carbon atom bearing the $R^1$ group in Formulae I and II.

VI. Preserving Blood Products

One aspect of the invention provides a method of preserving an isolated blood product. The method comprises exposing the isolated blood product to an agent selected from the group consisting of an organonitro compound of Formula I, organonitro compound of Formula II, hemoglobin conjugate of Formula III, hemoglobin conjugate of Formula IV, and an erythrocyte cell that has been exposed to an organonitro compound of Formula I or II, wherein Formula I is represented by:

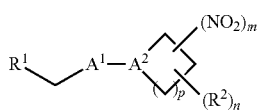

or a pharmaceutically acceptable salt or solvate thereof, wherein:
$A^1$ is —C(O)— or —(C(R$^3$)$_2$)$_x$C(O)(C(R$^3$)$_2$)$_x$—;
$A^2$ is N or —C(R$^4$)—;
$R^1$ is halogen, —OS(O)R$^5$, or —OC(O)CF$_3$;
$R^2$ is $C_1$-$C_6$alkyl;
$R^3$ and $R^4$ each represent independently for each occurrence hydrogen or $C_1$-$C_5$alkyl;
$R^5$ is $C_1$-$C_6$alkyl, $C_1$-$C_6$haloalkyl, aryl, or aralkyl;
m and p are independently 1, 2, or 3; and
n and x each represent independently for each occurrence 0, 1, 2, or 3;
Formula II is represented by:

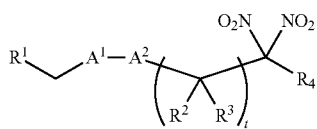

or a pharmaceutically acceptable salt or solvate thereof:
wherein:
$A^1$ is —C(O)— or —(C(R$^5$)$_2$)$_x$C(O)(C(R$^5$)$_2$)$_x$—;
$A^2$ is —N(R$^5$)— or —C(R$^2$)(R$^3$)—;
$R^1$ is halogen, —OS(O)$_2$R$^6$, or —OC(O)CF$_3$;
$R^2$ and $R^3$ each represent independently for each occurrence hydrogen or $C_1$-$C_6$alkyl; or $R^2$ and $R^3$ are taken together with the carbon atom to which they are attached to form a 3-6 membered, saturated carbocyclic ring;
$R^4$ is hydrogen or $C_1$-$C_6$alkyl;
$R^5$ represents independently for each occurrence hydrogen or $C_1$-$C_6$alkyl;
$R^6$ is $C_1$-$C_6$alkyl, $C_1$-$C_6$haloalkyl, aryl, or aralkyl;
t is an integer in the range from 1 to 12; and x represents independently for each occurrence 0, 1, 2, or 3;
Formula III is represented by:

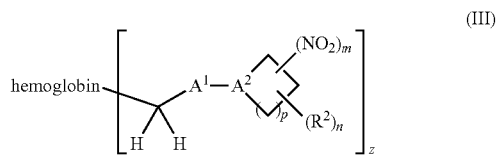

or a pharmaceutically acceptable salt or solvate thereof, wherein:
$A^1$ is —C(O)— or —C(O)(C(R$^3$)$_2$)$_x$—;
$A^2$ is N or —C(R$^4$)—;
$R^2$ is $C_1$-$C_6$alkyl;
$R^3$ and $R^4$ each represent independently for each occurrence hydrogen or $C_1$-$C_5$alkyl;
m and p are independently 1, 2, or 3;
n is 0, 1, 2, or 3;
x is 1, 2, or 3; and
z is an integer from 1 to 10; and
Formula IV is represented by:

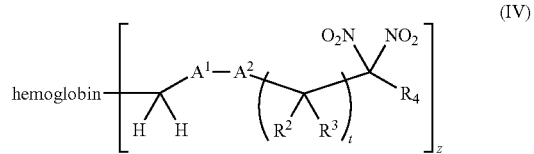

or a pharmaceutically acceptable salt or solvate thereof, wherein:
$A^1$ is —C(O)— or —C(O)(C(R$^5$)$_2$)$_x$—;
$A^2$ is —N(R$^5$)— or —C(R$^2$)(R$^3$)—;
$R^2$ and $R^3$ each represent independently for each occurrence hydrogen or $C_1$-$C_6$alkyl; or $R^2$ and $R^3$ are taken together with the carbon atom to which they are attached to form a 3-6 membered, saturated carbocyclic ring;
$R^4$ is hydrogen or $C_1$-$C_6$alkyl;
$R^5$ represents independently for each occurrence hydrogen or $C_1$-$C_6$alkyl;
t is an integer in the range from 1 to 12;
x is 1, 2, or 3; and
z is an integer from 1 to 10.

In certain embodiments, the isolated blood product is whole blood. In certain embodiments, the isolated blood product comprises erythrocyte cells. In certain other embodiments, the isolated blood product is erythrocyte cells.

In certain embodiments, the method further comprises exposing the isolated blood product to an alkali metal nitrite. In other further embodiments, the method comprises exposing the isolated blood product to sodium nitrite.

In certain embodiments, the agent is an organonitro compound of Formula I. In certain embodiments, the agent is an erythrocyte cell that has been exposed to an organonitro compound of Formula I.

In certain embodiments, $A^1$ is —C(O)—, and $A^2$ is N.
In certain embodiments, $R^1$ is bromo.
In certain embodiments, n is 0, and m is 2.

The description above describes multiple embodiments relating to compounds of Formula I. The patent application specifically contemplates all combinations of the embodiments. For example, the invention contemplates a compound of Formula I wherein $A^1$ is —C(O)—, $A^2$ is N, $R^1$ is halogen, and n is 0.

In certain embodiments, the agent is a compound of Formula I-A:

$$\text{(I-A)}$$

or a pharmaceutically acceptable salt or solvate thereof, wherein:
A is N or C(H);
$R^1$ is chloro, bromo, —OS(O)$_2$—(C$_1$-C$_6$alkyl), —OS(O)$_2$—(C$_1$-C$_6$haloalkyl), —OS(O)$_2$-(para-methylphenyl), or —OC(O)CF$_3$;
$R^2$ represents independently for each occurrence hydrogen or methyl; and
y represents independently for each occurrence 1 or 2.

In certain embodiments, the agent is compound embraced by Formula I-A as defined by particular definitions for variables in Formula I-A, such as where A is N. In certain other embodiments, A is C(H).

In certain embodiments, $R^1$ is chloro or bromo. In certain embodiments, $R^1$ is chloro. In certain other embodiments, $R^1$ is bromo. In certain embodiments, $R^1$ is —OS(O)$_2$—(C$_1$-C$_6$alkyl), —OS(O)$_2$—(C$_1$-C$_6$haloalkyl), or —OS(O)$_2$-(para-methylphenyl). In certain other embodiments, $R^1$ is —OS(O)$_2$CH$_3$, —OS(O)$_2$CF$_3$, or —OS(O)$_2$-(para-methylphenyl). In certain embodiments, $R^1$ is —OC(O)CF$_3$.

In certain embodiments, $R^2$ is hydrogen or methyl. In certain embodiments, $R^2$ is hydrogen.

In certain embodiments, y is 1. In certain embodiments, one occurrence of y is 1, and the other occurrence of y is 2. In certain other embodiments, y is 2.

The description above describes multiple embodiments relating to compounds of Formula I-A. The patent application specifically contemplates all combinations of the embodiments. For example, the invention contemplates a compound of Formula I-A wherein A is N, $R^1$ is chloro or bromo, and $R^2$ is hydrogen.

In certain embodiments, the agent is $$\text{structure with Br, N, NO}_2, \text{NO}_2$$

or a pharmaceutically acceptable salt thereof.

In certain embodiments, the agent an organonitro compound embraced by Formula II as defined by particular definitions for variables in Formula II, such as where $A^1$ is —C(O)—. In certain other embodiments, $A^1$ is —(C(R$^5$)$_2$)$_x$—C(O)(C(R$_5$)$_2$)$_x$—. In certain other embodiments, $A^1$ is —C(O)(C(R$^5$)$_2$)$_x$—.

In certain embodiments, $A^2$ is —N(R$^5$)—. In certain other embodiments, $A^2$ is —C(R$^2$)(R$^3$)—.

In certain embodiments, $R^1$ is halogen. In certain other embodiments, $R^1$ is —OS(O)$_2$R$^6$. In certain other embodiments, $R^1$ is —OC(O)CF$_3$. In certain other embodiments, $R^1$ is chloro, bromo, —OS(O)-para-methylphenyl), —OS(O)$_2$CH$_3$, —OS(O)$_2$CF$_3$, or —OC(O)CF$_3$. In certain embodiments, $R^1$ is bromo.

In certain embodiments, $R^2$ and $R^3$ each represent independently for each occurrence hydrogen or C$_1$-C$_6$alkyl. In certain other embodiments, $R^2$ and $R^3$ each represent independently for each occurrence hydrogen, methyl, ethyl, or propyl. In certain other embodiments, $R^2$ and $R^3$ each represent independently for each occurrence hydrogen or methyl. In certain embodiments, $R^2$ and $R^3$ are hydrogen.

In certain embodiments, $R^4$ is hydrogen, methyl, ethyl, propyl, butyl, or pentyl. In certain other embodiments, $R^4$ is methyl, ethyl or propyl. In certain other embodiments, $R^4$ is methyl.

In certain embodiments, $R^5$ is hydrogen or methyl. In certain other embodiments, $R^5$ is hydrogen.

In certain embodiments, $R^6$ is C$_1$-C$_6$alkyl or C$_1$-C$_6$haloalkyl. In certain other embodiments, $R^6$ is methyl, ethyl, or trifluoromethyl. In certain other embodiments, $R^6$ is aryl, such as phenyl.

In certain embodiments, t is 1, 2, 3, 4, 5 or 6. In certain other embodiments, t is 1, 2, or 3. In certain other embodiments, t is 1. In certain embodiments, x is 1 or 2.

The description above describes multiple embodiments relating to compounds of Formula II. The patent application specifically contemplates all combinations of the embodiments. For example, the invention contemplates a compound of Formula II wherein $A^1$ is —C(O)—, $A^2$ is —N(R$^5$)—, and $R^2$ and $R^3$ are hydrogen.

In certain embodiments, the agent is a compound of Formula II-A:

$$\text{(II-A)}$$

or a pharmaceutically acceptable salt or solvate thereof:
wherein:
A is —N(R$^5$)— or —C(R$^2$)(R$^3$)—;
$R^1$ is chloro, bromo, —OS(O)$_2$—(C$_1$-C$_6$alkyl), —OS(O)$_2$—(C$_1$-C$_6$haloalkyl), —OS(O)$_2$-(para-methylphenyl), or —OC(O)CF$_3$;
$R^2$, $R^3$, and $R^5$ each represent independently for each occurrence hydrogen or methyl;
$R^4$ is hydrogen or C$_1$-C$_6$alkyl; and
t is 1, 2, or 3.

In certain embodiments, the agent is an organonitro compound embraced by Formula II-A as defined by particular definitions for variables in Formula II-A, such as where A is —N(R$^5$)—. In certain other embodiments, A is —N(CH$_3$)—. In certain other embodiments, A is —C(R$^2$)(R$^3$)—. In certain other embodiments, A is —CH$_2$—.

In certain embodiments, $R^1$ is chloro. In certain other embodiments, $R^1$ is bromo. In certain embodiments, $R^1$ is —OS(O)$_2$—(C$_1$-C$_6$alkyl), —OS(O)$_2$—(C$_1$-C$_6$haloalkyl), or —OS(O)$_2$-(para-methylphenyl). In certain other embodiments, $R^1$ is —OS(O)$_2$CH$_3$, —OS(O)$_2$CF$_3$, or —OS(O)$_2$-(para-methylphenyl). In certain embodiments, $R^1$ is —OC(O)CF$_3$.

In certain embodiments, $R^2$ and $R^3$ are hydrogen.

In certain embodiments, $R^4$ is hydrogen, methyl, ethyl, propyl, butyl, or pentyl. In certain other embodiments, $R^4$ is methyl, ethyl or propyl. In certain other embodiments, $R^4$ is methyl.

In certain embodiments, $R^5$ is hydrogen or methyl. In certain other embodiments, $R^5$ is hydrogen.

The description above describes multiple embodiments relating to compounds of Formula II-A. The patent application specifically contemplates all combinations of the embodiments. For example, the invention contemplates a compound of Formula II-A wherein A is —N($R^5$)—, and $R^2$ and $R^3$ are hydrogen.

In certain embodiments, the agent is a hemoglobin conjugate of Formula III.

In certain embodiments, $A^1$ is —C(O)— and $A^2$ is N.

In certain embodiments, n is 0, and m is 2.

In certain embodiments, the agent is

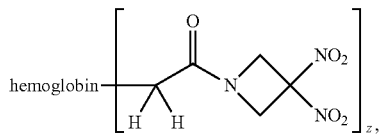

pharmaceutically acceptable salt thereof, where z is an integer from 1 to 10.

In certain embodiments, the agent is provided in an amount effective to extend the storage life of the blood product by at least 10%, 20% or 30% relative to the storage life of the blood product without the agent. For example, in certain embodiments, the agent is provided in an amount effective to extend the storage life of the blood product by at least 1 day, 5 days, 10 days, or 15 days.

The agents of Formulae I and II can be prepared based on the procedures described in Schemes 1-9 above. The hemoglobin conjugates of Formulae III and IV can be prepared by admixing hemoglobin and an agent of Formulae I and II, respectively, to form the hemoglobin conjugate. In certain embodiments, the beta-cysteine-93 residue of hemoglobin reacts with the agents of Formulae I and II form a thioether bond due to reaction of the thiol group of the beta-cysteine-93 residue of hemoglobin with the carbon atom bearing the $R^1$ group in Formulae I and IL.

ABDNAZ and other compounds described herein are believed to ameliorate the well-known storage lesion that occurs with stored blood. Nitric oxide (NO)) bioactivity of stored blood decreases rapidly after blood is removed from the organism, which in part limits the ability of stored blood to reverse arteriolar vasoconstriction, capillary perfusion and tissue hypoxia. These stresses consequently may affect the degree of intra and extravascular hemolysis post-transfusion. Low levels of hemoglobin (Hb) in plasma severely disrupt NO bioavailability by accelerating NO dioxygenation reactions which results in decreased NO concentration and leads to vasoconstriction. Restoration of NO bioavailability prior or concurrently with the transfusion strategy may therefore reduce the morbidity and mortality associated with blood transfusion. Furthermore, enhancing the ability of blood to generate NO by incubation with ABDNAZ or other compounds herein may decrease the number of units of blood needed for treatment and reduce healthcare costs while also extending the shelf life of packed blood.

VII. Isolated Blood Product Compositions

Another aspect of the invention provides an isolated blood product composition. The composition comprises (i) a blood product, and (ii) an agent selected from the group consisting of an organonitro compound of Formula I, organonitro compound of Formula II, hemoglobin conjugate of Formula III, hemoglobin conjugate of Formula IV, and an erythrocyte cell that has been exposed to an organonitro compound of Formula I or II; wherein Formula I is represented by:

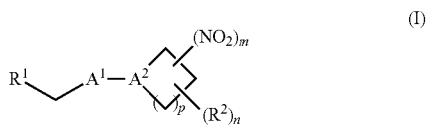

or a pharmaceutically acceptable salt or solvate thereof, wherein:

$A^1$ is —C(O)— or —(C($R^3$)$_2$)$_x$C(O)(C($R^3$)$_2$)$_x$—;
$A^2$ is N or —C($R^4$)—;
$R^1$ is halogen, —OS(O)$_2R^5$, or —OC(O)CF$_3$;
$R^2$ is $C_1$-$C_6$alkyl;
$R^3$ and $R^4$ each represent independently for each occurrence hydrogen or $C_1$-$C_5$alkyl;
$R^5$ is $C_1$-$C_6$alkyl, $C_1$-$C_6$haloalkyl, aryl, or aralkyl;
m and p are independently 1, 2, or 3; and
n and x each represent independently for each occurrence 0, 1, 2, or 3;

Formula II is represented by:

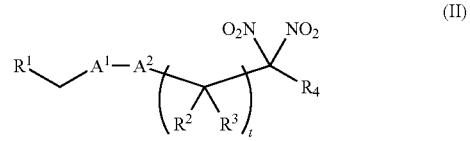

or a pharmaceutically acceptable salt or solvate thereof: wherein:

$A^1$ is —C(O)— or —(C($R^5$)$_2$)$_x$C(O)(C($R^5$)$_2$)$_x$—;
$A^2$ is —N($R^5$)— or —C($R^2$)($R^3$)—;
$R^1$ is halogen, —OS(O)$_2R^6$, or —OC(O)CF$_3$;
$R^2$ and $R^3$ each represent independently for each occurrence hydrogen or $C_1$-$C_6$alkyl; or $R_2$ and $R^3$ are taken together with the carbon atom to which they are attached to form a 3-6 membered, saturated carbocyclic ring;
$R^4$ is hydrogen or $C_1$-$C_6$alkyl;
$R^5$ represents independently for each occurrence hydrogen or $C_1$-$C_6$alkyl;
$R^6$ is $C_1$-$C_6$alkyl, $C_1$-$C_6$haloalkyl, aryl, or aralkyl;
t is an integer in the range from 1 to 12; and
x represents independently for each occurrence 0, 1, 2, or 3;

Formula III is represented by:

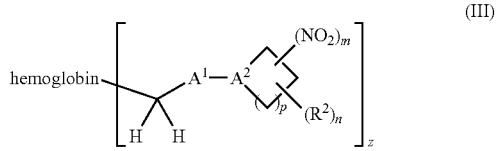

or a pharmaceutically acceptable salt or solvate thereof, wherein:

$A^1$ is —C(O)— or —C(O)(C($R^3$)$_2$)$_x$—;
$A^2$ is N or —C($R^4$)—;

$R^2$ is $C_1$-$C_6$alkyl;
$R^3$ and $R^4$ each represent independently for each occurrence hydrogen or $C_1$-$C_5$alkyl;
m and p are independently 1, 2, or 3;
n is 0, 1, 2, or 3;
x is 1, 2, or 3; and
z is an integer from 1 to 10; and
Formula IV is represented by:

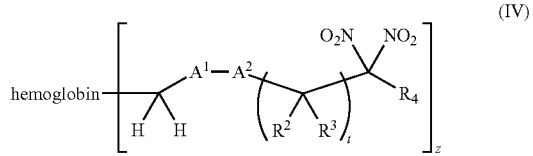

or a pharmaceutically acceptable salt or solvate thereof wherein:
$A^1$ is —C(O)— or —C(O)(C($R^5$)$_2$)$_x$—;
$A^2$ is —N($R^5$)— or —C($R^2$)($R^3$)—;
$R^2$ and $R^3$ each represent independently for each occurrence hydrogen or $C_1$-$C_6$alkyl; or $R^2$ and $R^3$ are taken together with the carbon atom to which they are attached to form a 3-6 membered, saturated carbocyclic ring;
$R^4$ is hydrogen or $C_1$-$C_6$alkyl;
$R^5$ represents independently for each occurrence hydrogen or $C_1$-$C_6$alkyl;
t is an integer in the range from 1 to 12;
x is 1, 2, or 3; and
z is an integer from 1 to 10.

In certain embodiments, the blood product is whole blood. In certain embodiments, the blood product comprises erythrocyte cells. In certain other embodiments, the blood product comprises erythrocyte cells and blood plasma. In certain embodiments, the blood product is erythrocyte cells.

In certain embodiments, the composition further comprises an alkali metal nitrite. In certain other embodiments, the composition further comprises sodium nitrite.

The description above describes multiple embodiments relating to compounds of Formula I. The patent application specifically contemplates all combinations of the embodiments. For example, the invention contemplates a compound of Formula I wherein A is —C(O)—, $A^2$ is N, $R^1$ is halogen, and n is 0.

In certain embodiments, the agent is a compound of Formula I-A:

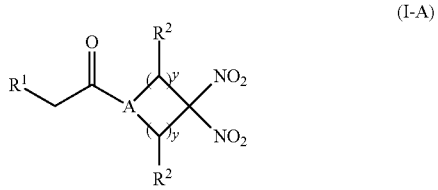

or a pharmaceutically acceptable salt or solvate thereof, wherein:
A is N or C(H);
$R^1$ is chloro, bromo, —OS(O)$_2$—($C_1$-$C_6$alkyl), —OS(O)$_2$—($C_1$-$C_6$haloalkyl), —OS(O)$_2$-(para-methylphenyl), or —OC(O)CF$_3$;

$R^1$ represents independently for each occurrence hydrogen or methyl; and
y represents independently for each occurrence 1 or 2.

In certain embodiments, the agent is compound embraced by Formula I-A as defined by particular definitions for variables in Formula I-A, such as where A is N. In certain other embodiments, A is C(H).

In certain embodiments, $R^1$ is chloro or bromo. In certain embodiments, $R^1$ is chloro. In certain other embodiments, $R^1$ is bromo. In certain embodiments, $R^1$ is —OS(O)$_2$—($C_1$-$C_6$alkyl), —OS(O)$_2$—($C_1$-$C_6$haloalkyl), or —OS(O)$_2$-(para-methylphenyl). In certain other embodiments, $R^1$ is —OS(O)$_2$CH$_3$, —OS(O)$_2$CF$_3$, or —OS(O)$_2$-(para-methylphenyl). In certain other embodiments, $R^1$ is —OC(O)CF$_3$.

In certain embodiments, $R^2$ is hydrogen or methyl. In certain embodiments, $R^2$ is hydrogen.

In certain embodiments, y is 1. In certain embodiments, one occurrence of y is 1, and the other occurrence of y is 2. In certain other embodiments, y is 2.

The description above describes multiple embodiments relating to compounds of Formula I-A. The patent application specifically contemplates all combinations of the embodiments. For example, the invention contemplates a compound of Formula I-A wherein A is N, $R^1$ is chloro or bromo, and $R^2$ is hydrogen.

In certain embodiments, the agent is

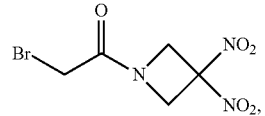

or a pharmaceutically acceptable salt thereof.

In certain embodiments, the agent an organonitro compound embraced by Formula II as defined by particular definitions for variables in Formula II, such as where $A^1$ is —C(O)—. In certain other embodiments, $A^1$ is —(C($R^5$)$_2$)$_x$C(O)(C($R^5$)$_2$)$_x$—. In certain other embodiments, $A^1$ is —C(O)(C($R^5$)$_2$)$_x$—.

In certain embodiments, $A^2$ is —N($R^5$)—. In certain other embodiments, $A^2$ is —C($R^2$)($R^3$)—.

In certain embodiments, $R^1$ is halogen. In certain other embodiments, $R^1$ is —OS(O)$_2$$R^6$. In certain other embodiments, $R^1$ is —OC(O)CF$_3$. In certain other embodiments, $R^1$ is chloro, bromo, —OS(O)$_2$-(para-methylphenyl), —OS(O)$_2$CH$_3$, —OS(O)$_2$CF$_3$, or —OC(O)CF$_3$. In certain embodiments, $R^1$ is bromo.

In certain embodiments, $R^2$ and $R^3$ each represent independently for each occurrence hydrogen or $C_1$-$C_6$alkyl. In certain other embodiments, $R^2$ and $R^3$ each represent independently for each occurrence hydrogen, methyl, ethyl, or propyl. In certain other embodiments, $R^2$ and $R^3$ each represent independently for each occurrence hydrogen or methyl. In certain embodiments, $R^2$ and $R^3$ are hydrogen.

In certain embodiments, $R^4$ is hydrogen, methyl, ethyl, propyl, butyl, or pentyl. In certain embodiments, $R^4$ is methyl, ethyl or propyl. In certain embodiments, $R^4$ is methyl.

In certain embodiments, $R^5$ is hydrogen or methyl. In certain embodiments, $R^5$ is hydrogen.

In certain embodiments, $R^6$ is $C_1$-$C_6$alkyl or $C_1$-$C_6$haloalkyl. In certain other embodiments, $R^6$ is methyl, ethyl, or trifluoromethyl. In certain other embodiments, $R^6$ is aryl, such as phenyl.

In certain embodiments, t is 1, 2, 3, 4, 5 or 6. In certain other embodiments, t is 1, 2, or 3. In certain other embodiments, t is 1. In certain embodiments, x is 1 or 2.

The description above describes multiple embodiments relating to compounds of Formula II. The patent application specifically contemplates all combinations of the embodiments. For example, the invention contemplates a compound of Formula II wherein $A^1$ is —C(O)—, $A^2$ is —N($R^5$)—, and $R^2$ and $R^3$ are hydrogen.

In certain embodiments, the agent is a compound of Formula II-A:

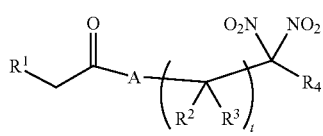

(II-A)

or a pharmaceutically acceptable salt or solvate thereof: wherein:

A is —N($R^5$)— or —C($R^2$)($R^3$)—;

$R^1$ is chloro, bromo, —OS(O)$_2$—($C_1$-$C_6$alkyl), —OS(O)$_2$—($C_1$-$C_6$haloalkyl), —OS(O)$_2$-(para-methylphenyl), or —OC(O)CF$_3$;

$R^2$, $R^3$, and $R^5$ each represent independently for each occurrence hydrogen or methyl;

$R^4$ is hydrogen or $C_1$-$C_6$alkyl; and t is 1, 2 or 3.

In certain embodiments, the agent is an organonitro compound embraced by Formula II-A as defined by particular definitions for variables in Formula II-A, such as where A is —N($R^5$)—. In certain other embodiments, A is —N(CH$_3$)—. In certain other embodiments, A is —C($R^2$)($R^3$)—. In certain other embodiments, A is —CH$_2$—.

In certain embodiments, $R^1$ is chloro. In certain other embodiments, $R^1$ is bromo. In certain embodiments, $R^1$ is —OS(O)$_2$—($C_1$-$C_6$alkyl), —OS(O)$_2$—($C_1$-$C_6$haloalkyl), or —OS(O)$_2$-(para-methylphenyl). In certain other embodiments, $R^1$ is —OS(O)$_2$CH$_3$, —OS(O)$_2$CF$_3$, or —OS(O)$_2$-(para-methylphenyl). In certain other embodiments, $R^1$ is —OC(O)CF$_3$.

In certain embodiments, $R^2$ and $R^3$ are hydrogen.

In certain embodiments, $R^4$ is hydrogen, methyl, ethyl, propyl, butyl, or pentyl. In certain other embodiments, $R^4$ is methyl, ethyl or propyl. In certain other embodiments, $R^4$ is methyl.

In certain embodiments, $R^5$ is hydrogen or methyl. In certain other embodiments, $R^5$ is hydrogen.

The description above describes multiple embodiments relating to compounds of Formula II-A. The patent application specifically contemplates all combinations of the embodiments. For example, the invention contemplates a compound of Formula II-A wherein A is —N($R^5$)—, and $R^2$ and $R^3$ are hydrogen.

In certain embodiments, the agent is a hemoglobin conjugate of Formula III.

In certain embodiments, $A^1$ is —C(O)— and $A^2$ is N.

In certain embodiments, n is 0, and m is 2.

In certain embodiments, the agent is

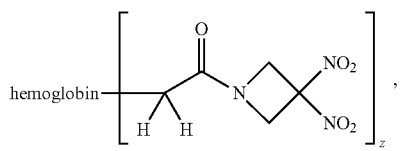

pharmaceutically acceptable salt thereof, where z is an integer from 1 to 10.

The agents of Formulae I and II can be prepared based on the procedures described in Schemes 1-9 above. The hemoglobin conjugates of Formulae III and IV can be prepared by admixing hemoglobin and an agent of Formulae I and II, respectively, to form the hemoglobin conjugate. In certain embodiments, the beta-cysteine-93 residue of hemoglobin reacts with the agents of Formulae I and II form a thioether bond due to reaction of the thiol group of the beta-cysteine-93 residue of hemoglobin with the carbon atom bearing the $R^1$ group in Formulae I and II.

In certain embodiments, the isolated blood product composition comprises a compound of Formula II, plasma, and erythrocyte cells. In certain other embodiments, the isolated blood product composition has the features provided below in Table 3.

TABLE 3

| Exemplary Isolated Blood Product Composition* ||
|---|---|
| Component | Amount |
| Erythrocyte cells (vol %) | 35-60 |
| Plasma (mL) | 17 |
| Anticoagulant | As needed (e.g., 4 mL) |
| Therapeutic Agent (e.g., ABDNAZ) | As needed, such as, an amount to treat hemorrhagic shock. |

*Amounts are based on a composition having a total volume of 282 mL.

VIII. Hemoglobin Conjugates

Another aspect of the invention provides an isolated hemoglobin conjugate represented by Formula III or IV:

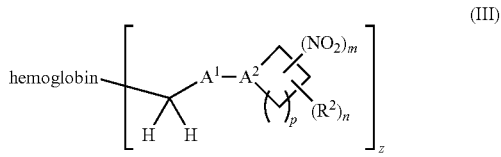

(III)

or a pharmaceutically acceptable salt or solvate thereof, wherein:

$A^1$ is —C(O)— or —C(O)(C($R^3$)$_2$)$_x$—;

$A^2$ is N or —C($R^4$)—;

$R^2$ is $C_1$-$C_6$alkyl;

$R^3$ and $R^4$ each represent independently for each occurrence hydrogen or $C_1$-$C_5$alkyl;

m and p are independently 1, 2, or 3;

n is 0, 1, 2, or 3;

x is 1, 2, or 3; and z is an integer from 1 to 10; and

Formula IV is represented by:

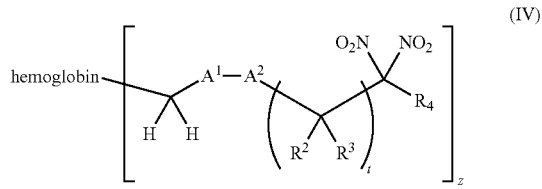

or a pharmaceutically acceptable salt or solvate thereof, wherein:
$A^1$ is —C(O)— or —C(O)(C($R^5$)$_2$)$_x$—;
$A^2$ is —N($R^5$)— or —C($R^2$)($R^3$)—;
$R^2$ and $R^3$ each represent independently for each occurrence hydrogen or $C_1$-$C_6$alkyl; or $R^2$ and $R^3$ are taken together with the carbon atom to which they are attached to form a 3-6 membered, saturated carbocyclic ring;
$R^4$ is hydrogen or $C_1$-$C_6$alkyl;
$R^5$ represents independently for each occurrence hydrogen or $C_1$-$C_6$alkyl;
t is an integer in the range from 1 to 1:2;
x is 1, 2, or 3; and
z is an integer from 1 to 10.

In certain embodiments, the isolated hemoglobin conjugate is represented by Formula III.

In certain embodiments, $A^1$ is —C(O)—, and $A^2$ is N.

In certain embodiments, n is 0, and m is 2.

In certain embodiments, the isolated hemoglobin conjugate is

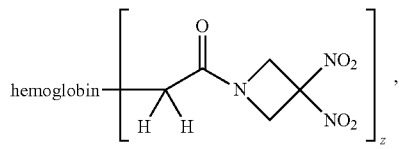

or a pharmaceutically acceptable salt thereof, wherein z is an integer from 1 to 10.

The isolated hemoglobin conjugates of Formulae III and IV can be prepared by admixing hemoglobin and an agent of Formulae I and II, respectively, to form the isolated hemoglobin conjugate. In certain embodiments, the beta-cysteine-93 residue of hemoglobin reacts with the agents of Formulae I and II form a thioether bond due to reaction of the thiol group of the beta-cysteine-93 residue of hemoglobin with the carbon atom bearing the $R^1$ group in Formulae I and II.

In certain embodiments, another aspect of the invention provides a pharmaceutical composition. The composition comprises a pharmaceutically acceptable carrier and an isolated hemoglobin conjugate as described herein. In certain embodiments, the pharmaceutically acceptable carrier comprises blood plasma.

IX. Pharmaceutical Compositions

The invention provides pharmaceutical compositions. As a general matter, the pharmaceutical composition contains at least one active agent and a pharmaceutically acceptable carrier. In certain embodiments, the pharmaceutical compositions comprise an inorganic nitrite salt and/or an allosteric modulator of hemoglobin that promotes nitrite reductase activity. In certain other embodiments, the pharmaceutical compositions preferably comprise a therapeutically-effective amount of an inorganic nitrite salt and/or an allosteric modulator of hemoglobin that promotes nitrite reductase activity, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets (e.g., those targeted for buccal, sublingual, and/or systemic absorption), boluses, powders, granules, pastes for application to the tongue; (2) parenteral administration by, for example, subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders a compound of the present invention orally bioavailable.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia, or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug administered by subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrase "parenteral administration" and "administered parenterally" as used herein means modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal, and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

X. Kits for Use in Medical Applications

Another aspect of the invention provides a kit for treating a disorder. In certain embodiments, the kit comprises: (i) an inorganic nitrite salt, (ii) a nitrite reductase promoter (which preferably is an allosteric modulator of hemoglobin), and (iii) instructions for using the kit to treat a medical disorder.

In certain embodiments, the disorder is cancer, a cardiovascular disorder, an ischemic condition, a hemolytic condition, or a bacterial infection. In certain other embodiments, the disorder is cancer, such as a tumor. In certain other embodiments, the disorder is a cardiovascular disorder, such as pulmonary hypertension, systemic hypertension, angina, Cardiac Syndrome X, myocardial infarction, peripheral artery disease, or Raynaud's disease.

In certain embodiments, the allosteric modulator of hemoglobin is one of the generic or specific an allosteric modulators of hemoglobin described in Section II, such as a compound of Formula I, a compound embraced by one of the further embodiments describing definitions for certain variables of Formula I, a compound of Formula I-A, or a compound embraced by one of the further embodiments describing definitions for certain variables of Formula I-A. In certain embodiments, the an allosteric modulator of hemoglobin is a compound of Formula II, a compound embraced by one of the further embodiments describing definitions for certain variables of Formula II, a compound of Formula I-A, or a compound embraced by one of the further embodiments describing definitions for certain variables of Formula II-A.

The description above describes multiple aspects and embodiments of the invention, including allosteric modulators of hemoglobin, compositions comprising an allosteric modulator of hemoglobin, methods of using the allosteric modulators of hemoglobin in combination with an inorganic nitrite salt, and kits. The patent application specifically contemplates all combinations and permutations of the aspects and embodiments. For example, the invention contemplates treating tumors in a human patient by administering a therapeutically effective amount of sodium nitrite in combination with an allosteric modulator of hemoglobin of Formula I-A. Further, for example, the invention contemplates a kit for treating tumors, the kit comprising (i) an inorganic nitrite salt described herein, such as sodium nitrite, (ii) an allosteric modulator of hemoglobin, such as a compound of Formula I, and (iii) instructions for treating a tumor.

EXAMPLES

The invention now being generally described, will be more readily understood by reference to the following examples, which are included merely for purposes of illustration of certain aspects and embodiments of the present invention, and are not intended to limit the invention.

Example 1

Figure 3:
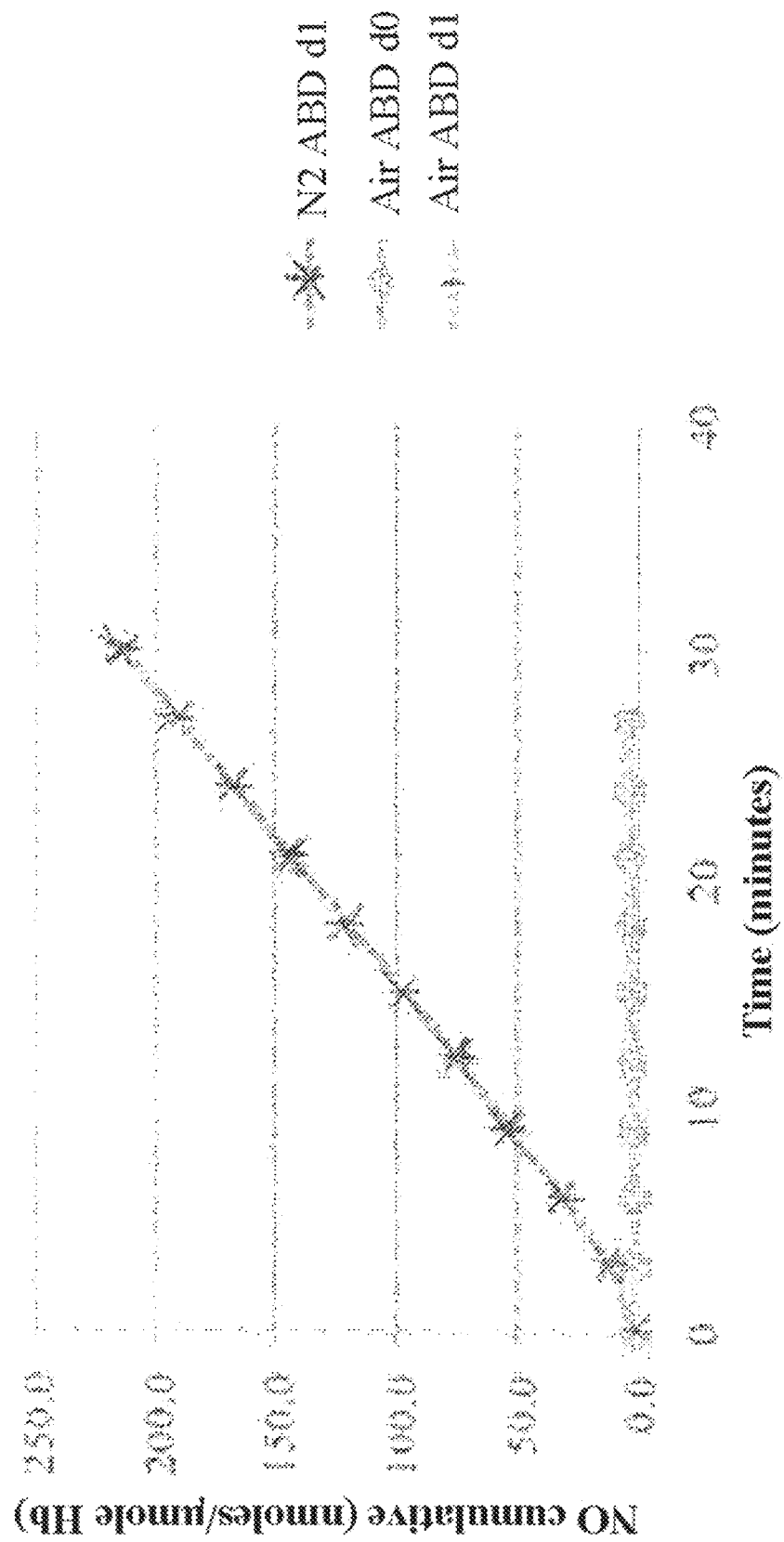
FIG. 3 is a graph showing the cumulative amount of nitric oxide formed from a blood sample mixed with ABDNAZ, where data is shown for a thirty-minute time period under an air atmosphere or $N_2$ atmosphere (where d0 refers to the first experiment, and d1 refers to the second repetition of the experiment), as described in Example 1.
Figure 4:
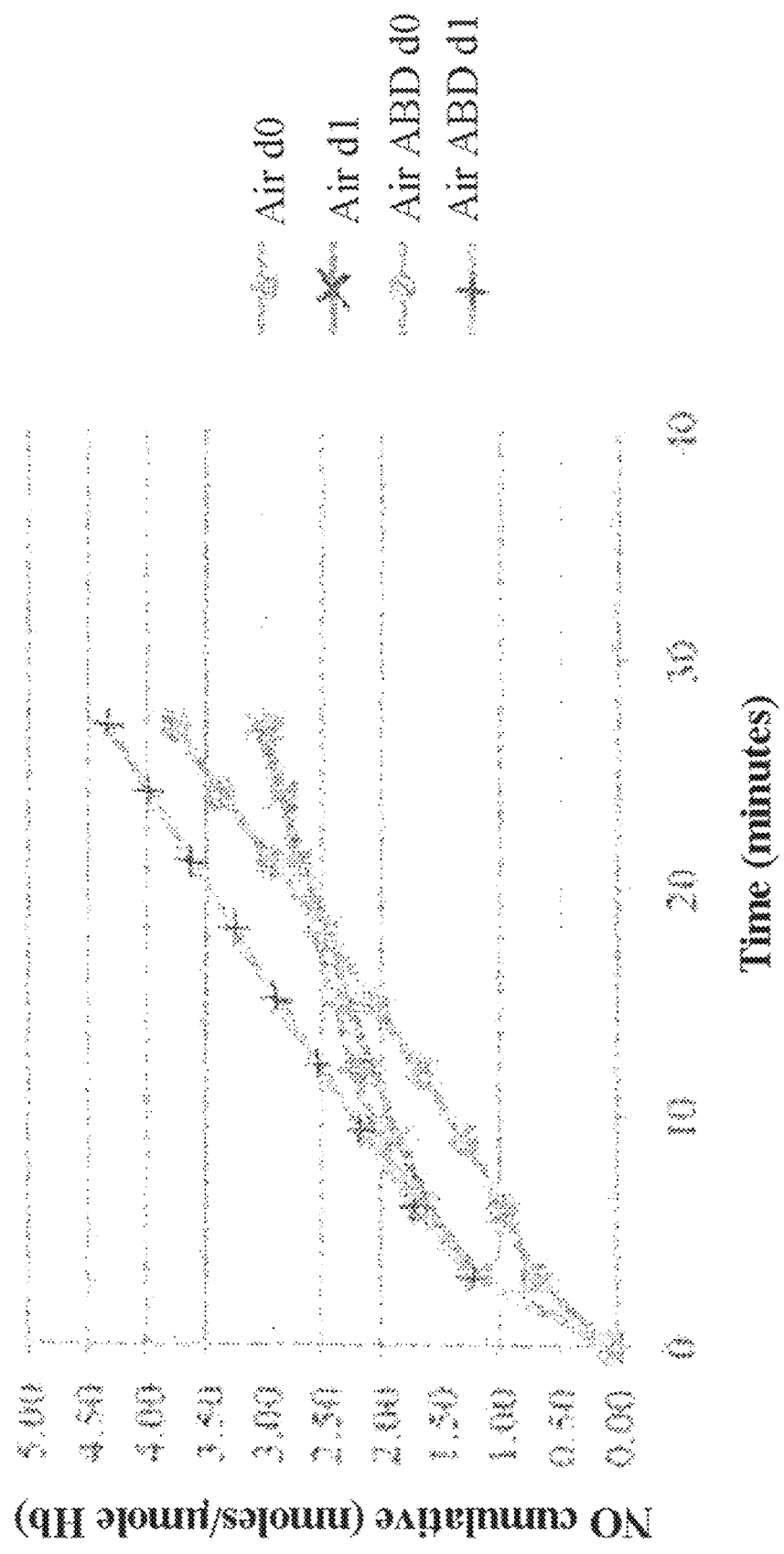
FIG. 4 is a graph showing the cumulative amount of nitric oxide formed from a blood sample under an atmosphere of air, where the blood sample is optionally mixed with ABDNAZ (where d0 refers to the first experiment, and d1 refers to the second repetition of the experiment), as described in Example 1.
Figure 5:
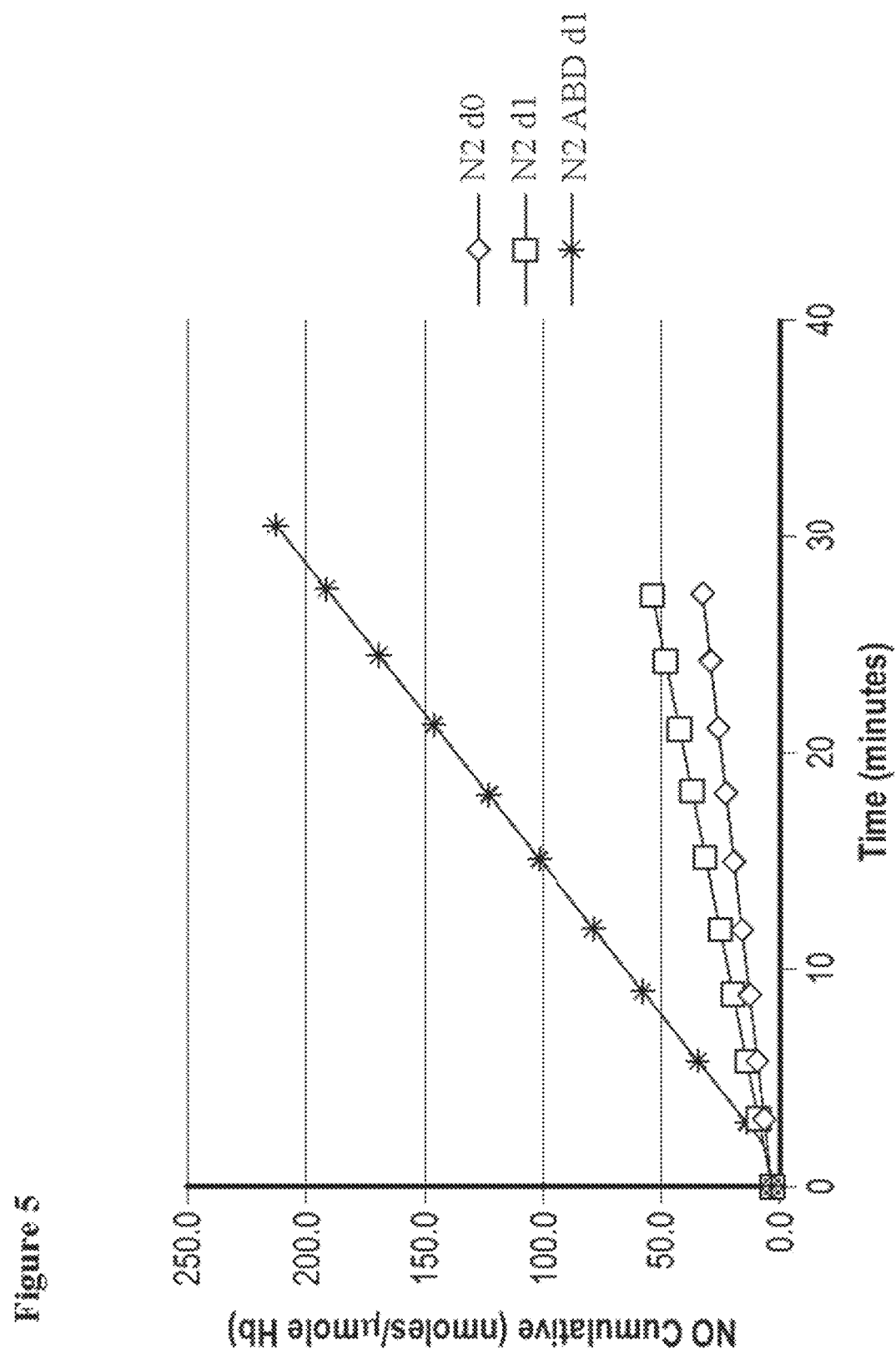
FIG. 5 is a graph showing the cumulative amount of nitric oxide formed from a blood sample under an atmosphere of $N_2$, where the blood sample is optionally mixed with ABDNAZ (where d0 refers to the first experiment, and d1 refers to the second repetition of the experiment), as described in Example 1.
Figure 6:
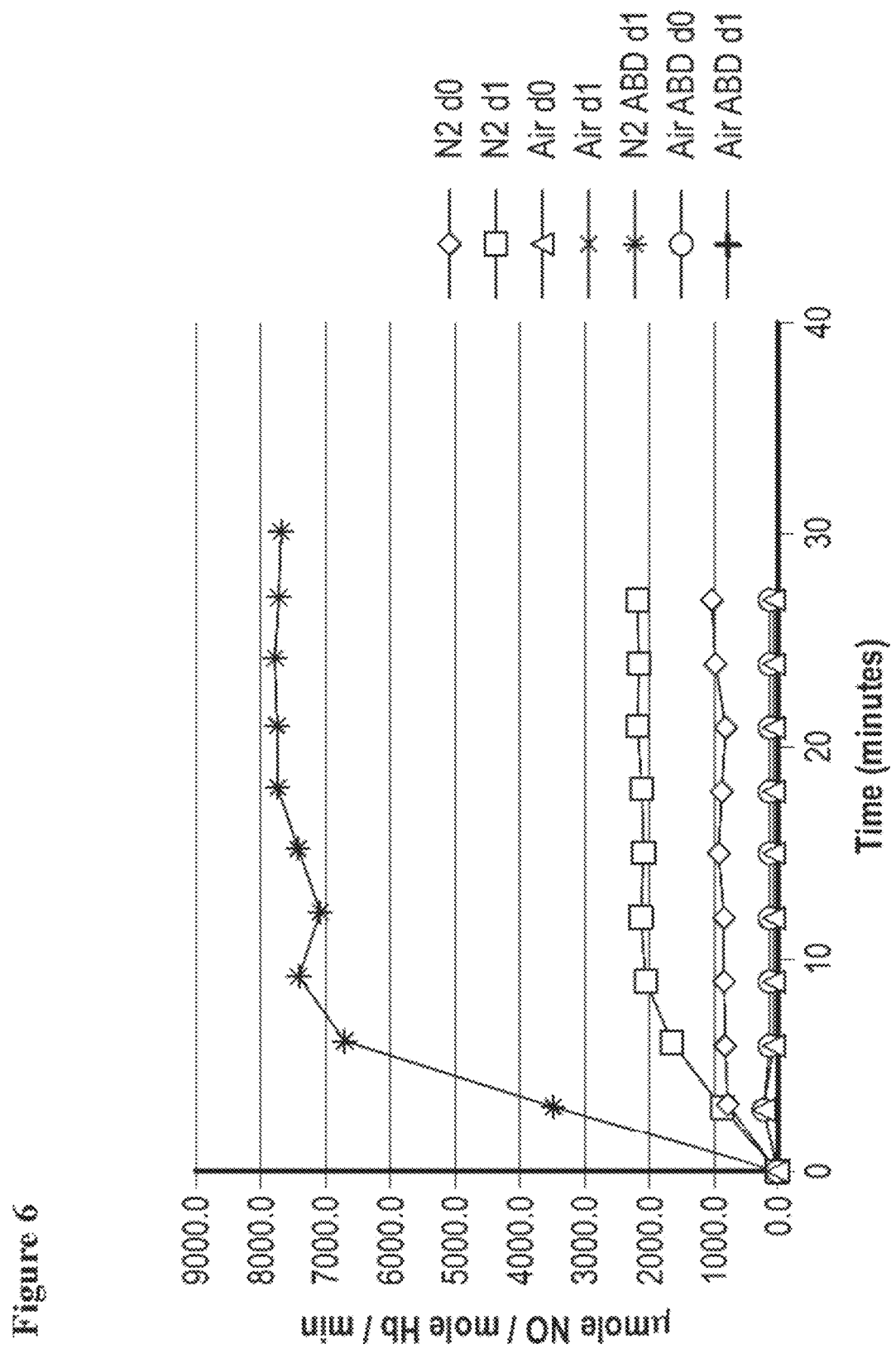
FIG. 6 is a graph showing the amount of nitric oxide formed in each three-minute period following the start of experiments for multiple experiments (experimental conditions varied include using an air atmosphere, N$_2$ atmosphere, and/or the presence or absence of ABDNAZ), as described in Example 1.
Figure 7:
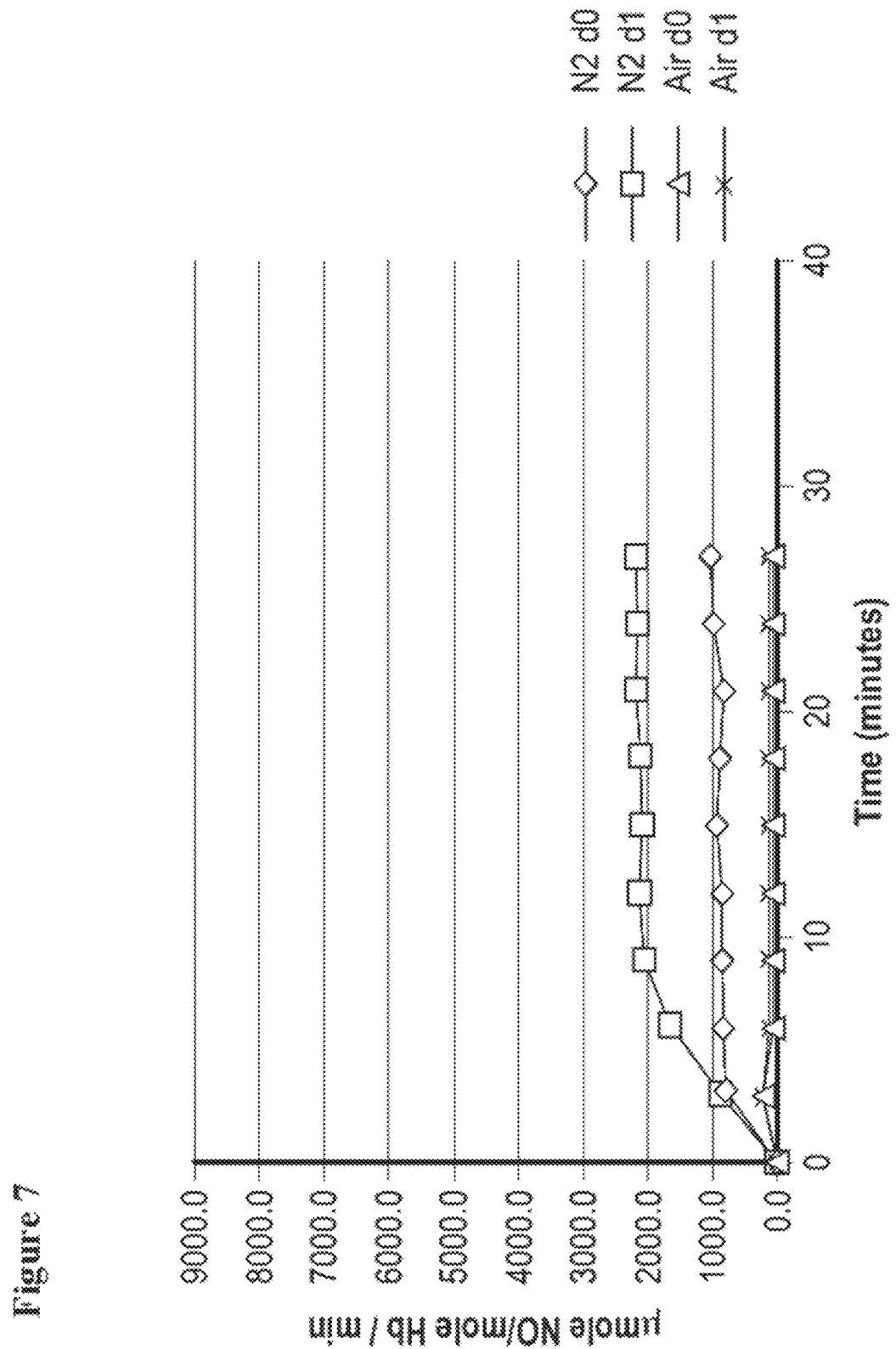
FIG. 7 is a graph showing the amount of nitric oxide formed in each three-minute period following the start of experiments where the blood sample is under an atmosphere of air or an atmosphere of N$_2$ as described in Example 1.
Figure 8:
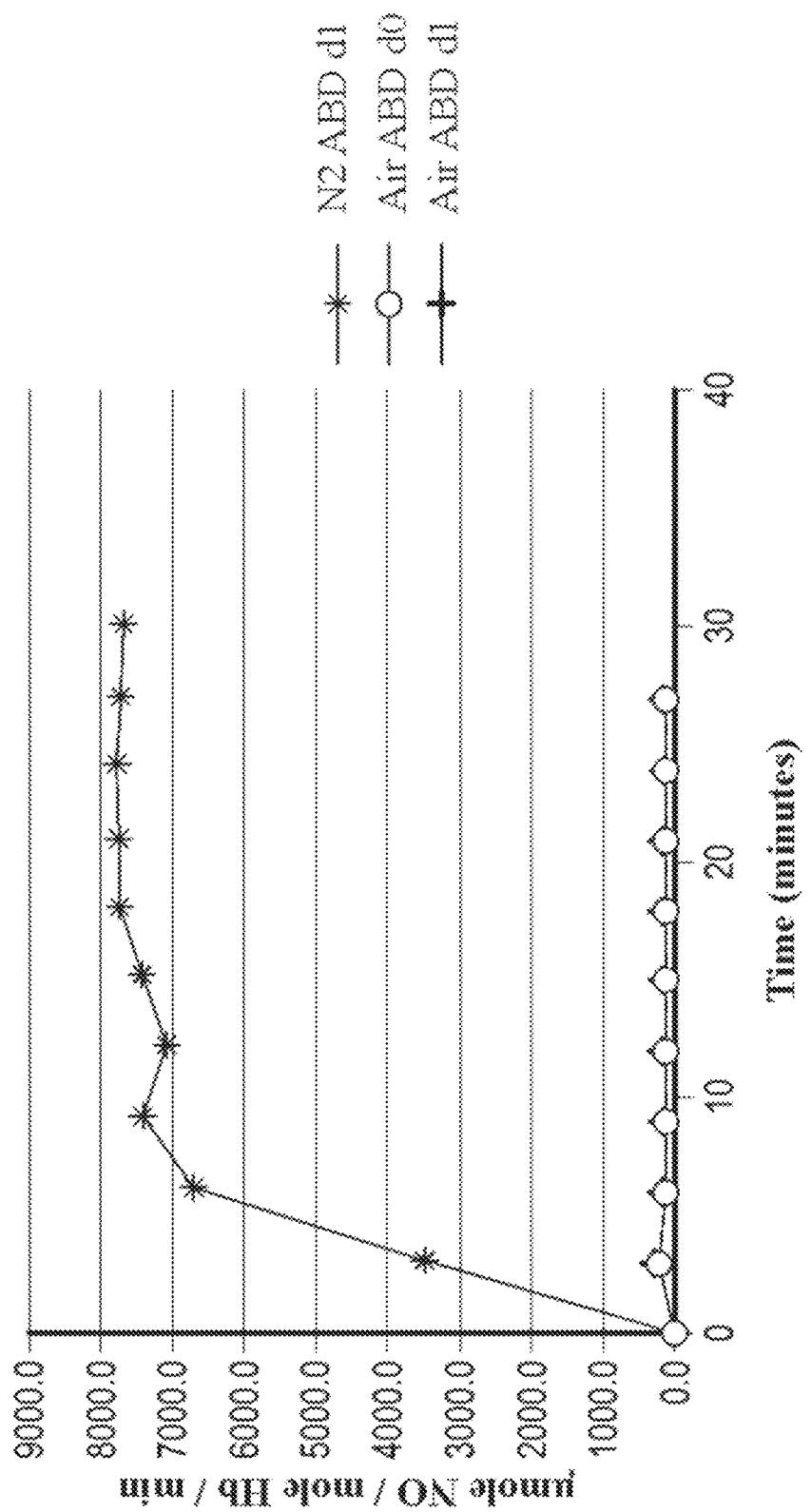
FIG. 8 is a graph showing the amount of nitric oxide formed in each three-minute period following the start of experiments where the blood sample is mixed with ABD-NAZ and is under an atmosphere of air or an atmosphere of N$_2$ as described in Example 1.

The ability of ABDNAZ to increase nitric oxide production in a sample of blood under aerobic conditions and anaerobic conditions was evaluated. Experimental procedures and results are provided below.
Experimental Procedures:
A 0.5 mL aliquot of blood was placed in a tonometer. ABDNAZ (5 µL of a 300 mM solution of ABDNAZ in dimethylsulfoxide) was optionally added to the blood sample in the Tonometer. Sodium nitrite was added to the blood sample to achieve a sodium nitrite concentration of 167 mM. Gas (either air or $N_2$) was passed through the Tonometer at a flow rate of 150 mL/min. Gas exiting the Tonometer was collected in three-minute intervals for a period of thirty minutes. The amount of nitric oxide in each of the collected fractions was measured by a chemiluminescent reaction with ozone in a Sievers Nitric Oxide Analyzer. The amount of nitric oxide produced from the blood sample was expressed per mole of hemoglobin present in the blood sample. All experiments were performed at 37° C.
The amount of hemoglobin (Hb) and hematocrit (Het) in the blood sample was determined using an Advia analyzer.
Results:
Experimental data showing the amount of nitric oxide produced by the blood samples are shown in FIGS. 1-8. In particular, FIGS. 1-5 show the cumulative amount of nitric oxide produced by the blood sample over a 30 minute time period. FIGS. 1, 3, and 5 show that exposing the blood sample to ABDNAZ under anaerobic conditions (i.e., $N_2$ atmosphere) resulted in a significant increase in the amount of nitric oxide produced by the blood sample, compared to the amount of nitric oxide produced (i) without ABDNAZ or (i) with ABDNAZ under aerobic conditions (i.e., air atmosphere). FIGS. 6-8 show the amount of nitric oxide formed in each three-minute period following the start of the experiment.

Example 2

The ability of ABDNAZ to enhance blood transfusion during resuscitation from hemorrhagic shock was evaluated. Experimental procedures and results are provided below.

Experimental Procedures:
Animal Preparation
Experiments were performed in 55-65 g male Golden Syrian Hamsters (Charles River Laboratories, Boston, Mass.) fitted with a dorsal skinfold window chamber. Animal handling and care followed the NIH Guide for the Care and Use of Laboratory Animals. The hamster window chamber model is widely used for microvascular studies in the unanesthetized state. The complete surgical technique is described in detail elsewhere, such as in Colantuoni et al. in *Am J Physiol* 1984; 246:H508-17. Three to four days after the initial surgery, the microvasculature was examined and only animals passing an established systemic and microcirculatory inclusion criteria, as previously described (e.g., in Cabrales P. Low dose nitrite enhances perfusion after fluid resuscitation from hemorrhagic shock. *Resuscitation* 2009; 80: 1431-6), were entered into the study.
Acute Hemorrhage Resuscitation Protocol
Acute hemorrhage was induced by withdrawing 50% of estimated total blood volume (BV) via the carotid artery catheter within 5 min. Total BV was estimated as 7% of body weight. One hour after hemorrhage induction, animals received 25% of BY of resuscitation (200 µl/min) via the jugular vein catheter, implemented with the volume resuscitation strategy defined by the group name, according to the scheme described before.
Experimental Groups
Animals were randomly divided into four experimental groups based on the resuscitation used, namely:
(1) Blood (group resuscitated with fresh blood only);
(2) Nitrite (group resuscitated with fresh blood followed by nitrite infusion);
(3) RRx-001 (group resuscitated with fresh blood treated with RRx-001 (i.e., ABDNAZ));
(4) RRx-001+nitrite (group resuscitated with fresh blood treated with RRx-001 (i.e., ABDNAZ) followed by nitrite infusion).

Fresh blood was collected from a donor, adult male Golden Syrian Hamsters (60-80 g). Briefly, hamster donors were anaesthetized, left carotid artery catheter was implanted, and blood was allowed to flow into heparinized tubes (sodium heparin 15 IU/mL). RBCs and plasma were separated by centrifugation (2700 rpm, 7 min). Buffy coat was discarded. RRx-001 treated cells were prepared by incubation of 1 mL of packed cells with 2 mg of RRx-001 for 30 minutes at 4° C., cells were rinsed 2× by centrifugation at 3,000 rpm with phosphate buffer saline (PBS) solution with 0.5% albumin (pre-filtered 0.22 µm, pH 7.4). After the final wash, red blood cells (RBCs) were adjusted to a 30% Het with fresh plasma. Although not wishing to be bound by a particular theory, it is believed that RRx-001 passes through the membrane of RBCs, binds to, and modifies hemoglobin (Hb).
For the groups that received "nitrite," 10 µM (in saline 100 µL) of sodium nitrite in saline was infused via the carotid artery catheter 10 minutes after resuscitation for the groups that received nitrite. An equal volume of saline was given to the other groups. To address effects of instrumentation and observation, an additional Sham group was included.
Experimental Protocol
Conscious animal was placed in a restraining tube with a longitudinal slit from which the window chamber protruded, then fixed to the microscopic stage for transillumination with the intravital microscope (BX51WI, Olympus, New Hyde Park, N.Y.). Animals were given 20 min to adjust to the tube environment before any measurements were made.

The tissue image was projected onto a charge-coupled device camera (4815, COHU, San Diego, Calif.) connected to a videocassette recorder and viewed on a monitor. Measurements were carried out using a 40× (LUMPFL-WIR, numerical aperture 0.8, Olympus) water immersion objective. Systemic (MAP, HR, Het, Hb, $PaO_2$, $PaCO_2$, pH, lactate, plasma nitrite, and metHb) and microvascular (arciorlar and venular diameters, blood flow, and FCD) parameters were analyzed, as previously described (e.g., in P. Nachuraju et al. in *Resuscitation* 2011; 82:607-613; Cabrales P. in *Resuscitation* 2009; 80:1431-6; Cabrales et al. in *Shock* 2007; 27:380-9; and Cabrales et al. in *Am J Physiol* 2004; 287:H363-73) before hemorrhage (baseline), after hemorrhage (shock), and up to 90 min after volume replacement (resuscitation). Tissue viability was measured at 8 hours following hemorrhage as described previously (e.g., in Yang et al. In *Invest Ophthalmol Vis Sci* 2003; 44:1993-1997; and Cabrales et al. in *Antioxid Redox Signal* 2007; 9:375-84).

Data Analysis

Table and figure results are presented as mean±SD. Data within each group were analyzed using analysis of variance for repeated measurements (Two-way ANOVA). When appropriate, post hoc analyses were performed with Bonferroni post-test. MetHb and Tissue viability data were analyzed using the Mann-Whitney U test. Microhemodynamic data are presented as absolute values and ratios relative to baseline values. The same vessels and capillary fields were followed so that direct comparisons to their baseline levels could be performed, allowing for more robust statistics. All statistics were calculated using GraphPad Prism 4.03 (GraphPad Software, Inc., San Diego, Calif.). Changes were considered statistically significant if $P<0.05$.

Results:

Systemic Response to Hemorrhage Resuscitation

Systemic hemodynamic and blood parameters are presented in Tables 1 and 2. The gold standard for treatment of hemorrhagic shock is resuscitation via blood transfusion. Thus, with the exception of blood pressure, treatment effects using RRx-001, nitrite, or both are compared to the blood only treatment group.

TABLE 1

SYSTEMIC PARAMETERS.

| | Hct (%) | Hb (g/dl) | Nitrite (nM) | BP (mmHg) | HR (bpm) |
|---|---|---|---|---|---|
| Baseline | | | | | |
| Sham | | | | 101 ± 5.6 | 406 ± 26 |
| RBCs | 50.0 ± 0.8 | 15.2 ± 0.2 | 440 ± 32 | 105.3 ± 6.4 | 416 ± 31 |
| Nitrite | 49.8 ± 0.8 | 15.2 ± 0.3 | 457 ± 23 | 104.3 ± 9.0 | 428 ± 13 |
| RRx-001 | 49.7 ± 1.0 | 15.1 ± 0.3 | 458 ± 21 | 106.3 ± 8.7 | 409 ± 21 |
| RRx-001 + Nitrite | 49.1 ± 0.9 | 15.0 ± 0.3 | 439 ± 13 | 107 ± 7.4 | 429 ± 22 |
| Shock (50 min) | | | | | |
| Sham | | | | 101.9 ± 5.8 | 412 ± 35 |
| RBCs | 28.8 ± 0.6 | 8.8 ± 0.2 | | 45.5 ± 4.8 | 425 ± 43 |
| Nitrite | 29.2 ± 0.5 | 8.9 ± 0.1 | | 46.1 ± 3.6 | 455 ± 21 |
| RRx-001 | 29.0 ± 0.8 | 8.9 ± 0.3 | | 46.3 ± 4.0 | 422.5 ± 25 |
| RRx-001 + Nitrite | 28.8 ± 0.4 | 8.8 ± 0.1 | | 47.8 ± 4.4 | 453 ± 31 |
| Resuscitation (30 min) | | | | | |
| Sham | | | | 102.5 ± 5.3 | 426 ± 42 |
| RBCs | | | | 102.4 ± 7.9 | 359 ± 36 |
| Nitrite | | | | 91.3 ± 6.9 | 438 ± 21 |
| RRx-001 | | | | 92.5 ± 6.7 | 436 ± 12 |
| RRx-001 + Nitrite | | | | 88.7 ± 7.4 | 524 ± 44 |
| Resuscitation (60 min) | | | | | |
| Sham | | | | 101.5 ± 5.2 | 425 ± 44 |
| RBCs | 31.4 ± 0.4 | 9.5 ± 0.2 | | 79.8 ± 6.3 | 373 ± 37 |
| Nitrite | 31.0 ± 0.7 | 9.5 ± 0.2 | | 96.3 ± 7.5 | 447 ± 21 |
| RRx-001 | 31.1 ± 0.6 | 9.5 ± 0.2 | | 98.5 ± 7.6 | 444 ± 10 |
| RRx-001 + Nitrite | 31.1 ± 0.7 | 9.4 ± 0.2 | | 91.2 ± 9.1 | 517 ± 39 |
| Resuscitation (90 min) | | | | | |
| Sham | | | | 101.6 ± 5.4 | 426 ± 43 |
| RBCs | 31.0 ± 0.4 | 9.5 ± 0.1 | 678 ± 39 | 106.5 ± 5.7 | 384 ± 47 |
| Nitrite | 31.5 ± 0.4 | 9.6 ± 0.1 | 791 ± 100 | 94.7 ± 6.5 | 459 ± 14 |
| RRx-001 | 31.2 ± 0.6 | 9.5 ± 0.1 | 636 ± 54 | 106.3 ± 9.0 | 453 ± 17 |
| RRx-001 + Nitrite | 30.6 ± 0.4 | 9.3 ± 0.1 | 799 ± 56 | 99.1 ± 1.04 | 530 ± 43 |

TABLE 2

ADDITIONAL SYSTEMIC PARAMETERS

| | pH | pO2 (mmHg) | pCO2 (mmHg) | Lactate (mmol/L) |
|---|---|---|---|---|
| Baseline | | | | |
| Sham | | | | |
| RBCs | 7.33 ± 0.02 | 58.9 ± 1.5 | 53.3 ± 1.1 | 1.42 ± 0.19 |
| Nitrite | 7.34 ± 0.02 | 60.5 ± 1.0 | 52.9 ± 1.2 | 1.30 ± 0.13 |
| RRx-001 | 7.32 ± 0.01 | 59.9 ± 2.5 | 54.2 ± 1.8 | 1.39 ± 0.20 |
| RRx-001 + Nitrite | 7.33 ± 0.02 | 61.1 ± 1.6 | 53.7 ± 1.6 | 1.37 ± 0.19 |
| Shock (50 min) | | | | |
| Sham | | | | |
| RBCs | 7.29 ± 0.01 | 91.6 ± 3.8 | 37.9 ± 0.7 | 4.37 ± 0.30 |
| Nitrite | 7.30 ± 0.01 | 93.1 ± 2.8 | 38.9 ± 1.3 | 4.52 ± 0.58 |
| RRx-001 | 7.28 ± 0.02 | 94.9 ± 5.1 | 39.3 ± 1.2 | 4.16 ± 0.39 |
| RRx-001 + Nitrite | 7.28 ± 0.02 | 98.0 ± 3.9 | 38.4 ± 1.2 | 4.19 ± 0.57 |
| Resuscitation (30 min) | | | | |
| Sham | | | | |
| RBCs | | | | |
| Nitrite | | | | |
| RRx-001 | | | | |
| RRx-001 + Nitrite | | | | |
| Resuscitation (60 min) | | | | |
| Sham | | | | |
| RBCs | 7.34 ± 0.01 | 69.8 ± 1.7 | 50.6 ± 1.5 | 2.08 ± 0.22 |
| Nitrite | 7.38 ± 0.02 | 76.0 ± 2.9 | 48.3 ± 2.2 | 1.95 ± 0.11 |
| RRx-001 | 7.39 ± 0.01 | 70.9 ± 3.4 | 48.0 ± 3.1 | 1.93 ± 0.23 |
| RRx-001 + Nitrite | 7.39 ± 0.02 | 79.5 ± 4.3 | 44.7 ± 2.1 | 1.41 ± 0.12 |
| Resuscitation (90 min) | | | | |
| Sham | | | | |
| RBCs | 7.35 ± 0.02 | 63.1 ± 1.6 | 51.0 ± 1.8 | 1.86 ± 0.18 |
| Nitrite | 7.36 ± 0.02 | 65.2 ± 3.0 | 45.0 ± 2.4 | 1.71 ± 0.20 |
| RRx-001 | 7.36 ± 0.01 | 68.7 ± 2.9 | 49.0 ± 2.2 | 1.63 ± 0.23 |
| RRx-001 + Nitrite | 7.38 ± 0.02 | 70.4 ± 3.9 | 50.7 ± 2.7 | 1.41 ± 0.14 |

During hemorrhagic shock, Hct and Hb dropped about 50% for all treatment groups and no significant differences were seen between groups at any time during the study. Although resuscitation partially restored blood pressure (MAP) from shock in all treatment groups, MAP was significantly decreased in the RRx-001 group at 60 minutes. Compared to the blood group, significant differences in MAP and heart rate were seen in the blood+nitrite, RRx-001, and RRx-001+nitrite groups following resuscitation. For the nitrite group, MAP was significantly decreased at 30 and 90 minutes. MAP in the RRx-001, was only decreased at 30 minutes and in the RRx-001 nitrite group it was significantly decreased at 30 and 60 minutes. HR for the nitrite. RRx-001, and RRx-001+nitrite treatment groups compared to the blood group was significantly increased.

Hemorrhagic shock decreased arterial pH and pCO2, significantly compromising acid based balance relative to baseline. Resuscitation partially recovered all blood gas parameters. In the nitrite, RRx-001, and RRx-001+nitrite groups, pH was significantly increased at 60 minutes post resuscitation compared to the blood group. For the RRx-001+nitrite group, pH was also significantly increased at 90 minutes post resuscitation. pO2 levels were significantly increased: in the in the nitrite group at 60 minutes post resuscitation; in the RRx-001 group at 90 minutes post resuscitation; in the RRx-001+nitrite group, during 60 minutes of shock and at 60 and 90 minutes post resuscitation. Compared to the blood group, pCO2 levels in the RRx-001 group were not significantly different. In the RRx-001+ nitrite group, lactate (lact) levels were significantly decreased at 60 and 90 minutes post-resuscitation. Decreases in lactate levels in the nitrite and RRx-001 groups did not reach significance.

Figure 9:
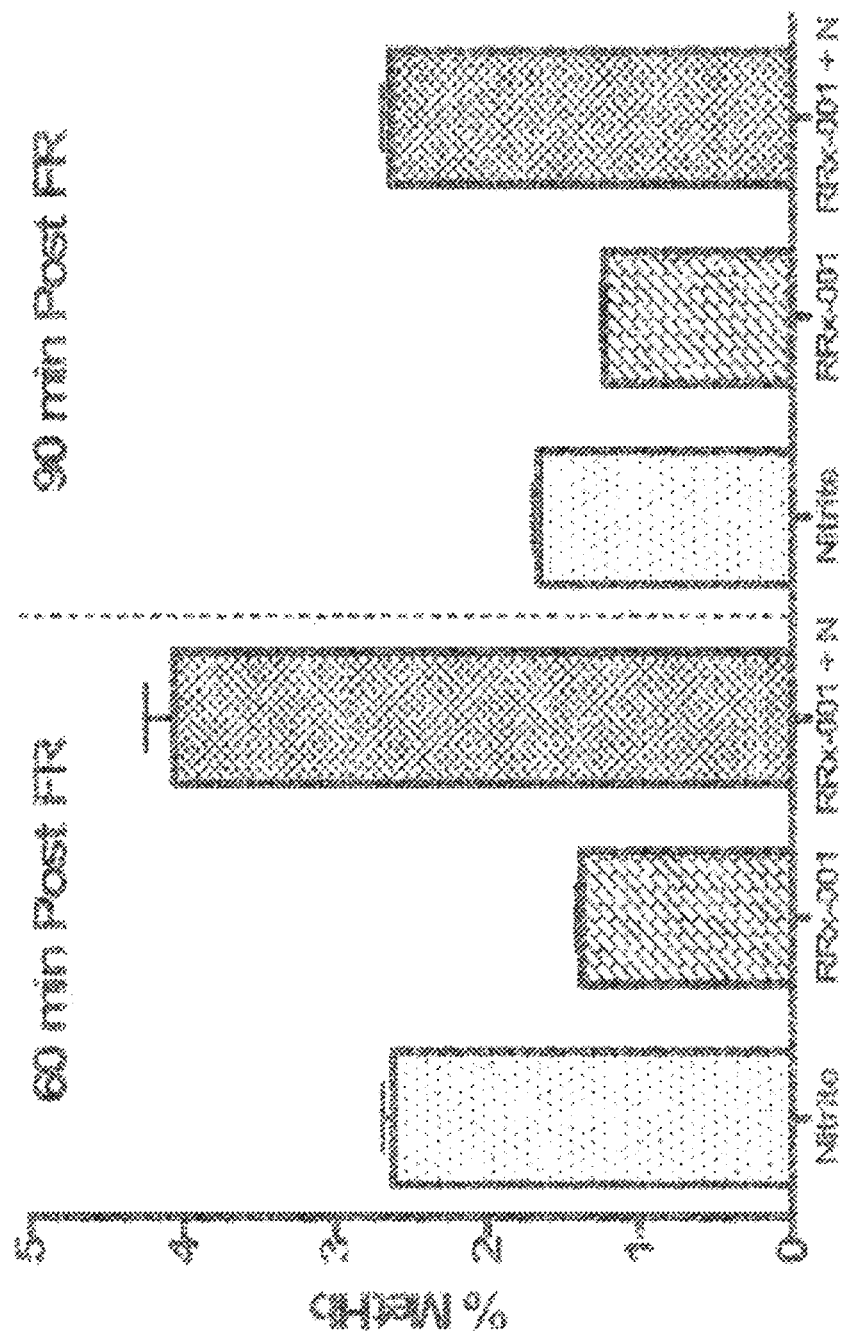
FIG. 9 is a bar graph showing percent MetHb for the (i) nitrite, (ii) RRx-001, and (iii) RRx-001+nitrite (RRx-001+N) groups at 60 and 90 minutes post fluid resuscitation (FR), as further described in Example 2. It is noted that the percent MetHb level in normal, healthy individuals is about 1.

The percent MetHb levels for the nitrite, RRx-001, and RRx-001+nitrite groups are presented in FIG. 9. In normal, healthy individuals metHb levels are about 1% of the total Hb and methemoglobinemia occurs when the concentration of metHb in the blood exceeds 1.5 g/dL (8%-12% of the normal Hb level). See, for example, Hamirani et al. in *Tex Heart Inst J* 2008; 35:76-77. Of the three treatment groups, only RRx-001 had normal metHb levels.

Microvascular Measurements

Figure 10:
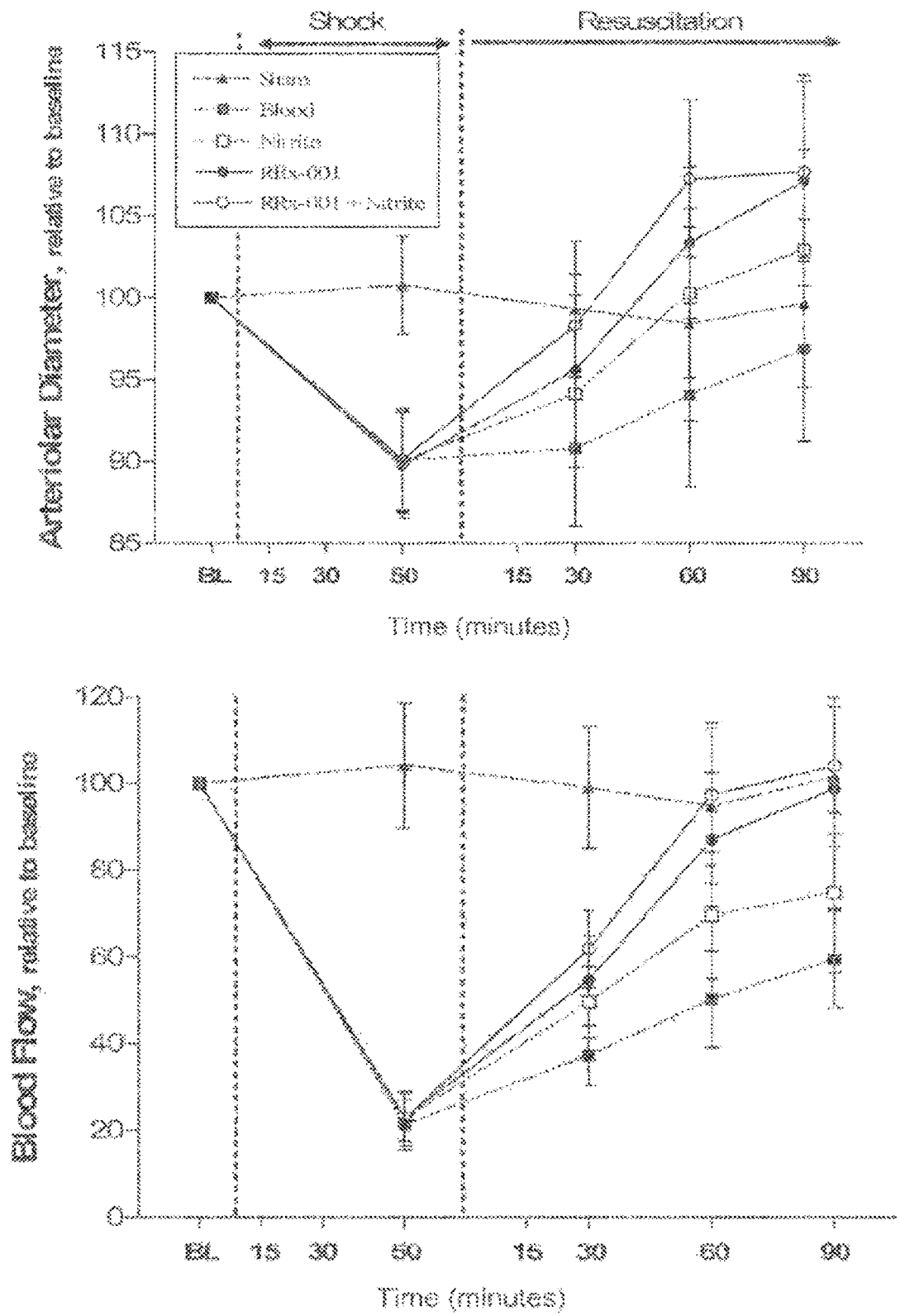
FIG. 10 depicts line graphs showing relative changes in arteriolar diameter and blood flow during hemorrhagic shock and resuscitation for all groups tested in Example 2.

Changes in arteriolar diameter and blood flow during the hemorrhagic shock resuscitation protocol for all experimental groups are presented in FIG. 10. Compared to the blood group, arterial diameter and blood flow were increased in all treatment groups. However, these increases only reached significance in the RRx-001 and RRx-001+nitrite groups. Arteriolar diameter was significantly increased at 60 and 90 minutes ($P<0.01$ and $P<0.05$, respectively) only in RRx-001+nitrite following resuscitation and blood flow was significantly ($P<0.001$) increased in the both the RRx-001 and RRx-001+nitrite groups at 60 and 90 minutes. At 30 minutes post resuscitation, the difference in blood flow between the blood only and RRx-001+nitrite groups was also significant ($P<0.05$).

Figure 11:
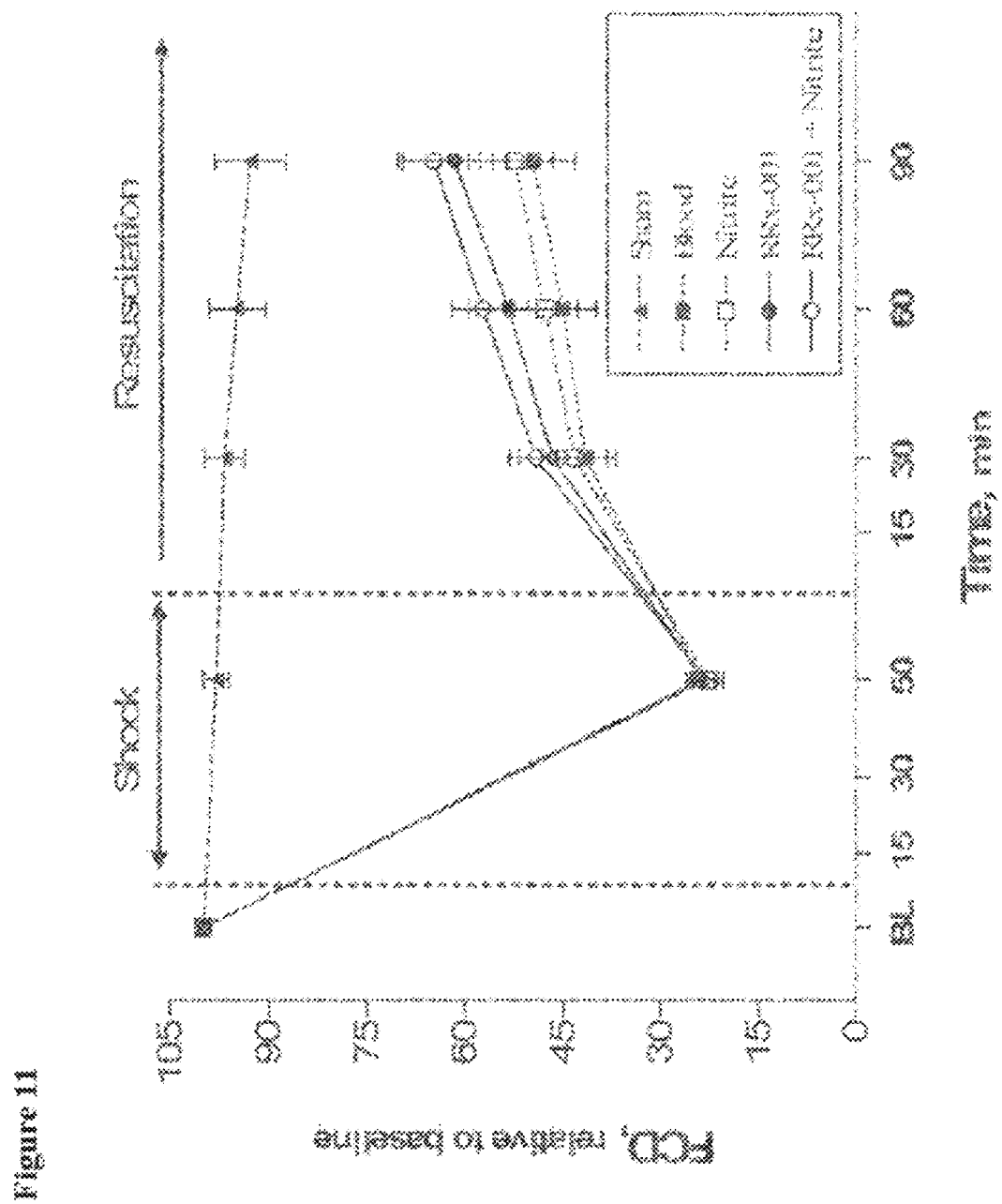
FIG. 11 is a line graph showing relative changes in functional capillary density (FCD) during hemorrhagic shock and resuscitation for all groups tested in Example 2. Baseline averages and standard deviations for each of the groups are: Sham, 106±11; Blood, 107±10; Nitrite, 107±12; RRx-001, 112±9; RRx-001+Nitrite, 108±9.

Changes in the number of capillaries perfused with RBCs during the protocol are presented in FIG. 11. Resuscitation partially restored hemorrhage induced reductions in functional capillary density (FCD) in all groups. Again, compared to the blood group, FCD was not significantly different in the nitrite group following resuscitation. However, both RRx-001 and RRx-001+nitrite treatment resulted in significant ($P<0.05$ and $P<0.01$, respectively) increases in FCD at 90 minutes post resuscitation. Statistical significance ($P<0.05$) was also observed at 60 minutes in the RRx-001+nitrite group.

Figure 12:
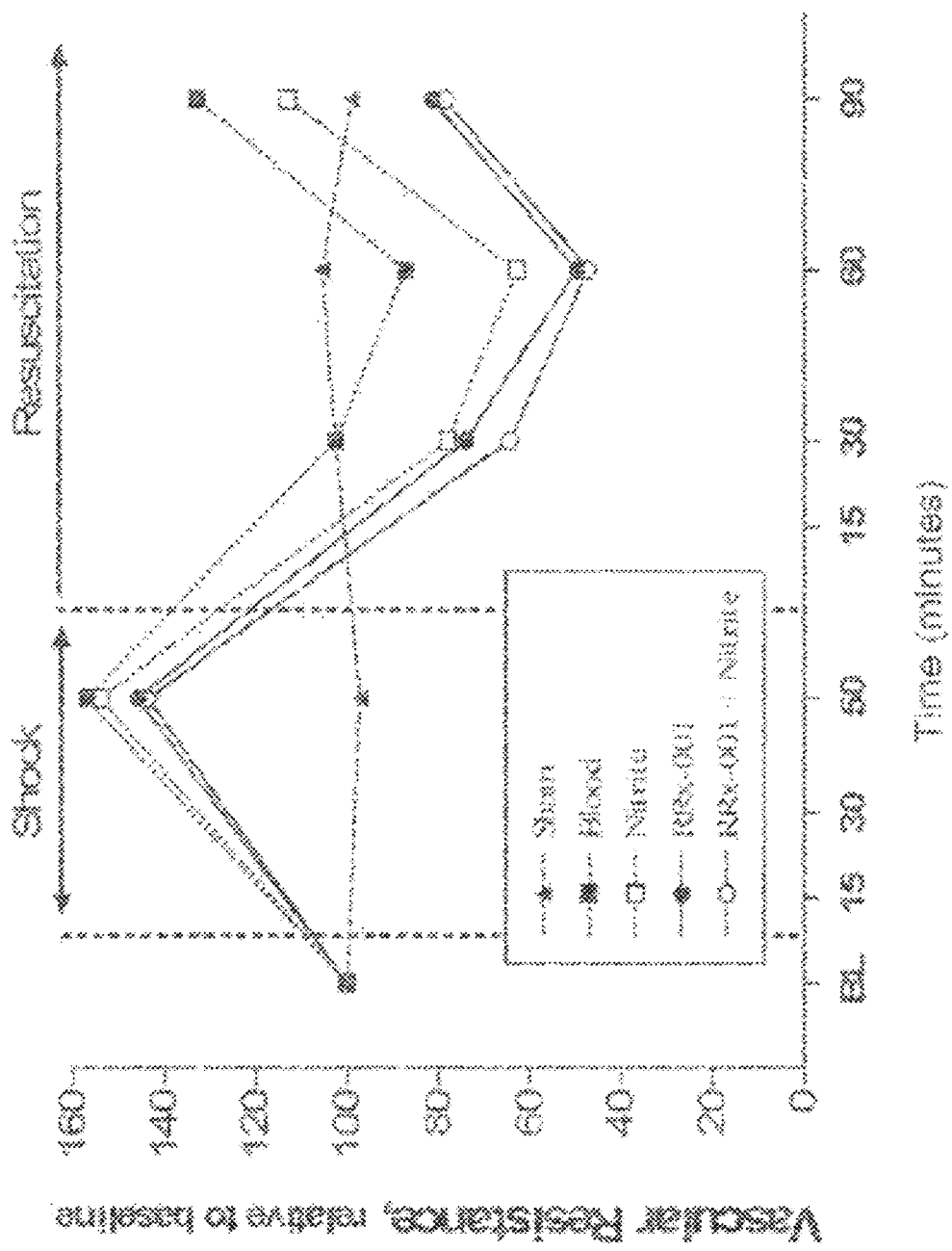
FIG. 12 is a line graph showing calculated vascular resistance (MAP/blood flow) relative to baseline during hemorrhagic shock and resuscitation for all groups tested in Example 2.

Calculated vascular resistance (average MAP/average blood flow) relative to baseline is presented in FIG. 12. Peripheral vascular resistance for all groups increased after hemorrhagic shock (about 1.5 times the resistance at baseline) and decreased after resuscitation. The RRx-001 and RRx-001+nitrite groups had a similar impact on vascular resistance.

Tissue Viability

Figure 13:
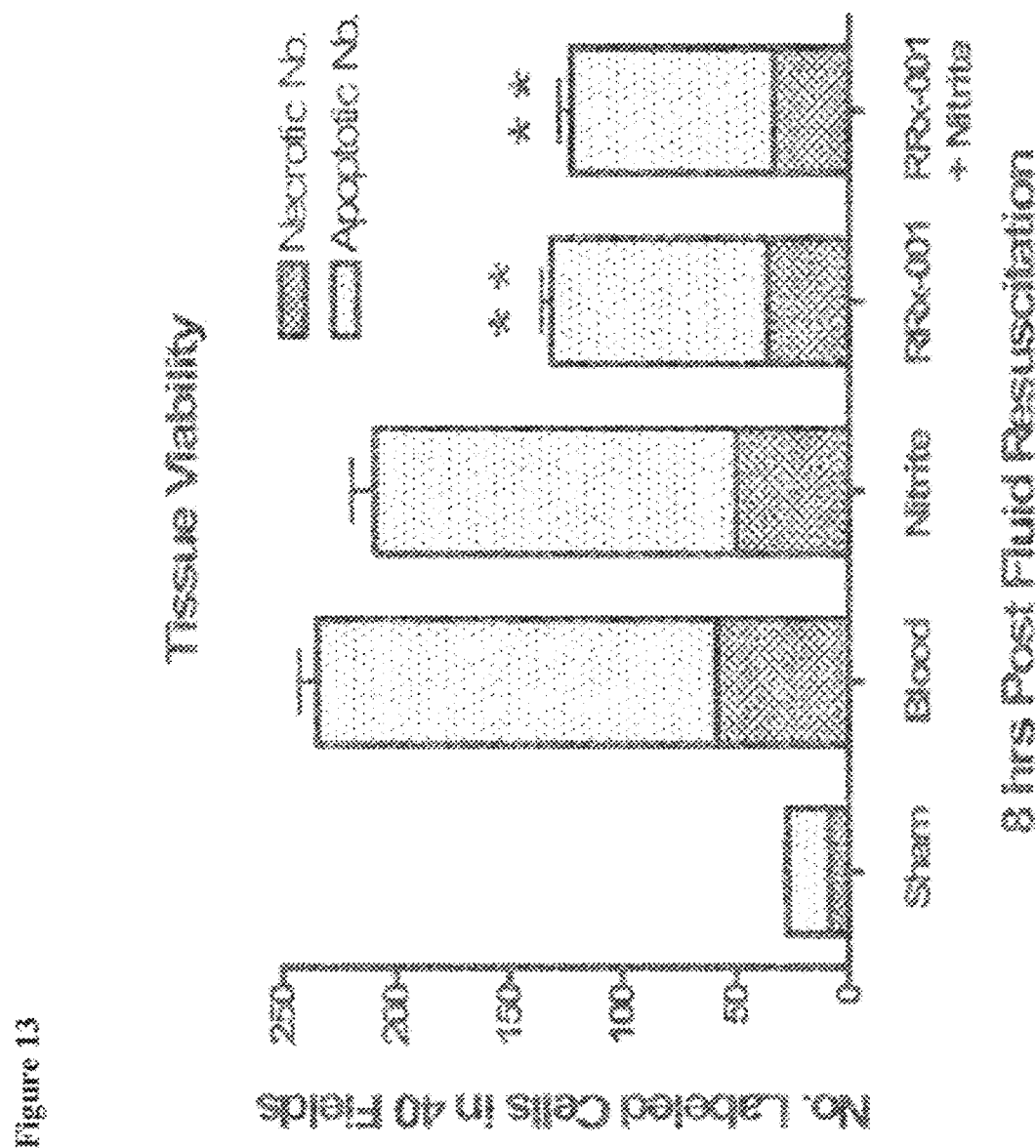
FIG. 13 is a bar graph showing the number of apoptotic and necrotic cells at 8 hours following resuscitation for all groups tested in Example 2. Data is presented as the average of fluorescent cells counted in 40 selected visual fields (210×160 µm) for the tissue and the endothelial vessel wall separately. **P<0.005 for both the number of apoptotic and necrotic in the RRx-001 and RRx-001+nitrite groups compared to blood only.

Tissue viability (the number of apoptotic and necrotic cells in 40 fields) for all treatment groups at 8 hours following resuscitation is presented in FIG. 13. The number of apoptotic cells in the RRx-001 and RRx-001+nitrite groups was significantly ($P<0.01$) less than the blood group. The number of necrotic cells was also significantly ($P<0.01$) less in the RRx-001 and RRx-001+nitrite groups compared to the blood group. Supplementation with nitrite also significantly reduced the number of necrotic cells.

Discussion:

Experimental results show that RRx-001 treated blood with or without nitrite supplementation provides superior systemic and microvascular hemodynamic responses compared to blood transfusion with or without nitrite. Incorporating RRx-001 into transfusion-based resuscitation affords the added benefit of selectively increasing NO generation under hypoxic conditions. Without being bound by a particular theory, it is believed that RRx-001 generates NO in two ways: i) as an NO donor: through metabolism of the dinitro groups released from the compound, and ii) as an NO promoter: beta-Cys-93 modification by RRx-001 enhances hypoxia-mediated nitrite reduction to NO by deoxyhemoglobin. Our results demonstrate that these RRx-001 mediated benefits improved systemic and microvascular parameters, which appears to correlate with tissue viability. Thus, RRx-001 treated blood should minimize short and long term organ damage after hemorrhagic shock.

Hemorrhagic hypotension leads to a well-characterized sequence of events, and ultimately to vascular decompensation, due to a continuous increase in peripheral vascular resistance. The outcome of hemorrhagic shock is related to the degree of hypovolemia, the magnitude of acquired oxygen debt, and the delay in treatment. Monitoring the microcirculation is crucial in determining the effect of changes in intravascular volume in tissue hypo-perfusion. Application of various techniques, including intravital microscopy, has shown the presence of major microcirculatory alterations during hemorrhage, and the persistence of these microcirculatory alterations have been associated with multiorgan failure and death. See, for example, Sinaasappel et al. in *J Physiol* 1999; 514(Pt 1):2415-253; and Ellis et al. in *Crit Care* 2005; 9(Suppl 4):S3-8.

Blood transfusion is currently the gold standard for treatment of severe hemorrhagic shock. When blood is used during resuscitation, intravascular blood volume and oxygen carrying capacity are restored, cardiovascular function improves, energy requirements are met, and survival more likely. Practically however, transfusion post hemorrhage recovers the microcirculation, but not necessarily to normal levels. The injury resulting from the shock phase prior to resuscitation limits perfusion during the resuscitation and thus prevents full recovery of the microcirculation immediately post resuscitation. Moreover, when blood is used during resuscitation, "normal" MAP is restored, however restoring MAP is not necessarily accompanied by the restoration of organ perfusion and oxygenation, due to microvascular flow dysfunctions (the so-called "no reflow" phenomenon). See, for example, Zakaria et al. in *J Trauma* 2005; 58:499-508; and Rezkalla et al. in *Circulation* 2002; 105:656-62. During the shock phase and immediately post resuscitation, vascular endothelial shear stress and endothelium NO synthase (eNOS) activity is also impaired and results in delayed dilation of the endothelium. Over time, eNOS activity and microvascular flow dysfunction recover. However, if the resuscitation is inadequate during this critical period multi-organ injury can ensue. The results of our study suggest that during the time when NO synthase is still malfunctioning, incorporation of RRx-001 with blood resuscitation, via restoration of intravascular NO concentration, would increase perfusion by relaxing arterioles and lowering vascular resistance leading to improved microvascular function, reduced cell death, and preserved tissue viability, ensuring a better overall outcome compared to blood transfusion alone.

The use of NO donors under conditions of hemorrhagic shock have been shown to result in enhanced myocardial contractile activity that leads to a situation where mean arterial pressure does not decrease further despite significant decrease of total peripheral resistance. Remizova and colleagues studied the effects of an NO donor, DNIC-GS (dinitrosyl iron complexes with glutathione) in a hemorrhagic shock model. See, for example, Remizova et al. in *Eur J Pharmacol* 2011; 662:40-46. They found that injection of DNIC-GS into the blood flow of rats prior to hemorrhage by increased stroke volume, left ventricular work, and cardiac output. The results of our study indicate that RRx-001 should improve these indices of cardiac function in the face of decreased vascular resistance.

Nitrite, a biologic metabolite of NO, present in a variety of foods. Nitrite has been appreciated as an inflammatory mediator of nitration reactions and a precursor for NO under acidic or ischemic conditions and plasma nitrite levels correlate with eNOS activity and are tightly controlled. We have previously studied the effects of nitrite supplementation (10 µM and 50 µM nitrite) on systemic (BP, HR, pH, pO2, pCO2) and microvascular parameters (arteriolar diameter, blood flow, FCD) after resuscitation from hemorrhagic shock. Similar effects on systemic and microvascular parameters were observed with the administration of 10 µM nitrate compared to the nitrite group in the present study. By comparison, administration of 50 µM nitrite had a more profound effect on arteriolar diameter and blood flow but negatively affected blood pressure and metHb levels. Blood pressure in the 50 µM nitrite group was significantly decreased compared to 0 µM group (control group) at 60 minutes following resuscitation and at 60 and 90 minutes; % metHb was 5.8±1.8 and 3.1±1.3, respectively. In the current study, RRx-001 treatment maintained blood pressure following resuscitation and resulted in metHb levels of only 1.4±0.1 at 60 minutes and 1.2±0.1 at 90 minutes which corresponds to metHb levels in healthy individuals of about 1% of the total Hb: Methemoglobinemia occurs when the concentration of metHb in the blood exceeds 1.5 g/dL (8%-12% of the normal Hb level), where tissue oxygenation is compromised.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A method of treating a patient suffering from hemorrhagic shock, comprising:
   administering to a patient in need thereof whole blood and a therapeutic agent, wherein the patient receives, by intravenous injection, a single composition comprising the whole blood and the therapeutic agent, wherein the therapeutic agent is:

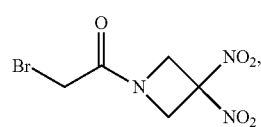

or a pharmaceutically acceptable salt or solvate thereof, and
   wherein administering the whole blood and the therapeutic agent achieves an improved systemic and microvascular hemodynamic response compared to a blood transfusion, with or without nitrite supplementation.

2. The method of claim 1, wherein the therapeutic agent is

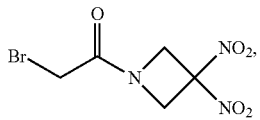

3. A method of performing a blood transfusion to a patient suffering from hemorrhagic shock, comprising:
   administering to a patient in need thereof a whole blood and a therapeutic agent, wherein the patient receives, by intravenous injection, a single composition comprising the whole blood and the therapeutic agent, wherein the therapeutic agent is:

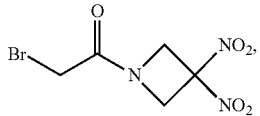

or a pharmaceutically acceptable salt or solvate thereof, and wherein administering the whole blood and the therapeutic agent achieves an improved systemic and microvascular hemodynamic response compared to a blood transfusion, with or without nitrite supplementation.

4. The method of claim 3, further comprising administering an alkali metal nitrite to the patient.

5. The method of claim 3, further comprising administering sodium nitrite to the patient.

6. The method of claim 3, wherein the therapeutic agent is

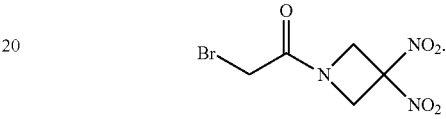

* * * * *